United States Patent
Bornscheuer et al.

(10) Patent No.: US 8,975,055 B2
(45) Date of Patent: Mar. 10, 2015

(54) REDUCED-FAT FOODSTUFFS AND COOKING OILS, AND METHODS FOR MAKING SAME

(71) Applicant: Frito-Lay Trading Company GmbH, Bern (CH)

(72) Inventors: Uwe Bornscheuer, Greifswald (DE); Henrike Brundiek, Lengerich (DE); Andrew Evitt, London (GB); Stefan Saβ, Greifswald (DE); Friedericke Bonisch, Freising (DE); Robert Kourist, Neufahrn (DE)

(73) Assignee: Frito-Lay Trading Company GmbH, Berne (CH)

( * ) Notice: Subject to any disclaimer, the term of this patent is extended or adjusted under 35 U.S.C. 154(b) by 205 days.

(21) Appl. No.: 13/794,173

(22) Filed: Mar. 11, 2013

(65) Prior Publication Data
US 2013/0171321 A1 Jul. 4, 2013

Related U.S. Application Data

(62) Division of application No. 13/098,124, filed on Apr. 29, 2011.

(51) Int. Cl.
C12N 9/20 (2006.01)
A23D 9/04 (2006.01)
C12P 7/64 (2006.01)

(52) U.S. Cl.
CPC .. *C12N 9/20* (2013.01); *A23D 9/04* (2013.01); *C12P 7/6454* (2013.01)
USPC ............................................. 435/198; 435/18

(58) Field of Classification Search
CPC ........................................................ C12N 9/20
USPC ...................................................... 435/18, 198
See application file for complete search history.

(56) References Cited

U.S. PATENT DOCUMENTS 7,303,877 B2  12/2007  Connelly et al.

OTHER PUBLICATIONS

Wood, et al., "Effect of butter, mono- and polyunsaturated fatty acid-enriched butter, trans fatty acid margarine, and zero trans fatty acid margarine on serum lipids and lipoproteins in healthy men" Journal of Lipid Research, vol. 34, 1993, pp. 1-11.
Database UniProt [Online] Jul. 19, 2005, "Subname: Full=Putative uncharacterized protein", XP002681548, retrieved from EBI accession No. TR:Q4P903 USTMA Database accession No. Q4P903.
Brundiek, Henrike, et al., "The short form of the recombinant CAL-A-type lipase UM03410 from the smut fungus Ustilago maydis exhibits an inherent trans-fatty acid selectivity," Appl. Microbiol. Biotechnol., 94:141-150, 2012, 10 pages.

*Primary Examiner* — Tekchand Saidha
(74) *Attorney, Agent, or Firm* — Colin P. Cahoon; Celina M. Orr; Carstens & Cahoon, LLP

(57) ABSTRACT

The present invention relates to a newly identified lipase belonging to the Ustilaginaceae family of Basidomycetes and variants thereof. The invention also relates to polynucleotides encoding the lipase and the variants thereof. The invention further relates to procedures for producing the lipase, and variants thereof, polypeptides and polynucleotides. The invention further relates to lipase variants with an increased trans-selectivity. The invention further relates to lipase variants with a preference for long chain fatty acid esters or carboxylic acid moieties with a chain length greater than $C_{12}$. The invention further relates to a method of reducing, or eliminating, trans-fatty acids from liquid oil stable enough for frying systems.

10 Claims, 7 Drawing Sheets

SEQUENCE LISTING

```
<160> NUMBER OF SEQ ID NOS: 33

<210> SEQ ID NO 1
<211> LENGTH: 582
<212> TYPE: PRT
<213> ORGANISM: Ustilago maydis

<400> SEQUENCE: 1

Met Trp Gly Arg Ile Arg Asn Val Ile Gln Pro Thr Trp Ala Pro Pro
1               5                   10                  15

Leu Phe Gly Thr Leu Asn Ile Ile Phe Ser Leu Phe Phe Arg Ala Gly
```

```
                 20                  25                  30
Ile Ala Arg Ser His Lys Trp Thr Trp Cys Cys Tyr Arg Pro Thr Arg
             35                  40                  45

Met Ala Arg Ser Arg Thr Phe Ser Asn Ser Ala Pro Thr Arg Arg Arg
 50                  55                  60

Pro Glu Arg Leu Arg Leu Gln Lys Gly Ser Ser Asn Thr Thr Ile Arg
 65                  70                  75                  80

Pro Arg Pro Ser Ala Ile Leu Pro Asp Glu Met Asn His Gly Ser Leu
                 85                  90                  95

Leu Thr Val Val Pro His Thr Val Ala Ser Thr Pro Ser Phe Arg
                100                 105                 110

Ser Ser Phe Pro Asp Ser Leu Ile Ala Ser Val Gln Met Arg Phe Ile
            115                 120                 125

Ala Val Arg Ala Ile Val Thr Leu Ala Ala Ala Ala Val Ser Leu
            130                 135                 140

Ala Val Pro Thr Glu Arg Arg Ala Ala Phe Ala Asp Pro Asn Asp Asp
145                 150                 155                 160

Leu Phe Tyr Thr Thr Pro Asp Asn Ile Asn Thr Tyr Ala Asn Gly Gln
                165                 170                 175

Val Ile Gln Ser Arg Lys Ala Asp Thr Asp Ile Gly Asn Ser Asn Lys
            180                 185                 190

Val Glu Ala Phe Gln Leu Gln Tyr Arg Thr Thr Asn Thr Gln Lys Glu
            195                 200                 205

Ala Gln Ala Asn Val Ala Thr Val Trp Ile Pro Asn Lys Pro Ala Ser
210                 215                 220

Pro Pro Lys Ile Phe Ser Tyr Gln Val Tyr Gln Asp Ser Thr Gln Leu
225                 230                 235                 240

Asn Cys Ala Pro Ser Tyr Ser Phe Leu Lys Gly Leu Asp Lys Pro Asn
                245                 250                 255

Lys Ala Thr Thr Ile Leu Glu Ala Pro Ile Ile Gly Trp Ala Leu
            260                 265                 270

Gln Gln Gly Phe Tyr Val Val Ser Ser Asp His Glu Gly Pro Arg Ser
            275                 280                 285

Ser Phe Ile Ala Gly Tyr Glu Glu Gly Met Ala Ile Leu Asp Gly Ile
290                 295                 300

Arg Ala Leu Lys Asn Tyr Ala Lys Leu Pro Thr Asp Ser Ala Ile Gly
305                 310                 315                 320

Phe Tyr Gly Tyr Ser Gly Gly Ala His Ala Thr Gly Trp Ala Ala Asn
                325                 330                 335

Leu Ala Gly Ser Tyr Ala Pro Glu His Asn Ile Ile Gly Ala Ala Tyr
            340                 345                 350

Gly Gly Leu Pro Ala Ser Ala Arg Asp Thr Phe Asn Phe Leu Asn Lys
            355                 360                 365

Gly Ala Phe Ala Gly Phe Ala Ile Ala Gly Val Ser Gly Leu Ala Leu
            370                 375                 380

Ala Tyr Pro Asp Val Glu Thr Tyr Ile Gln Ser Arg Leu Asn Ala Lys
385                 390                 395                 400

Gly Glu Lys Val Phe Lys Gln Val Arg Ser Arg Gly Phe Cys Ile Gly
                405                 410                 415

Gln Val Val Leu Thr Tyr Pro Phe Val Asp Ala Tyr Ser Leu Ile Asn
            420                 425                 430

Asp Thr Asn Leu Leu Asn Glu Glu Pro Val Ala Ser Thr Leu Lys Ser
            435                 440                 445
```

-continued

```
Glu Thr Leu Val Gln Ala Glu Ala Ser Tyr Thr Val Pro Val Pro Lys
    450                 455                 460

Phe Pro Arg Phe Ile Trp His Ala Leu Leu Asp Glu Ile Val Pro Phe
465                 470                 475                 480

His Ser Ala Ala Thr Tyr Val Lys Glu Gln Cys Ser Lys Gly Ala Asp
                485                 490                 495

Ile Asn Trp Asn Val Tyr Ser Phe Ala Glu His Ile Ser Ala Glu Leu
                500                 505                 510

Phe Gly Leu Leu Pro Gly Leu Asp Trp Leu Asn Lys Ala Tyr Lys Gly
            515                 520                 525

Gln Ala Pro Lys Val Pro Cys Gly Gly Ala Gln Ser Val Met Gly
        530                 535                 540

Ala Ser Gly Pro Pro Ala Gln Asp Val Leu Gly Ala Asp Leu Ala Ser
545                 550                 555                 560

Gln Leu Arg Ser Leu Gln Gly Lys Pro Ser Ala Phe Gly Asn Lys Pro
                565                 570                 575

Phe Gly Ser Ile Ser Pro
            580
```

<210> SEQ ID NO 2
<211> LENGTH: 1749
<212> TYPE: DNA
<213> ORGANISM: Ustilago maydis

<400> SEQUENCE: 2

```
atgtggggc gcatccgcaa cgttattcag ccaacttggg cgccgccgtt atttggcacc      60
ctgaatatca ttttttagcct ttttttccgt gccgggattg caaggtcgca caaatggaca    120
tggtgctgct acagaccgac tcgaatggcc agaagccgca cattctcgaa ttcggctcca    180
accagacggc ggcccgaacg attacggttg cagaagggtt cgtctaatac taccattcgc    240
ccgcgccctt cggctatttt gcctgacgag atgaaccatg ctcgctgct tacgttgtc      300
ccgcacactg tagtcgcctc accccctcc tttcgttctt cctttccaga ttcgttgatc     360
gcctcggttc agatgaggtt cattgctgtt cgggctatcg tgacgctagc ggctgcagcc    420
gccgtgtcgc ttgcagtgcc cacagagcga agggcagcgt tcgccgatcc aaacgacgat    480
ctcttctaca ccacgccgga caacatcaac acatatgcca atggtcaggt catccagtca    540
cgcaaggctg ataccgatat tgggaacagc aacaaggttg aagctttcca gcttcaatat    600
cgcactacca atacgcaaaa ggaggcgcag gccaacgttg ctaccgtatg gatccccaac    660
aagcccgctt cacctcccaa gatcttctct tatcaggtct atcaggactc gacacagctc    720
aactgtgctc cgagctatag cttttttgaag ggccttgaca agcctaacaa agctaccacg    780
atcctcgaag cacccatcat catcggctgg gcgctccaac aaggtttcta cgtcgtctcg     840
tctgatcacg aaggcccgcg ctcatcgttc attgcgggct acgaggaagg tatggctatt     900
ctcgacggca tacgtgcgct caagaactac gccaaactgc ccacgacag cgcgatcggc     960
ttttacggat acagcggcgg tgcccatgca accggctggg cagctaatct ggcagggagc    1020
tacgctcctg agcacaacat catcggtgct gcctacggag gactgcctgc tagcgccaga    1080
gacacattca acttcctcaa caaaggcgcg tttgccggct cgccattgc gggtgtctcg     1140
ggtcttgcgc tggcctaccc ggacgtggaa acctacatcc agtcgcgcct caacgccaag    1200
ggagaaaagg tgtttaaaca ggtccgaagt cgcggcttct gcattggcca agtggtccta    1260
acctacccat tcgtcgacgc ctattcactc atcaacgaca caaaccttct caacgaggaa    1320
```

```
ccggtcgcca gcacgttgaa atccgagacg ttggttcagg ccgaggctag ctacacggtt    1380
cctgttccca aattcccgcg tttcatctgg catgcgctct tggacgagat tgttcccttc    1440
cactcggctg cgacctatgt caaggagcag tgttcaaagg gcgccgacat caactggaat    1500
gtctactcat tgccgagca catctctgcc gagcttttcg gcttgctgcc tggtctcgac     1560
tggttaaaca aggcttacaa gggtcaagca cccaaagtgc cttgtggcgg aggggctcaa    1620
agcgtgatgg gtgcctcagg cccgcctgcg caggacgttc tgggagctga cctggcaagc    1680
caactccgat ctctccaggg taagccttct gcgtttggca acaaaccttt tggctccatc    1740
tcccctga                                                             1749
```

<210> SEQ ID NO 3
<211> LENGTH: 462
<212> TYPE: PRT
<213> ORGANISM: Candida antarctica

<400> SEQUENCE: 3

```
Met Arg Val Ser Leu Arg Ser Ile Thr Ser Leu Ala Ala Ala Thr
 1               5                  10                  15

Ala Ala Val Leu Ala Ala Pro Ala Glu Thr Leu Asp Arg Arg Ala
                20                  25                  30

Ala Leu Pro Asn Pro Tyr Asp Asp Pro Phe Tyr Thr Thr Pro Ser Asn
            35                  40                  45

Ile Gly Thr Phe Ala Lys Gly Gln Val Ile Gln Ser Arg Lys Val Pro
         50                  55                  60

Thr Asp Ile Gly Asn Ala Asn Asn Ala Ala Ser Phe Gln Leu Gln Tyr
 65                  70                  75                  80

Arg Thr Thr Asn Thr Gln Asn Glu Ala Val Ala Asp Val Ala Thr Val
                 85                  90                  95

Trp Ile Pro Ala Lys Pro Ala Ser Pro Pro Lys Ile Phe Ser Tyr Gln
            100                 105                 110

Val Tyr Glu Asp Ala Thr Ala Leu Asp Cys Ala Pro Ser Tyr Ser Tyr
        115                 120                 125

Leu Thr Gly Leu Asp Gln Pro Asn Lys Val Thr Ala Val Leu Asp Thr
    130                 135                 140

Pro Ile Ile Ile Gly Trp Ala Leu Gln Gln Gly Tyr Tyr Val Val Ser
145                 150                 155                 160

Ser Asp His Glu Gly Phe Lys Ala Ala Phe Ile Ala Gly Tyr Glu Glu
                165                 170                 175

Gly Met Ala Ile Leu Asp Gly Ile Arg Ala Leu Lys Asn Tyr Gln Asn
            180                 185                 190

Leu Pro Ser Asp Ser Lys Val Ala Leu Glu Gly Tyr Ser Gly Gly Ala
        195                 200                 205

His Ala Thr Val Trp Ala Thr Ser Leu Ala Glu Ser Tyr Ala Pro Glu
    210                 215                 220

Leu Asn Ile Val Gly Ala Ser His Gly Gly Thr Pro Val Ser Ala Lys
225                 230                 235                 240

Asp Thr Phe Thr Phe Leu Asn Gly Gly Pro Phe Ala Gly Phe Ala Leu
                245                 250                 255

Ala Gly Val Ser Gly Leu Ser Leu Ala His Pro Asp Met Glu Ser Phe
            260                 265                 270

Ile Glu Ala Arg Leu Asn Ala Lys Gly Gln Arg Thr Leu Lys Gln Ile
        275                 280                 285
```

Arg Gly Arg Gly Phe Cys Leu Pro Gln Val Val Leu Thr Tyr Pro Phe
        290             295                 300

Leu Asn Val Phe Ser Leu Val Asn Asp Thr Asn Leu Leu Asn Glu Ala
305                 310                 315                 320

Pro Ile Ala Ser Ile Leu Lys Gln Glu Thr Val Val Gln Ala Glu Ala
                325                 330                 335

Ser Tyr Thr Val Ser Val Pro Lys Phe Pro Arg Phe Ile Trp His Ala
                340                 345                 350

Ile Pro Asp Glu Ile Val Pro Tyr Gln Pro Ala Ala Thr Tyr Val Lys
            355                 360                 365

Glu Gln Cys Ala Lys Gly Ala Asn Ile Asn Phe Ser Pro Tyr Pro Ile
370                 375                 380

Ala Glu His Leu Thr Ala Glu Ile Phe Gly Leu Val Pro Ser Leu Trp
385                 390                 395                 400

Phe Ile Lys Gln Ala Phe Asp Gly Thr Thr Pro Lys Val Ile Cys Gly
                405                 410                 415

Thr Pro Ile Pro Ala Ile Ala Gly Ile Thr Thr Pro Ser Ala Asp Gln
                420                 425                 430

Val Leu Gly Ser Asp Leu Ala Asn Gln Leu Arg Ser Leu Asp Gly Lys
                435                 440                 445

Gln Ser Ala Phe Gly Lys Pro Phe Gly Pro Ile Thr Pro Pro
450                 455                 460

<210> SEQ ID NO 4
<211> LENGTH: 458
<212> TYPE: PRT
<213> ORGANISM: Ustilago maydis

<400> SEQUENCE: 4

Met Arg Phe Ile Ala Val Arg Ala Ile Val Thr Leu Ala Ala Ala Ala
1               5                   10                  15

Ala Val Ser Leu Ala Val Pro Thr Glu Arg Arg Ala Phe Ala Asp
                20                  25                  30

Pro Asn Asp Asp Leu Phe Tyr Thr Thr Pro Asp Asn Ile Asn Thr Tyr
            35                  40                  45

Ala Asn Gly Gln Val Ile Gln Ser Arg Lys Ala Asp Thr Asp Ile Gly
50                  55                  60

Asn Ser Asn Lys Val Glu Ala Phe Gln Leu Gln Tyr Arg Thr Thr Asn
65                  70                  75                  80

Thr Gln Lys Glu Ala Gln Ala Asn Val Ala Thr Val Trp Ile Pro Asn
                85                  90                  95

Lys Pro Ala Ser Pro Lys Ile Phe Ser Tyr Gln Val Tyr Gln Asp
            100                 105                 110

Ser Thr Gln Leu Asn Cys Ala Pro Ser Tyr Ser Phe Leu Lys Gly Leu
                115                 120                 125

Asp Lys Pro Asn Lys Ala Thr Thr Ile Leu Glu Ala Pro Ile Ile Ile
130                 135                 140

Gly Trp Ala Leu Gln Gln Gly Phe Tyr Val Val Ser Ser Asp His Glu
145                 150                 155                 160

Gly Pro Arg Ser Ser Phe Ile Ala Gly Tyr Glu Glu Gly Met Ala Ile
                165                 170                 175

Leu Asp Gly Ile Arg Ala Leu Lys Asn Tyr Ala Lys Leu Pro Thr Asp
            180                 185                 190

Ser Ala Ile Gly Phe Tyr Gly Tyr Ser Gly Gly Ala His Ala Thr Gly
            195                 200                 205

```
Trp Ala Ala Asn Leu Ala Gly Ser Tyr Ala Pro Glu His Asn Ile Ile
    210                 215                 220
Gly Ala Ala Tyr Gly Gly Leu Pro Ala Ser Ala Arg Asp Thr Phe Asn
225                 230                 235                 240
Phe Leu Asn Lys Gly Ala Phe Gly Phe Ala Ile Ala Gly Val Ser
            245                 250                 255
Gly Leu Ala Leu Ala Tyr Pro Asp Val Glu Thr Tyr Ile Gln Ser Arg
            260                 265                 270
Leu Asn Ala Lys Gly Glu Lys Val Phe Lys Gln Val Arg Ser Arg Gly
        275                 280                 285
Phe Cys Ile Gly Gln Val Val Leu Thr Tyr Pro Phe Val Asp Ala Tyr
        290                 295                 300
Ser Leu Ile Asn Asp Thr Asn Leu Leu Asn Glu Glu Pro Val Ala Ser
305                 310                 315                 320
Thr Leu Lys Ser Glu Thr Leu Val Gln Ala Glu Ala Ser Tyr Thr Val
            325                 330                 335
Pro Val Pro Lys Phe Pro Arg Phe Ile Trp His Ala Leu Leu Asp Glu
            340                 345                 350
Ile Val Pro Phe His Ser Ala Ala Thr Tyr Val Lys Glu Gln Cys Ser
        355                 360                 365
Lys Gly Ala Asp Ile Asn Trp Asn Val Tyr Ser Phe Ala Glu His Ile
    370                 375                 380
Ser Ala Glu Leu Phe Gly Leu Leu Pro Gly Leu Asp Trp Leu Asn Lys
385                 390                 395                 400
Ala Tyr Lys Gly Gln Ala Pro Lys Val Pro Cys Gly Gly Gly Ala Gln
            405                 410                 415
Ser Val Met Gly Ala Ser Gly Pro Pro Ala Gln Asp Val Leu Gly Ala
            420                 425                 430
Asp Leu Ala Ser Gln Leu Arg Ser Leu Gln Gly Lys Pro Ser Ala Phe
        435                 440                 445
Gly Asn Lys Pro Phe Gly Ser Ile Ser Pro
    450                 455

<210> SEQ ID NO 5
<211> LENGTH: 1377
<212> TYPE: DNA
<213> ORGANISM: Ustilago maydis

<400> SEQUENCE: 5
atgaggttca ttgctgttcg ggctatcgtg acgctagcgg ctgcagccgc cgtgtcgctt      60
gcagtgccca cagagcgaag ggcagcgttc gccgatccaa cgacgatct  cttctacacc     120 acgccggaca acatcaacac atatgccaat ggtcaggtca tccagtcacg caaggctgat     180
accgatattg gaacagcaa  caaggttgaa gctttccagc ttcaatatcg cactaccaat     240
acgcaaaagg aggcgcaggc caacgttgct accgtatgga tccccaacaa gcccgcttca     300
cctcccaaga tcttctctta tcaggtctat caggactcga cacagctcaa ctgtgctccg     360
agctatagct ttttgaaggg ccttgacaag cctaacaaag ctaccacgat cctcgaagca     420
cccatcatca tcggctgggc gctccaacaa ggtttctacg tcgtctcgtc tgatcacgaa     480
ggcccgcgct catcgttcat tgcgggctac gaggaaggta tggctattct cgacggcata     540
cgtgcgctca agaactacgc caaactgccc acgacagcg  cgatcggctt ttacggatac     600
agcggcggtg cccatgcaac cggctgggca gctaatctgg cagggagcta cgctcctgag     660
```

```
cacaacatca tcggtgctgc ctacggagga ctgcctgcta gcgccagaga cacattcaac    720
ttcctcaaca aggcgcgtt tgccggcttc gccattgcgg tgtctcggg tcttgcgctg    780 gcctacccgg acgtggagac ctacatccag tcgcgcctca cgccaaggg agaaaaggtg    840 tttaaacagg tccgaagtcg cggcttctgc attggccaag tggtcctaac ctacccattc    900
gtcgacgcct attcactcat caacgacaca aaccttctca cgaggaacc ggtcgccagc    960 acgttgaaat ccgagacgtt ggttcaggcc gaggctagct acacggttcc tgttcccaaa   1020
ttcccgcgtt tcatctggca tgcgctcttg gacgagattg ttcccttcca ctcggctgcg   1080
acctatgtca aggagcagtg ttcaaagggc gccgacatca actggaatgt ctactcattt   1140
gccgagcaca tctctgccga gcttttcggc ttgctgcctg gtctcgactg gttaaacaag   1200
gcttacaagg tcaagcacc caaagtgcct tgtggcggag gggctcaaag cgtgatgggt   1260
gcctcaggcc cgcctgcgca ggacgttctg ggagctgacc tggcaagcca actccgatct   1320
ctccagggta agccttctgc gtttggcaac aaaccttttg gctccatctc cccctga      1377
```

```
<210> SEQ ID NO 6
<211> LENGTH: 437
<212> TYPE: PRT
<213> ORGANISM: Ustilago maydis

<400> SEQUENCE: 6
```

```
Met Val Pro Thr Glu Arg Arg Ala Ala Phe Ala Asp Pro Asn Asp Asp
1               5                   10                  15

Leu Phe Tyr Thr Thr Pro Asp Asn Ile Asn Thr Tyr Ala Asn Gly Gln
            20                  25                  30

Val Ile Gln Ser Arg Lys Ala Asp Thr Asp Ile Gly Asn Ser Asn Lys
        35                  40                  45

Val Glu Ala Phe Gln Leu Gln Tyr Arg Thr Thr Asn Thr Gln Lys Glu
    50                  55                  60

Ala Gln Ala Asn Val Ala Thr Val Trp Ile Pro Asn Lys Pro Ala Ser
65                  70                  75                  80

Pro Pro Lys Ile Phe Ser Tyr Gln Val Tyr Gln Asp Ser Thr Gln Leu
                85                  90                  95

Asn Cys Ala Pro Ser Tyr Ser Phe Leu Lys Gly Leu Asp Lys Pro Asn
            100                 105                 110

Lys Ala Thr Thr Ile Leu Glu Ala Pro Ile Ile Gly Trp Ala Leu
        115                 120                 125

Gln Gln Gly Phe Tyr Val Val Ser Ser Asp His Glu Gly Pro Arg Ser
    130                 135                 140

Ser Phe Ile Ala Gly Tyr Glu Glu Gly Met Ala Ile Leu Asp Gly Ile
145                 150                 155                 160

Arg Ala Leu Lys Asn Tyr Ala Lys Leu Pro Thr Asp Ser Ala Ile Gly
                165                 170                 175

Phe Tyr Gly Tyr Ser Gly Gly Ala His Ala Thr Gly Trp Ala Ala Asn
            180                 185                 190

Leu Ala Gly Ser Tyr Ala Pro Glu His Asn Ile Ile Gly Ala Ala Tyr
        195                 200                 205

Gly Gly Leu Pro Ala Ser Ala Arg Asp Thr Phe Asn Phe Leu Asn Lys
    210                 215                 220

Gly Ala Phe Ala Gly Phe Ala Ile Ala Gly Val Ser Gly Leu Ala Leu
225                 230                 235                 240

Ala Tyr Pro Asp Val Glu Thr Tyr Ile Gln Ser Arg Leu Asn Ala Lys
                245                 250                 255
```

```
Gly Lys Val Phe Lys Gln Val Arg Ser Arg Gly Phe Cys Ile Gly
        260                 265                 270

Gln Val Val Leu Thr Tyr Pro Phe Val Asp Ala Tyr Ser Leu Ile Asn
        275                 280                 285

Asp Thr Asn Leu Leu Asn Glu Glu Pro Val Ala Ser Thr Leu Lys Ser
        290                 295                 300

Glu Thr Leu Val Gln Ala Glu Ala Ser Tyr Thr Val Pro Val Pro Lys
305                 310                 315                 320

Phe Pro Arg Phe Ile Trp His Ala Leu Leu Asp Glu Ile Val Pro Phe
                325                 330                 335

His Ser Ala Ala Thr Tyr Val Lys Glu Gln Cys Ser Lys Gly Ala Asp
                340                 345                 350

Ile Asn Trp Asn Val Tyr Ser Phe Ala Glu His Ile Ser Ala Glu Leu
                355                 360                 365

Phe Gly Leu Leu Pro Gly Leu Asp Trp Leu Asn Lys Ala Tyr Lys Gly
            370                 375                 380

Gln Ala Pro Lys Val Pro Cys Gly Gly Ala Gln Ser Val Met Gly
385                 390                 395                 400

Ala Ser Gly Pro Pro Ala Gln Asp Val Leu Gly Ala Asp Leu Ala Ser
                405                 410                 415

Gln Leu Arg Leu Gln Gly Lys Pro Ser Ala Phe Gly Asn Lys Pro Phe
                420                 425                 430

Gly Ser Ile Ser Pro
        435
```

<210> SEQ ID NO 7
<211> LENGTH: 1389
<212> TYPE: DNA
<213> ORGANISM: Artificial Sequence
<220> FEATURE:
<223> OTHER INFORMATION: Codon optimized, histidine tagged, full length
      CAL-A sequence

<400> SEQUENCE: 7

```
atgcgtgtga gcctgcgtag cattaccagc ctgctggctg cggcaaccgc agcagttctg      60
gctgcgccgg cagcggaaac cctggatcgt cgtgcggcgc tgccgaatcc gtatgatgat    120
ccgtttttata ccaccccgag caacattggc acctttgcga aaggccaggt gattcagagc    180
cgtaaagtgc cgaccgatat tggcaacgcg aacaacgcgg cgagctttca gctgcaatat    240
cgtaccacca cacccagaa cgaagcggtg cggatgtgg cgaccgtgtg gattccggcg    300
aaaccggcga gcccgccgaa attttttagc taccaggtgt atgaagatgc gaccgcgctg    360
gattgcgcgc cgagctatag ctatctgacc ggcctggatc agccgaacaa agtgaccgcg    420
gtgctggata ccccgattat tattggctgg cgctgcaac agggctatta tgtggtgagc    480
agcgatcatg aaggctttaa gcggcgtttt attgcgggct atgaagaagg catggcgatt    540
ctggatggca ttcgtgcgct gaaaaactat cagaacctgc cgagcgatag caaagtggcg    600
ctggaaggct atagcggcgg tgcgcacgcg accgtttggg cgaccagcct ggccgaaagc    660
tatgcgccgg aactgaacat tgtgggcgcg agtcatggtg caccccggt gagcgcgaaa    720
gataccttta ccttctctgaa cggcggtccg tttgcgggtt ttgcgctggc cggtgtgagc    780
ggtctgagcc tggcccatcc ggatatggaa agctttattg aagcgcgtct gaacgcgaaa    840
ggtcagcgta ccctgaaaca aattcgtggc cgtggctttt gcctgccgca ggtggtgctg    900
acctatccgt ttctgaacgt gtttagcctg gtgaacgata ccaacctgct gaacgaagcg    960
```

```
ccgattgcga gcattctgaa acaggaaacc gttgttcagg cggaagcgag ctataccgtg    1020
agcgtgccga aatttccgcg ttttatttgg catgcgattc cggatgaaat tgtgccgtat    1080
cagccggcag cgacctatgt gaaagaacag tgcgcgaaag cgcgaacat  taactttagc    1140 ccgtatccga ttgcggaaca tctgaccgcg gaaattttg  gcctggtgcc gagcctgtgg    1200
tttattaaac aggcgtttga tggcaccacc ccgaaagtga tttgcggcac cccgattccg    1260
gcgattgcgg gcattaccac cccgtctgcg gatcaggtgc tgggcagcga tctgccaac   1320 cagctgcgta gcctggatgg caaacagagc gcgtttggca aaccgtttgg cccgattacc    1380
ccgccgtaa                                                            1389

<210> SEQ ID NO 8
<211> LENGTH: 25
<212> TYPE: DNA
<213> ORGANISM: Artificial Sequence
<220> FEATURE:
<223> OTHER INFORMATION: Forward CAL-A primer

<400> SEQUENCE: 8
taaggtacca tatgcgtgtg agcct                                            25

<210> SEQ ID NO 9
<211> LENGTH: 33
<212> TYPE: DNA
<213> ORGANISM: Artificial Sequence
<220> FEATURE:
<223> OTHER INFORMATION: Reverse CAL-A primer

<400> SEQUENCE: 9
taagaatgcg gccgccggcg gggtaatcgg gcc                                   33

<210> SEQ ID NO 10
<211> LENGTH: 1782
<212> TYPE: DNA
<213> ORGANISM: Artificial Sequence
<220> FEATURE:
<223> OTHER INFORMATION: codon-optimized LipUMf sequence

<400> SEQUENCE: 10
atgtggggtc gtattcgtaa tgttattcag ccgacctggg cacctccgct gtttggcacc     60
ctgaatatta ttttttagcct gttttttcgt gcaggtattg cacgtagcca taaatggacc   120
tggtgttgtt atcgtccgac ccgtatggca cgtagccgta cctttagcaa tagcgcaccg   180
acccgtcgtc gtccggaacg tctgcgtctg cagaaaggta gcagcaatac caccattcgt   240
ccgcgtccga gcgcaattct gccggatgaa atgaatcatg gtagcctgct gaccgttgtt   300
ccgcataccc ttgttgcaag cacccccgagc tttcgtagca gctttccgga tagcctgatt   360
gcaagcgttc agatgcgttt tattgcagtt cgtgccattg ttaccctggc agcagcagca   420
gccgttagcc tggcagttcc gaccgaacgt cgtgcagcat ttgcagatcc gaatgatgac   480
ctgttctata ccacaccgga taacatcaac acctatgcca atggccaggt tattcagagc   540
cgtaaagccg ataccgatat tggcaatagc aataaagtgg aagcatttca gctgcagtat   600
cgtaccacca ataccccagaa agaagcacag gccaacgttg caaccgtttg gattccgaat   660
aaaccggcat ctcctccgaa aatttttagc tatcaggtgt atcaggatag cacccagctg   720
aattgtgcac cgagctatag ctttctgaaa ggtctggata aaccgaataa agcaaccacc   780
attctggaag caccgattat tattggttgg gcactgcagc agggttttta tgttgttagc   840
```

| | |
|---|---|
| agcgatcatg aaggtccgcg tagctctttt attgccggtt atgaagaagg tatggccatt | 900 |
| ctggatggta ttcgtgccct gaaaaattat gcaaaactgc cgaccgatag cgcaattggt | 960 |
| ttttatggtt atagcggtgg tgcacatgca accggttggg cagcaaatct ggcaggtagc | 1020 |
| tatgcaccgg aacataatat tattggtgca gcctatggtg gtctgcctgc aagcgcacgt | 1080 |
| gataccttta attttctgaa taaaggtgcc tttgcaggtt ttgcaattgc cggtgttagc | 1140 |
| ggtctggcac tggcatatcc ggatgtggaa acctatattc agtctcgcct gaatgcaaaa | 1200 |
| ggcgaaaaag tgtttaaaca ggttcgtagc cgtggttttt gtattggtca ggtggttctg | 1260 |
| acctatccgt tgttgatgc ctatagcctg attaatgata ccaatctgct gaatgaagaa | 1320 |
| ccggttgcca gcaccctgaa agcgaaaccc ctggttcagg cagaagcaag ctataccgtt | 1380 |
| ccggttccga aatttccgcg ttttatttgg catgcactgc tggatgaaat tgttccgttt | 1440 |
| catagcgcag caacctatgt aaagaacag tgtagcaaag gtgccgatat taattggaat | 1500 |
| gtgtatagct tgccgaaca tattagcgca gaactgtttg gtctgctgcc tggtctggat | 1560 |
| tggctgaata aagcctataa aggtcaggca ccgaaagttc cgtgtggtgg tggtgcacag | 1620 |
| agcgttatgg gtgcaagcgg tcctccggca caggatgttc tgggtgcaga tctggcaagc | 1680 |
| cagctgcgta gcctgcaggg taaaccgagc gcatttggca taaaccgtt tggtagcatt | 1740 |
| tctcctgcgg ccgcactcga gcaccaccac caccaccact ga | 1782 |

<210> SEQ ID NO 11
<211> LENGTH: 1410
<212> TYPE: DNA
<213> ORGANISM: Artificial Sequence
<220> FEATURE:
<223> OTHER INFORMATION: codon-optimized LipUMs sequence

<400> SEQUENCE: 11

| | |
|---|---|
| atgcgtttta ttgccgttcg tgcaattgtt accctggctg cagcagcagc agttagcctg | 60 |
| gccgttccga ccgaacgtcg tgcagcattt gcagatccga tgacgacct gttttatacc | 120 |
| acaccggata acatcaatac ctatgcgaat ggtcaggtta ttcagagccg taaagccgat | 180 |
| accgatattg caatagcaa taaagtggaa gcatttcagc tgcagtatcg taccaccaat | 240 |
| acccagaaag aagcacaggc aaacgtcgca acagtttgga ttccgaataa accggcaagc | 300 |
| cctccgaaaa ttttagcta tcaggtgtat caggatagca cccagctgaa ttgtgcaccg | 360 |
| agctatagct ttctgaaagg tctggataaa ccgaataaag caaccaccat tctggaagca | 420 |
| ccgattatta ttggttgggc actgcagcag ggtttttatg ttgttagcag cgatcatgaa | 480 |
| ggtccgcgta gcagctttat tgcaggttat gaagaaggta tggccattct ggatggtatt | 540 |
| cgtgccctga aaattatgc aaaactgccg accgatagcg caattggttt ttatggttat | 600 |
| agcggtggtg cacatgcaac cggttgggca gcaaatctgg ctggtagcta tgcaccggaa | 660 |
| cataatatta ttggtgcagc ctatggtggt ctgcctgcca gcgcacgtga taccttaat | 720 |
| tttctgaata aaggtgcctt tgcaggtttt gcaattgcag tgttagcgg tctggccctg | 780 |
| gcctatccgg atgttgaaac ctatattcag tctcgcctga atgcaaaagg cgaaaaagtg | 840 |
| tttaaacagg ttcgtagccg tggttttgt attggtcagg tggttctgac ctatcctttt | 900 |
| gttgatgcct atagcctgat taatgatacc aatctgctga atgaagaacc ggttgcaagc | 960 |
| accctgaaaa gcgaaaccct ggttcaggca gaagcaagct ataccgttcc ggttccgaaa | 1020 |
| tttccgcgtt tatttggca tgcactgctg atgaaattg ttccgtttca tagcgcagca | 1080 |
| acctatgtta agaacagtg ctctaaaggt gccgatatta ttggaatgt gtatagcttt | 1140 |

```
gccgaacata ttagcgcaga gctgtttggt ctgctgcctg gtctggattg gctgaataaa    1200
gcctataaag gtcaggcacc gaaagttccg tgtggtggtg gtgcacagag cgttatgggt    1260
gcaagcggtc ctccggcaca ggatgttctg ggtgcagatc tggccagcca gctgcgtagc    1320
ctgcagggta aaccgagcgc atttggcaat aaaccgtttg gtagcatttc tcctgcggcc    1380
gcactcgagc accaccacca ccaccactga                                     1410
```

<210> SEQ ID NO 12
<211> LENGTH: 1830
<212> TYPE: DNA
<213> ORGANISM: Artificial Sequence
<220> FEATURE:
<223> OTHER INFORMATION: codon-optimized LipUMf sequence for cloning
      into P. pastoris

<400> SEQUENCE: 12

```
atgtggggcc gtatccgtaa tgtcatccag cctacctggg caccgccttt gtttggcacc      60
ctgaatatca tctttagcct gttctttcgt gcgggtattg ctagatctca taagtggact     120
tggtgttgct atagaccaac acgcatggcg cgctcccgta cgtttagcaa cagtgctcca     180
acccgtagac gcccggaaag actgcgcttg cagaaaggat cttccaacac cactatccgt     240
ccgagacctt ctgccattct gcctgatgaa atgaatcatg ttccctgtt gaccgttgtg      300 ccacacactg tcgttgcgtc aacacctagc tttagatcaa gctcccccaga tagttttgatt    360 gcttctgttc aaatgcgctt tatcgccgtt cgtgcaattg ttaccctggc tgccgcagcg    420
gctgtctcct ggcggttcc aaccgaacgt agagccgcat tgctgatcc gaacgatgac    480 ctgttctata caacgcctga caacatcaat acgtacgcca atggccaggt cattcaatcc    540
cgtaaggcag ataccgacat cggaaaactca acaaagtgg aagcttttca gctgcaatac    600
agaaccacta atactcagaa ggaggcccaa gcaaacgtgg ccacagtctg gattcctaat    660
aagccagcat ctccaccgaa aatcttttcc tatcaggttt accaagattc tactcagctg    720
aactgtgccc gtcttattc cttcctgaaa ggtttggaca aaccaaataa ggcgacaacg    780
attctggaag ctccgattat cattggttgg cattgcagc aaggcttta cgtggtcagt    840 tctgatcatg agggtccgag atcctcattc attgccggct atgaagaggg aatggcaatc    900
ttggatggca ttcgcgcgct gaagaactac gctaaattgc ctactgacag tgccattggc    960
ttttatggat actctggtgg cgcgcatgct acaggatggg cggctaacct ggccggttca    1020
tatgcaccgg aacacaatat cattggtgct gcatatggag gtctgcctgc aagcgcacgc   1080
gatactttta acttcttgaa caaaggagcg tttgctggct cgccattgc tggtgtgtca    1140 ggcctggcgt tggcttatcc tgacgtcgaa acctacatcc aaagccgtct gaatgctaaa    1200
ggagagaagg tgtttaaaca ggtccgcagt cgtggattct gcattggtca agttgtgctg    1260
acttatcctt tgttgatgc ctactctttg atcaacgaca caaatctgtt gaacgaagag    1320
ccagttgcat ccacgttgaa gtcagaaacc ctggtgcagg ccgaggcatc ttatactgtc    1380
ccagttccga atttccacg tttcatctgg catgcgctgt ggatgaaat tgttccgttc    1440 cacagcgcgg ctacctatgt gaaggagcaa tgtagtaaag gtgctgacat taactggaat    1500
gtttactcat ttgccgaaca catcagcgca gagctgttcg gcctgttgcc gggactggat    1560
tggttgaata aggcgtacaa aggccaggct ccgaaagtcc cttgcggcgg aggtgctcaa    1620
agcgttatgg gagccagtgg tcctccagca caggatgtgc tgggtgcgga cttgcttct    1680 caactgcgta gcctgcaagg taaaccatca gcattcggta caaaaccatt cggaagtatc   1740
```
tccccggcgg ccgccagctt tctagaacaa aaactcatct cagaagagga tctgaatagc     1800
gccgtcgacc atcatcatca tcatcattga                                    1830

<210> SEQ ID NO 13
<211> LENGTH: 1458
<212> TYPE: DNA
<213> ORGANISM: Artificial Sequence
<220> FEATURE:
<223> OTHER INFORMATION: codon-optimized LipUMs sequence for cloning
      into P. pastoris

<400> SEQUENCE: 13
atgcgcttca tcgctgtgcg tgctattgtc actttggcgg cggcggcggc ggtgtcattg       60
gcagtcccta cggaacgtcg tgcggctttt gctgatccga acgatgacct gttctatacc      120
actcctgaca acatcaatac ctacgcaaat ggccaggtta ttcaatccag aaaggcggat      180
actgacatcg aaactcaaa caaagtggaa gcctttcagt tgcaatatcg cacaacgaat      240
acccagaagg aggcacaagc gaacgttgct actgtgtgga ttccaaataa gccggcctct      300
ccaccgaaaa tcttttccta tcaggtttac caagattcta cccagctgaa ctgtgcacca      360
agttattctt tcctgaaagg tttggacaaa ccaaataagg ctaccactat tctggaagcc      420
ccgattatca ttggttgggc cttgcagcaa ggcttttacg ttgtgtcttc cgatcatgaa      480
ggccctcgct caagcttcat tgcaggctat gaagagggaa tggcgatctt ggatggtatt      540
cgtgctctga gaactacgc caaattgcca acagacagtg ctattggctt ttatggatac      600
tctggtggcg ctcatgcaac cggatgggct gcaaacctgg caggtagcta tgcgcctgaa      660
cacaatatca ttggtgcagc gtacggaggt ctgccagcaa gtgcgcgtga taccttaac      720 ttcttgaaca aggtgctttt gccggcttc gcaattgcgg tgtctctgg cctggctttg      780 gcctatccgg atgttgaaac ttacatccaa tccagactga atgccaaagg agagaaggtc      840
tttaaacagt tcgttcaag aggattctgc attggtcaag tcgttctgac atatccattt      900
gttgatgctt actccttgat caacgacacg aatctgttga acgaagagcc ggtggcctcc      960
acattgaagt cagaaacgct ggtccaggca gaggcgtcat atactgtgcc ggtccctaaa     1020
tttccgcgtt tcatctggca tgcactgttg gatgaaattg tgcctttcca cagcgctgcc     1080
acatatgtca aggagcaatg tagtaagggt gcggacatta actggaatgt ctactcattt     1140
gcagaacaca tcagcgcgga gctgttcggc ctgttgcctg actggattg gttgaacaag     1200 gcttacaaag gccaggcccc taaagttcca tgcggcggag gtgctcaaag cgtgatggga     1260
gcaagtggtc ctccagcgca ggatgtgctg ggtgctgact tggcctctca actgcgtagc     1320
ctgcaaggta aaccatccgc attcggtaac aagccattcg gtagcatctc accagcggcc     1380
gccagctttc tagaacaaaa actcatctca gaagaggatc tgaatagcgc cgtcgaccat     1440
catcatcatc atcattga                                                 1458

<210> SEQ ID NO 14
<211> LENGTH: 23
<212> TYPE: DNA
<213> ORGANISM: Artificial Sequence
<220> FEATURE:
<223> OTHER INFORMATION: forward primer for F145D point mutation

<400> SEQUENCE: 14
gctcaagcga cattgcaggc tat                                              23

```
<210> SEQ ID NO 15
<211> LENGTH: 23
<212> TYPE: DNA
<213> ORGANISM: Artificial Sequence
<220> FEATURE:
<223> OTHER INFORMATION: reverse primer for F145D point mutation

<400> SEQUENCE: 15
gggagcgagt tcgctgtaac gtc                                    23

<210> SEQ ID NO 16
<211> LENGTH: 25
<212> TYPE: DNA
<213> ORGANISM: Artificial Sequence
<220> FEATURE:
<223> OTHER INFORMATION: forward primer for A214N point mutation

<400> SEQUENCE: 16
cagcaagtaa ccgtgatacc tttaa                                  25

<210> SEQ ID NO 17
<211> LENGTH: 24
<212> TYPE: DNA
<213> ORGANISM: Artificial Sequence
<220> FEATURE:
<223> OTHER INFORMATION: reverse primer for A214N mutation

<400> SEQUENCE: 17
agacggtcgt tcattggcac tatg                                   24

<210> SEQ ID NO 18
<211> LENGTH: 24
<212> TYPE: DNA
<213> ORGANISM: Artificial Sequence
<220> FEATURE:
<223> OTHER INFORMATION: forward primer for T217H point mutation

<400> SEQUENCE: 18
gcgtgatcat tttaacttct tgaa                                   24

<210> SEQ ID NO 19
<211> LENGTH: 26
<212> TYPE: DNA
<213> ORGANISM: Artificial Sequence
<220> FEATURE:
<223> OTHER INFORMATION: reverse primer for T217H point mutation

<400> SEQUENCE: 19
gttcacgcgc actagtaaaa ttgaag                                 26

<210> SEQ ID NO 20
<211> LENGTH: 23
<212> TYPE: DNA
<213> ORGANISM: Artificial Sequence
<220> FEATURE:
<223> OTHER INFORMATION: forward primer for F218S point mutation

<400> SEQUENCE: 20
gatacctcga acttcttgaa caa                                    23

<210> SEQ ID NO 21
<211> LENGTH: 21
<212> TYPE: DNA
<213> ORGANISM: Artificial Sequence
<220> FEATURE:
<223> OTHER INFORMATION: reverse primer for F218S point mutation
```

<400> SEQUENCE: 21
cgcgcactat ggagcttgaa g                                        21

<210> SEQ ID NO 22
<211> LENGTH: 22
<212> TYPE: DNA
<213> ORGANISM: Artificial Sequence
<220> FEATURE:
<223> OTHER INFORMATION: forward primer for V297H point mutation

<400> SEQUENCE: 22
gagccgcacg cctccacatt ga                                       22

<210> SEQ ID NO 23
<211> LENGTH: 24
<212> TYPE: DNA
<213> ORGANISM: Artificial Sequence
<220> FEATURE:
<223> OTHER INFORMATION: reverse primer for V297H point mutation

<400> SEQUENCE: 23
cttgcttctc ggcgtgcgga ggtg                                     24

<210> SEQ ID NO 24
<211> LENGTH: 24
<212> TYPE: DNA
<213> ORGANISM: Artificial Sequence
<220> FEATURE:
<223> OTHER INFORMATION: forward primer for L301N point mutation

<400> SEQUENCE: 24
ctccacaaac aagtcagaaa cgct                                     24

<210> SEQ ID NO 25
<211> LENGTH: 24
<212> TYPE: DNA
<213> ORGANISM: Artificial Sequence
<220> FEATURE:
<223> OTHER INFORMATION: reverse primer for L301N point mutation

<400> SEQUENCE: 25
gccaccggag gtgtttgttc agtc                                     24

<210> SEQ ID NO 26
<211> LENGTH: 22
<212> TYPE: DNA
<213> ORGANISM: Artificial Sequence
<220> FEATURE:
<223> OTHER INFORMATION: forward primer for G233A point mutation

<400> SEQUENCE: 26
attgcggctg tctctggcct gg                                       22

<210> SEQ ID NO 27
<211> LENGTH: 22
<212> TYPE: DNA
<213> ORGANISM: Artificial Sequence
<220> FEATURE:
<223> OTHER INFORMATION: reverse primer for G233A point mutation

<400> SEQUENCE: 27
gaagcgttaa cgccgacaga ga                                       22

<210> SEQ ID NO 28
<211> LENGTH: 27

```
<212> TYPE: DNA
<213> ORGANISM: Artificial Sequence
<220> FEATURE:
<223> OTHER INFORMATION: forward primer for G233Y point mutation

<400> SEQUENCE: 28
caattgcgta tgtctctggc ctggctt                                          27

<210> SEQ ID NO 29
<211> LENGTH: 27
<212> TYPE: DNA
<213> ORGANISM: Artificial Sequence
<220> FEATURE:
<223> OTHER INFORMATION: reverse primer for G233Y point mutation

<400> SEQUENCE: 29
ggccgaagcg ttaacgcata cagagac                                          27

<210> SEQ ID NO 30
<211> LENGTH: 22
<212> TYPE: DNA
<213> ORGANISM: Artificial Sequence
<220> FEATURE:
<223> OTHER INFORMATION: forward primer for G233L point mutation

<400> SEQUENCE: 30
attgcgcttg tctctggcct gg                                               22

<210> SEQ ID NO 31
<211> LENGTH: 23
<212> TYPE: DNA
<213> ORGANISM: Artificial Sequence
<220> FEATURE:
<223> OTHER INFORMATION: reverse primer for G233L point mutation

<400> SEQUENCE: 31
cgaagcgtta acgcgaacag aga                                              23

<210> SEQ ID NO 32
<211> LENGTH: 9
<212> TYPE: PRT
<213> ORGANISM: Artificial Sequence
<220> FEATURE:
<223> OTHER INFORMATION: C-terminal flap sequence of LipUMf

<400> SEQUENCE: 32

Pro Val Ala Ser Thr Leu Lys Ser Glu
1               5

<210> SEQ ID NO 33
<211> LENGTH: 9
<212> TYPE: PRT
<213> ORGANISM: Artificial Sequence
<220> FEATURE:
<223> OTHER INFORMATION: C-terminal flap sequence

<400> SEQUENCE: 33

Leu Thr Tyr Pro Phe Leu Asn Val Phe
1               5
```

REDUCED-FAT FOODSTUFFS AND COOKING OILS, AND METHODS FOR MAKING SAME

The present application is a divisional of U.S. application Ser. No. 13/098,124 filed Apr. 29, 2011 (pending), the entire contents of which is specifically incorporated herein in its entirety by express reference thereto.

FIELD OF THE INVENTION

The present invention relates generally to the generation and production of novel lipase variants. More particularly, it concerns lipase compositions, constructs coding for the expression of these compositions, cells capable of expressing the variants from the constructs, methods of making such compositions, and methods for recognizing long-chain fatty acids as a substrate as well as increasing the trans-selectivity of a lipolytic enzyme. In general, the present invention relates to the recombination and recombinant expression of lipase variants of the *Ustilago maydis* lipase. The invention also relates to methods for the generation and production of lipase variants as catalysts for reducing or eliminating trans-fatty acids from lipids and lipid compositions.

BACKGROUND OF THE INVENTION

Lipases (triacylglycerol acylhydrolases, E.C. 3.1.1.3) consist of a genetically diverse and distinctive grouping of water-soluble hydrolytic enzymes that typically act on the ester bonds of lipid substrates. Lipids can include fats, waxes, sterols, fat-soluble vitamins, monoglycerides, diglycerides, fatty acyls, polyketides, and fatty acids, and exist as a number of variations containing different additional chemical structures such as phospholipids, glycerolipids, glycerophospholipids, sphingolipids, sterol lipids, prenol lipids, saccharolipids, etc. Lipases have been used in ester and amide synthesis, kinetic resolutions or asymmetric synthesis to obtain optically pure compounds, and lipid modifications (Bomscheuer and Kazlauskas, 2005). Lipases play an essential role in: (1) the metabolism of dietary lipids, (2) injury and inflammation, (3) cell biology, (4) fermentation, (5) biocatalysis, (6) vitamin absorption, (7) laundering, (8) synthesis of pharmaceuticals and many other biological and chemical processes. Such wide and varying roles have been attributed to lipase stability in organic solvents, high specificity, high enantio-selectivity and regio-selectivity, and a general lack of a need of cofactors for their action. Genes encoding lipases have been found in most, if not all, types of organisms.

Typically, the tertiary structure of lipases includes the alpha/beta ($\alpha/\beta$) hydrolase fold pattern (Ollis et al., 1992), also common in peptidases and esterases (Holmquist, 2000), and can be composed of a core of up to eight beta strands, connected and surrounded by alpha helices. The active sites of lipases are usually formed by at least a catalytic triad consisting of a serine residue as the nucleophile, a histidine residue, and an aspartic or glutamic acid residue. The active site residues are located in a hydrophobic pocket that is covered by a flap or lid structure, usually composed of amphiphilic $\alpha$ helices (Anthonsen et al., 1995).

Lipases typically act at the interface generated by a hydrophobic lipid substrate in a hydrophilic aqueous medium. There are typically four basic steps in lipase hydrolysis and/or alcoholysis (i.e., ethanolysis), which involves a conformational change of the lipase itself. First, the lipase is adsorbed and activated by the opening of the hydrophobic pocket by displacement of the lid structure, by the so-called interfacial activation. Once the pocket is opened, the ester bond of the lipid substrate is able to reach and bind to the lipase active site. Second, the nucleophilic oxygen of the serine side chain binds the carbonyl carbon of the ester bond, forming a tetrahedral intermediate, stabilized by hydrogen bonding with amide nitrogen atoms of the amino acid residues nearby. Third, the ester bond is cleaved, which frees an alcohol and produces an acyl-enzyme complex. Last, the acyl-enzyme is hydrolyzed upon entry of a water molecule or alcohol into the active site. This frees the fatty acid (in case of water as nucleophile) or ester (in case of an alcohol as nucleophile) and the lipase is regenerated.

Due, in part, to their diverse functioning and structure, as revealed by sequence analysis and crystallography, lipases belong to different enzyme subclasses or families. *Pseudozyma* (formerly *Candida*) *antarctica*, is a basidiomycetous yeast strain isolated from Lake Vanda in Antarctica that produces two differently functioning lipases: lipase A (CAL-A) and lipase B (CAL-B) (Ericsson et al., 2008). These two lipases have been previously characterized and the amino acid and DNA sequences encoding these lipases have been determined (Novo Nordisk A/S, by Hoegh et al., 1995). CAL-B is a widely used enzyme in organic synthesis on both the laboratory and commercial scale, especially in the resolution of racemic mixtures.

CAL-A is one representative of a new class of lipases and, due to its properties, including thermostability, has been used as a catalyst in the paper, wax, food, flavor, and biopharmaceutical industries. CAL-A has an unusual lid structure and C-terminal flap, which can accept very bulky substrates like highly branched acyl groups and sterically hindered alcohols and amines (Kirk and Christensen, 2002; Krishna et al., 2002; Schmidt et al., 2005). CAL-A also shows a higher homology to peptidase structures rather than typical lipase structures (Ericsson et al., 2008).

Mono- or poly-unsaturated fats with trans-isomer fatty acid(s) are commonly called "trans fats." Trans-isomers contain chains where the carbon atoms next to the double bond are located geometrically opposite, whereas in cis-isomers the carbon atoms next to the double bond are geometrically on the same side. In the cis configuration, the naturally occurring unsaturated fatty acids have lower melting points than those of saturated fatty acids, and thus are found in liquid form. Typically, trans-fatty acids are found in food products as a result of a partial hydrogenation process. Trans-fatty acids have higher melting points than those of the cis-unsaturated fatty acids and are less susceptible to auto-oxidation and so can form a more stable solid or semi-solid fat. Dietary intake of trans-fatty acids has been linked to an increased risk for heart disease, diabetes, obesity, metabolic syndrome, Alzheimer's disease, cancer, liver dysfunction and infertility. For these reasons, attempts have been made to reduce the trans-fatty acid content in dietary products (Ratnayake and Cruz-Hernandez, 2009).

Lipases have gained significant commercial importance; however, the expression levels in native organisms are too low to meet these increasing needs. Therefore, numerous attempts have been made to optimize the activity, selectivity, sensitivity and stability of lipases. These include immobilizing the lipase on solid supports and using non-aqueous solvents as well as recombinant DNA techniques and protein engineering. Understanding the mechanisms underlying gene expression, protein folding and excretion of lipases enables higher-level production of these biocatalysts (Napolitano and Giuffrida, 2009).

Numerous lipase assay methods have been used to determine lipase activity, including, but not limited to, using colored or fluorescent substrates, which allow spectroscopic and fluorimetric detection of lipase activity, chromatography techniques including high-performance liquid chromatography (HPLC), silver ion chromatography, gas chromatography and thin layer chromatography, titration of fatty acids released from the substrate, mass spectrometry and controlled surface pressure or oil drop tensiometry.

Due to the central importance of lipase function in lipid metabolism and transport, and its implication in serious diseases and conditions such as heart disease, diabetes, obesity, metabolic syndrome, Alzheimer's disease, cancer, liver dysfunction and infertility, it is imperative to know not only how lipases work, but also how to improve the activity, selectivity, sensitivity and stability of lipases. What is desirable, therefore, are compositions and methods for producing a novel lipase variant, increasing the preference of a lipase for long fatty acid chains, increasing the range and number of fatty acid chains that a lipase is able to catalyze, and increasing the trans-selectivity of lipases and reducing or eliminating trans-fatty acids from lipid substrates. Such compositions and methods find particular utility in a variety of analytical assays and dietary regimens.

BRIEF SUMMARY OF THE INVENTION

The present invention seeks to overcome these and other inherent limitations in the prior art by providing new, non-obvious, and useful compositions, as well as methods of making and employing them, that may advantageously modulate, alter, ameliorate or reduce the amount of trans-fatty acid moieties and/or long chain fatty acid moieties in a substrate or composition containing them.

The invention encompasses a lipase, or variant thereof, that has increased specificity for trans-fatty acid moieties and/or long chain fatty acid moieties. "Lipase variant(s)," or simply "variant(s)" are lypolytic enzymes with a modified amino acid sequence. "Trans-fatty acid moieties" are those fats or lipids that contain trans-isomer (E-isomer) fatty acids. Trans-fatty acid moieties may be or contain monounsaturated or polyunsaturated fatty acids which contain one or more double bonds within the molecule. Lipases, or variants thereof, that act preferentially on trans-fatty acid moieties, rather than cis-fatty acid moieties and/or saturated fatty acid moieties are said to be "trans-selective." Long chain fatty acid moieties are or contain fatty acids with aliphatic tails of 12 carbons or longer. Lipases, or variants thereof, of the invention act preferentially on, or preferentially catalyze long chain fatty acid moiety substrates.

An embodiment provides for an isolated lipase, or variant thereof, that includes an amino acid sequence that is at least about 80%, at least about 85%, at least about 90%, at least about 95%, at least about 98%, or at least about 99% identical to the amino acid sequence of SEQ ID NO:1, SEQ ID NO:4, or SEQ ID NO:6. SEQ ID NO:1 encodes for a parent lipase, the sequence of which is altered, modified or mutated to create lipase variants. SEQ ID NO:4 and SEQ ID NO:6 are lipase variants of SEQ ID NO:1, but their sequences be altered, modified or mutated to create additional lipase variants. The amino acid sequence of SEQ ID NO:4 and SEQ ID NO:6 result from truncations of the N-terminus of the amino acid sequence of SEQ ID NO:1.

A further embodiment provides for an isolated lipase, or variant thereof, that includes at least a first amino acid substitution in one or more of the amino acid residues of SEQ ID NO:1, SEQ ID NO:4, or SEQ ID NO:6 that confers trans-selective lipolytic activity or a preference for catalyzing long chain fatty acid moieties to the lipase, or variant thereof.

Some embodiments may include two, three, four, five, six, seven, eight, nine, or even ten or more amino acid substitutions within SEQ ID NO:1, SEQ ID NO:4, or SEQ ID NO:6. In some embodiments, these substitutions are made at, near or facing the binding tunnel or active site of the lipase, or variant thereof. In other embodiments, these substitutions are made in the lid structure or C-terminal flap of the lipase, or variant thereof. An embodiment provides for an isolated lipase, or variant thereof, wherein the one or more amino acid substitutions is a phenylalanine-to-aspartic acid substitution, an alanine-to-asparagine substitution, a threonine-to-histidine substitution, a phenylalanine-to-serine substitution, a glycine-to-alanine substitution, a glycine-to-tyrosine substitution, a glycine-to-leucine substitution, a valine-to-histidine substitution, a valine-to-isoleucine substitution, or a leucine-to-asparagine substitution, or any combination thereof. Conservative amino acid substitutions A further embodiment provides for an isolated lipase, or variant thereof, that includes one or more amino acid substitutions corresponding to any one or more of residues 269, 338, 341, 342, 357, 421, and 425, wherein each amino acid position is numbered by correspondence to a position in the amino acid sequence of the lipase as set forth in SEQ ID NO:1. In another embodiment, the isolated lipase, or variant thereof, includes one or more amino acid substitutions corresponding to any one or more of residues 145, 214, 217, 218, 233, 297, and 301, wherein each amino acid position is numbered by correspondence to a position in the amino acid sequence of the lipase as set forth in SEQ ID NO:4. In another embodiment, the isolated lipase, or variant thereof, includes one or more amino acid substitutions corresponding to any one or more of residues 124, 193, 196, 197, 212, 276, and 280, wherein each amino acid position is numbered by correspondence to a position in the amino acid sequence of the lipase as set forth in SEQ ID NO:6.

In some embodiments, the substitution at amino acid residue 269 is a phenylalanine-to-aspartic acid substitution, the substitution at amino acid residue 338 is an alanine-to-asparagine substitution, the substitution at amino acid residue 341 is a threonine-to-histidine substitution, the substitution at amino acid residue 342 is a phenylalanine-to-serine substitution, the substitution at amino acid 357 is a glycine-to-alanine, glycine-to-tyrosine, or glycine-to-leucine substitution, the substitution at amino acid residue 421 is a valine-to-histidine substitution or a valine-to-isoleucine substitution, and the substitution at amino acid residue 425 is a leucine-to-asparagine substitution, wherein each amino acid position is numbered by correspondence to a position in the amino acid sequence of the lipase as set forth in SEQ ID NO:1. In further embodiments, the substitution at amino acid residue 145 is a phenylalanine-to-aspartic acid substitution, the substitution at amino acid residue 214 is an alanine-to-asparagine substitution, the substitution at amino acid residue 217 is a threonine-to-histidine substitution, the substitution at amino acid residue 218 is a phenylalanine-to-serine substitution, the substitution at amino acid 233 is a glycine-to-alanine, glycine-to-tyrosine, or glycine-to-leucine substitution, the substitution at amino acid residue 297 is a valine-to-histidine substitution or a valine-to-isoleucine substitution, and the substitution at amino acid residue 301 is a leucine-to-asparagine substitution, wherein each amino acid position is numbered by correspondence to a position in the amino acid sequence of the lipase as set forth in SEQ ID NO:4. In some embodiments, the substitution at amino acid residue 124 is a phenylalanine-to-aspartic acid substitution, the substitution at amino acid residue 193 is an alanine-to-asparagine substitution, the substitution at amino acid residue 196 is a threonine-to-histidine substitution, the substitution at amino acid residue 197 is a phenylalanine-to-serine substitution, the substitution at amino acid 212 is a glycine-to-alanine, glycine-to-tyrosine, or glycine-to-leucine substitution, the substitution at amino acid residue 276 is a valine-to-histidine substitution or a valine-to-isoleucine substitution, and the substitution at amino acid residue 280 is a leucine-to-asparagine substitution, wherein each amino acid position is numbered by correspondence to a position in the amino acid sequence of the lipase as set forth in SEQ ID NO:6.

In further embodiments, the isolated lipase variant has an increased preference or specificity for catalyzing trans-fatty acid moieties when compared to a non-selective or un-substituted lipase. Non-selective lipases are those lipases that do not preferentially catalyze a particular lipid substrate, such as a trans-, cis-, or saturated fatty acid moiety. Un-substituted lipases are those lipases which do not contain any amino acid substitutions. For example, the sequences of SEQ ID NO:1, SEQ ID NO:4, and SEQ ID NO:6 do not contain any amino acid substitutions. Exemplary non-selective lipases include, but are not limited to lipases from *Geobacillus* sp., *Rhizomucor* sp., *Candida rugosa*, and the like.

In some embodiments, the at least a first amino acid substitution confers to the lipase variant polypeptide an increased hydrolytic or alcoholytic, for example, ethanolytic, activity in the presence of trans-fatty acid moieties when compared to a non-selective lipase when both the variant and the non-selective lipase are exposed to the same fatty acid composition. This increased hydrolytic or ethanolytic activity is an indication of preference for the catalysis of a particular substrate. Typically, lipases catalyze the hydrolysis of ester chemical bonds in lipid substrates. They can also catalyze the alcoholysis of the ester bonds in the lipid substrates. In further embodiments, the at least a first amino acid substitution confers to the polypeptide an about 1.0-fold, an about 1.5-fold, an about 2-fold, or an about 2.5-fold increase in hydrolytic or ethanolytic activity in the presence of at least a first trans-fatty acid moiety, when compared to a non-selective or un-substituted lipase.

In further embodiments, the at least a first amino acid substitution confers to the lipase variant polypeptide an increased preference for catalyzing fatty acid moieties having a carbon chain length greater than or equal to twelve ($\geq C_{12}$), greater than or equal to fourteen ($\geq C_{14}$), or greater than or equal to sixteen ($\geq C_{16}$) when compared to the wild-type or parent lipase. In further embodiments, the at least a first amino acid substitution confers to the lipase variant polypeptide an increased preference for catalyzing fatty acid moieties having a carbon chain length greater than or equal to twelve ($\geq C_{12}$), and an about 1.5-fold increase in hydrolytic or ethanolytic activity in the presence of at least a first trans-fatty acid moiety, when compared to the wild-type or parent lipase. In some embodiments, the at least a first amino acid substitution confers to the lipase variant polypeptide an increased preference for catalyzing fatty acid moieties having a carbon chain length greater than or equal to fourteen ($\geq C_{14}$), and an about 1.5-fold increase in hydrolytic or ethanolytic activity in the presence of at least a first trans-fatty acid moiety, when compared to the wild-type or parent lipase. In other embodiments, the at least a first amino acid substitution confers to the lipase variant polypeptide an increased preference for catalyzing fatty acid moieties having a carbon chain length greater than or equal to sixteen ($\geq C_{16}$), and an about 1.5-fold increase in hydrolytic or ethanolytic activity in the presence of at least a first trans-fatty acid moiety, when compared to the wild-type or parent lipase. In other embodiments, the at least a first amino acid substitution confers to the lipase variant polypeptide an increased preference for catalyzing fatty acid moieties having a carbon chain length greater than or equal to fourteen ($\geq C_{14}$), and an about 2.0-fold increase in hydrolytic or ethanolytic activity in the presence of at least a first trans-fatty acid moiety, when compared to the wild-type or parent lipase. In other embodiments, the at least a first amino acid substitution confers to the lipase variant polypeptide an increased preference for catalyzing fatty acid moieties having a carbon chain length greater than or equal to fourteen ($\geq C_{14}$), and an about 2.5-fold increase in hydrolytic or ethanolytic activity in the presence of at least a first trans-fatty acid moiety, when compared to the wild-type or parent lipase. In still other embodiments the at least a first amino acid substitution confers to the lipase variant polypeptide an increased preference for catalyzing fatty acid moieties having a carbon chain length greater than or equal to sixteen ($\geq C_{16}$), and an about 2.0-fold increase in hydrolytic or ethanolytic activity in the presence of at least a first trans-fatty acid moiety, when compared to the wild-type or parent lipase. In still other embodiments the at least a first amino acid substitution confers to the lipase variant polypeptide an increased preference for catalyzing fatty acid moieties having a carbon chain length greater than or equal to sixteen ($\geq C_{16}$), and an about 2.5-fold increase in hydrolytic or ethanolytic activity in the presence of at least a first trans-fatty acid moiety, when compared to the wild-type or parent lipase.

In further embodiments, the isolated lipase, or variant thereof, includes: (a) an amino acid sequence that is at least about 95% identical to the amino acid sequence of any one of SEQ ID NO:1, SEQ ID NO:4, or SEQ ID NO:6, or to a complement thereof; and (b) one or more amino acid substitutions corresponding to residues 269, 338, 341, 342, 357, 421, or 425, wherein each amino acid position is numbered by correspondence to a position in the amino acid sequence of the lipase as set forth in SEQ ID NO:1; and further wherein the one or more amino acid substitutions confers to the polypeptide an increased preference for catalyzing fatty acid moieties having a carbon chain length greater than or equal to twelve ($\geq C_{12}$), or an about 1.5-fold increase in hydrolytic or ethanolytic activity in the presence of at least a first trans-fatty acid moiety, when compared to the wild-type or parent lipase, or a combination thereof.

In some embodiments, the isolated lipase, or variant thereof, is about 400 to about 500 amino acids in length, about 410 to about 490 amino acids in length, about 420 to about 480 amino acids in length, about 425 to about 470 amino acids in length, about 430 to about 460 amino acids in length, or about 425 to about 450 amino acids in length.

In some embodiments, the isolated lipase, or variant thereof, is about 425 to about 470 amino acids in length; is at least about 95% identical to the amino acid sequence of SEQ ID NO:4, or SEQ ID NO:6, or to a complement thereof; and includes one or more amino acid substitutions corresponding to residues 269, 338, 341, 342, 357, 421, or 425, wherein each amino acid position is numbered by correspondence to a position in the amino acid sequence of the lipase as set forth in SEQ ID NO:1, and further wherein the one or more amino acid substitutions confers to the polypeptide an increased preference for catalysis of long-chain fatty acids, or an increased trans-selective lipolytic activity, or a combination thereof. In other embodiments, the isolated lipase, or variant thereof, is about 430 to about 460 amino acids in length; and is at least about 98% identical to the amino acid sequence of SEQ ID NO:4, or SEQ ID NO:6, or to a complement thereof. In yet other embodiments, the isolated lipase, or variant thereof, is about 425 to about 470 amino acids in length; is at least about 95% identical to the amino acid sequence of SEQ ID NO:4, or SEQ ID NO:6, or to a complement thereof; includes one or more amino acid substitutions corresponding to residues 269, 338, 341, 342, 357, 421, or 425, wherein each amino acid position is numbered by correspondence to a position in the amino acid sequence of the lipase as set forth in SEQ ID NO:1, and has an about 1.5-fold increase in hydrolytic or ethanolytic activity in the presence of at least a first trans-fatty acid moiety, or an increased preference for catalyzing fatty acid moieties having a carbon chain length greater than or equal to twelve ($\geq C_{12}$), when compared to the wild-type, un-substituted, or parent lipase.

Some embodiments include a composition that includes the isolated lipase, or variant thereof of the present invention, as described above.

In some embodiments, the composition further includes a lipid, a fatty acid, a sterol, a wax, an oil, a triglyceride, an ester, or a carboxylic acid moiety. Further embodiments include a binding medium to which the lipase, or variant thereof, binds or cross-links. In some embodiments, the lipase, or variant thereof, is substantially bound or substantially chemically cross-linked to a matrix, a column, a fiber, a filter, a resin, a gel, a bead, or any combination thereof. In this manner, the composition may act as a filter through which compositions containing substrates can pass, thereby allowing the lipase, or variant thereof, to act upon the substrate, yet remain bound to a removable substance.

In further embodiments, the composition further includes one or more additional enzymes. These enzymes may aid in the process of creating or manufacturing a low or no trans-fatty acid composition and/or may act as co-factors for the lipase, or variant thereof. Additionally, the one or more additional enzymes may include a second, distinct, lipase, or a variant thereof. The one or more additional enzymes may also include one or more lipases, esterases, lyases, deproteinases, phosphatases, dehydrogenases, transglutaminases, oxidases, or any combination thereof.

Some embodiments include an isolated polynucleotide that encodes the lipase, or the variant thereof, of the present invention.

Further embodiments include an expression vector including an isolated polynucleotide that encodes the lipase, or variant thereof. In some embodiments, the expression vector includes an isolated polynucleotide that is codon-optimized for expression in a bacterial or non-basidiomyceteous yeast cell. In some embodiments, the bacterial cell is *E. coli* or the non-basidiomycetous yeast cell is *P. pastoris*. In further embodiments, the expression vector is defined as pET22-lipUMsophis, or pET22-lipUMfophis. Further embodiments include a microbial host cell transformed with the isolated polynucleotide, or the expression vector. In some embodiments, the microbial host cell is an *E. coli* or a *P. pastoris* host cell. In further embodiments, the expression vector is transformed into a non-*Ustilago maydis* microbial host cell. In yet other embodiments, the microbial host cell is a *Pischia pastoris* host cell deposited with the Deutsche Sammlung von Mikroorganismen and Zellkulturen GmbH (DSMZ) under the accession number 24702.

Further embodiments encompass a method for producing a lipase variant, including (a) culturing a microbial host cell that encodes the lipase, or variant thereof, under conditions conducive to the expression and secretion of the lipase, or the variant thereof, and (b) recovering the expressed lipase, or variant thereof, from the culture.

Some embodiments include a variant of a parent lipolytic enzyme, which includes: (a) one or more amino acid substitutions corresponding to residues 269, 338, 341, 342, 357, 421, or 425; wherein each amino acid position is numbered by correspondence to a position in the amino acid sequence of the lipase as set forth in SEQ ID NO:1, or (b) one or more amino acid substitutions corresponding to residues 145, 214, 217, 218, 233, 297, or 301; wherein each amino acid position is numbered by correspondence to a position in the amino acid sequence of the lipase as set forth in SEQ ID NO:4; wherein the one or more amino acid substitutions confer to the polypeptide an increased lipolytic activity toward trans-fatty acid moieties, or a preference for catalysis of one or more long-chain fatty acids.

In further embodiments, no more than about 10, no more than about 8, no more than about 7, no more than about 6, no more than about 5, no more than about 4, no more than about 3, no more than about 2, or no more than about 1 amino acid substitution(s) are made within the variant.

In other embodiments, the parent lipolytic enzyme is a *Ustilago maydis* lipase.

In other embodiments, the variant includes a phenylalanine-to-aspartic acid substitution, an alanine-to-asparagine substitution, a threonine-to-histidine substitution, a phenylalanine-to-serine substitution, a glycine-to-alanine substitution, a glycine-to-tyrosine substitution, a glycine-to-leucine substitution, a valine-to-histidine substitution, a valine-to-isoleucine substitution, or a leucine-to-asparagine substitution, or any combination thereof.

In still other embodiments, the variant includes a phenylalanine-to-aspartic acid substitution at amino acid residue 145 (F145D); an alanine-to-asparagine substitution at amino acid residue 214 (A214N); a threonine-to-histidine substitution at amino acid residue 217 (T217H); a phenylalanine-to-serine substitution at amino acid residue 218 (F218S); a glycine-to-alanine (G233A), a glycine-to-tyrosine (G233Y), or a glycine-to-leucine (G233L) substitution at amino acid residue 233; a valine-to-histidine (V297H) or a valine-to-isoleucine (V297I) substitution at amino acid residue 297; or a leucine-to-asparagine substitution at amino acid residue 301 (L301N) of SEQ ID NO:4.

Some embodiments include a method of obtaining an isolated *Ustilago maydis* lipase variant, including: mutagenizing a polynucleotide that encodes the polypeptide of SEQ ID NO:1, SEQ ID NO:4, or SEQ ID NO:6 under conditions effective to generate at least a first lipase variant that comprises an amino acid substitution in at least a first amino acid residue therein that confers to the polypeptide an increased trans-selectivity, or an increased preference for catalyzing long-chain fatty acid moieties ($\geq C_{12}$) over that of medium or short-chain fatty acid moieties ($< C_{12}$); transforming a suitable microbial host cell with the mutagenized polynucleotide; culturing the microbial host cell under conditions effective to express the first lipase variant; and recovering the first expressed lipase variant from the culture.

Further embodiments include a method of reducing or eliminating one or more trans-unsaturated fatty acid compounds or one or more long-chain ($\geq C_{12}$) fatty acid moieties from a substrate, including contacting the substrate with an effective amount of a composition comprising the lipase, or variant thereof, of claim 1, for a time sufficient to hydrolyze or esterify at least a portion of the substrate thereby reducing or eliminating the one or more trans-unsaturated fatty acid compounds or the one or more long-chain ($\geq C_{12}$) fatty acid moieties from the substrate. In some embodiments, the method further includes removing the lipase, or variant thereof, from the composition after the one or more trans-unsaturated fatty acid compounds or the one or more long-chain ($\geq C_{12}$) fatty acid moieties has been substantially reduced or eliminated from the substrate. In some embodiments, the substrate includes an edible lipid, an edible fat, an edible fatty acid, an edible sterol, an edible wax, an edible oil, or an edible triglyceride, or any combination thereof. Further embodiments include a fat-containing product having reduced trans-fatty acid moieties, or essentially no trans-fatty acid moieties, produced by this method. In some embodiments, the fat-containing product is suitable for human consumption. In further embodiments, the fat-containing product is characterized as a cooking ingredient, or a frying oil.

An embodiment provides for an isolated polypeptide including a lipase variant that includes a modified *Ustilago maydis* parent lipase amino acid sequence, wherein the lipase variant has lipolytic activity.

Another embodiment provides an isolated polypeptide including a modified *Ustilago maydis* protein segment that has lipolytic activity, wherein the protein segment reduces the amount of trans-fatty acid moieties present in a composition containing them by about 20%. In some embodiments, the protein segment is selective for fatty acid moieties having a chain length of about 14 carbon atoms or more.

In yet another embodiment, the isolated polypeptide includes: (a) a polypeptide region of from about 386 to about 592 amino acids in length that includes an amino acid sequence that is at least 80% identical to a first sequence in accordance with any one of SEQ ID NO:1, SEQ ID NO:4, or SEQ ID NO:6, or (b) a polypeptide region that consists of the amino acid sequence of SEQ ID NO:4, wherein the region has lipolytic activity when in contact with a lipid substrate, preferably a trans-fatty acid or long chain fatty acid substrate. In farther embodiments, the polypeptide is from about 386 to about 592 amino acids in length and consists of an amino acid sequence that is at least about 90% identical to the sequence of any one of SEQ ID NO:1, SEQ ID NO:4, or SEQ ID NO:6, or any variant thereof. In still further embodiments, the polypeptide region is from about 386 to about 592 amino acids in length and consists of an amino acid sequence that is at least about 95% identical, in other embodiments about 98% identical, to the sequence of any one of SEQ ID NO:1, SEQ ID NO:4, or SEQ ID NO:6, or any variant thereof. In particular embodiments there is a substitution of any non-native amino acid at, near or facing the binding tunnel or active site of the polypeptide. In some embodiments, the substitution is selected from the group consisting of a substitution of a non-native amino acid at position 145 in SEQ ID NO:4, or a similarly situated amino acid in SEQ ID NO:1; a substitution of a non-native amino acid at position 214 in SEQ ID NO:4, or a similarly situated amino acid in SEQ ID. NO:1 or SEQ ID NO:6; a substitution of a non-native amino acid at position 217 in SEQ ID NO:4, or a similarly situated amino acid in SEQ ID NO:1 or SEQ ID NO:6; a substitution of a non-native amino acid at position 218 in SEQ ID NO:4, or a similarly situated amino acid in SEQ ID NO:1 or SEQ ID NO:6; a substitution of a non-native amino acid at position 297 in SEQ ID NO:4, or a similarly situated amino acid in SEQ ID NO:1 or SEQ ID NO:6; a substitution of a non-native amino acid at position 301 in SEQ ID NO:4, or a similarly situated amino acid in SEQ ID NO:1 or SEQ ID NO:6; and any combination of the above-listed substitutions. "Similarly situated" means an amino acid within the same surrounding sequence. In further embodiments, the substitution is respectively selected from the group consisting of: F145D, or a similarly situated amino acid in SEQ ID NO:1; A214N, or a similarly situated amino acid in SEQ ID NO:1 or SEQ ID NO:6; T217H, or a similarly situated amino acid in SEQ ID NO:1 or SEQ ID NO:6; F218S, or a similarly situated amino acid in SEQ ID NO:1 or SEQ ID NO:6; V297H or V297I, or a similarly situated amino acid in SEQ ID NO:1 or SEQ ID NO:6; L301N, or a similarly situated amino acid in SEQ ID NO:1 or SEQ ID NO:6; G233A, G233Y, G233L, or a similarly situated amino acid in SEQ ID NO:1 or SEQ ID NO:6; and any combination of these substitutions.

In another embodiment, the C-terminal flap portion of the lipolytic enzyme of the isolated polypeptide is removed or rendered non-functional.

In yet another embodiment, the composition includes at least a first polypeptide according to any of the above-mentioned embodiments and a binding medium to which the polypeptide binds or cross-links to act as a filter. Some embodiments further include at least a second distinct polypeptide according to any of the above-mentioned embodiments.

In particular embodiments, the composition can include from about 1% to about 99% by weight of the polypeptide.

In some embodiments, the composition is formulated as a powder, dust, pellet, granule, spray, emulsion, colloid, or solution, or any combination thereof. The lipase variants of these formulations may be immobilized on a solid carrier material or in cells.

In further embodiments, the composition is prepared by desiccation, lyophilization, homogenization, extraction, filtration, centrifugation, sedimentation, or a concentration of a culture of *E. coli* or *P. pastoris* cells.

Further embodiments encompass an isolated nucleic acid molecule having a nucleotide sequence selected from the group consisting of: a nucleotide sequence, or the complement thereof, consisting essentially of an at least 300 continuous nucleotide segment from any one of SEQ ID NO:2, SEQ ID NO:5, SEQ ID NO:10, SEQ ID NO:11, SEQ ID NO:12, or SEQ ID NO:13; a nucleotide sequence, or the complement thereof, encoding at least a 396 contiguous amino acid segment of any one of the amino acid sequences shown in SEQ ID NO:1, SEQ ID NO:4, or SEQ ID NO:6, wherein said segment has lipolytic activity; and a nucleotide sequence, or the complement thereof, encoding at least a 417 contiguous amino acid segment of any one of the amino acid sequences shown in SEQ ID NO:1, SEQ ID NO:4, or SEQ ID NO:6 and includes any one of the mutations as stated above, wherein the segment has lipolytic activity and increased trans-selectivity and/or fatty acid long chain length preference.

One embodiment is directed to host organisms that contain nucleic acids of the invention. Another embodiment includes a recombinant nucleic acid vector including at least a first sequence region that encodes any of the above-mentioned isolated polypeptides or the isolated nucleic acids. In some embodiments, the nucleic acid vector is further defined as a plasmid vector.

Yet another embodiment encompasses a transformed non-human host cell including a nucleic acid segment that encodes any of the above-mentioned isolated polypeptides. In some embodiments, the transformed non-human host cell is further defined as a bacterial cell or a yeast cell. In further embodiments, the transformed non-human host cell is further defined as an *E. coli* bacterial cell or *P. pastoris* yeast cell.

Still other embodiments are directed to methods for producing recombinant proteins with lipolytic activity including an amino acid sequence selected from the group consisting of: the amino acid sequence shown in SEQ ID NO:1, the amino acid sequence shown in SEQ ID NO:4, the amino acid sequence shown in SEQ ID NO:6, and including introducing a nucleotide sequence encoding the polypeptide into a host cell, culturing the host cell under conditions in which the polypeptide is expressed, and recovering, isolating and/or purifying the polypeptide from the culture.

Further embodiments encompass methods for obtaining a modified *Ustilago maydis* protein with lipolytic activity having increased trans-selectivity including: providing a polynucleotide encoding the polypeptide sequence of any one or more of SEQ ID NO:1, SEQ ID NO:4, or SEQ ID NO:6; altering the nucleic acid sequence encoding for any non-native amino acid at, near or facing a proposed three-dimensional binding, active site or tunnel of the polypeptide or removing or rendering non-functional the C terminal flap of the polypeptide; introducing the altered nucleotide sequence encoding the polypeptide into a host cell; culturing the host cell under conditions in which the polypeptide is expressed; and recovering the polypeptide from the culture.

Further embodiments include methods to reduce or eliminate the content of trans-unsaturated fatty acid compounds from a substrate including: providing a solution including a stable substrate containing trans-unsaturated fatty acid moieties; and contacting any of the above-mentioned compositions with the solution including a stable substrate for a sufficient amount of time to hydrolyze or esterify at least a portion of the trans-unsaturated fatty acid moieties. In some embodiments, the method further includes exposing the recovered polypeptide to a substrate containing trans-unsaturated fatty acid compounds. In some embodiments, the stable structure in the method is stable liquid frying oil. In some embodiments, the method further includes removing or inactivating at least a portion of the composition after contacting the solution including a stable substrate.

Another embodiment encompasses a fat-containing product having reduced trans-fatty acid moieties or no trans-fatty acid moieties as produced from the above-described method.

Further embodiments include methods of producing a low trans-fatty acid composition including: providing a polynucleotide encoding at least a functional lipase variant polypeptide that comprises, consists essentially of, or alternatively, consists of the amino acid sequence of any one or more of SEQ ID NO:1, SEQ ID NO:4, or SEQ ID NO:6; altering the nucleic acid sequence encoding for any non-native amino acid at, near or facing a proposed three-dimensional binding, active site or tunnel of the polypeptide or removing or rendering non-functional the C-terminal flap of the polypeptide; introducing the altered nucleotide sequence encoding the polypeptide into a host cell; culturing the host cell under conditions in which the polypeptide is expressed; recovering the polypeptide from the culture; providing a solution including a stable substrate containing trans-unsaturated fatty acid moieties; and contacting a composition containing the recovered polypeptide with the solution including a stable substrate for a sufficient amount of time to hydrolyze or esterify at least a portion of the trans-unsaturated fatty acid moieties. Some embodiments further include removing or inactivating the composition after contacting the solution including a stable substrate.

BRIEF DESCRIPTION OF THE DRAWINGS

Reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which.

DESCRIPTION OF ILLUSTRATIVE EMBODIMENTS

Figure 1:
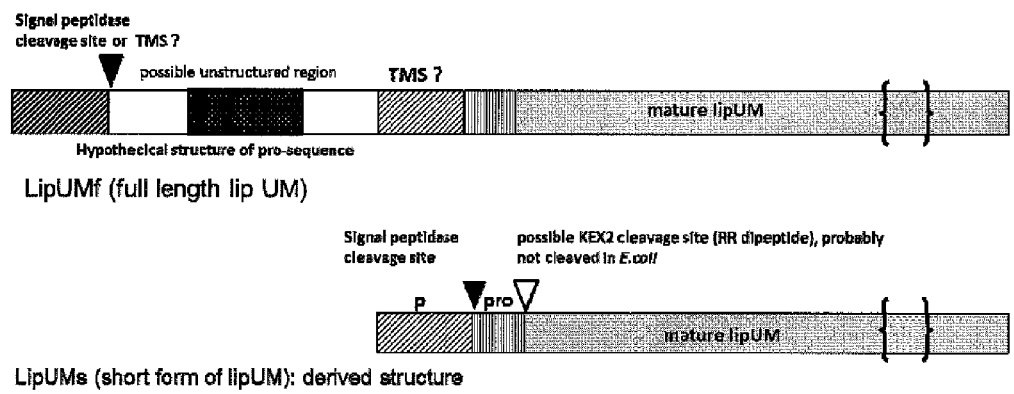
FIG. 1 shows a schematic representation of the two lipUM variants, the full sequence of lipUM (hereinafter "lipUMf" or alternatively, "lipUM") and the shortened sequence of lipUM (hereinafter "lipUMs")

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Any suitable parent polypeptide with lipolytic enzyme activity may be used. In an embodiment, the parent lipase is a microbial polypeptide, preferably a bacterial or a fungal polypeptide, and more particularly, one or more polypeptides of yeast origin, such as, but not limited to, one or more polypeptides from any one or more species of the genera *Acremonium, Aspergillus, Aureobasidium, Candida, Cryptococcus, Filobasidium, Fusarium, Humicole, Kluyveromyces, Kurtzmanomyces, Magnaporthe, Mucor, Myceliophthora, Neocallimastix, Neurospora, Paecilomyces, Penicillium, Pichia, Piromyces, Saccharomyces, Schizophyllum, Schizosaccharomyces, Sporisorium, Talaromyces, Thermoascus, Thielavia, Tolvpoceladium, Trichoderma, Ustilago,* and *Yarrowia.* In an embodiment, the parent lipase is a polypeptide of *Ustilago* origin. In another embodiment, the parent lipase is a putative wild-type *Ustilago maydis* lipase. In another embodiment, the parent lipase has a sequence essentially as set forth in SEQ ID NO:1, or a lipase variant thereof as defined herein, which contains the following sequence (hereinafter referred to as the amino acid sequence or sequence of "LipUM" or "LipUMf") (Uniprot Q4P903):

```
                                    (SEQ ID NO: 1)
MWGRIRNVIQPTWAPPLFGTLNIIFSLFFRAGIARSHKWTWCCYRPTRMA

RSRTFSNSAPTRRRPERLRLQKGSSNTTIRPRPSAILPDEMNHGSLLTVV

PHTVVASTPSFRSSFPDSLIASVQMRFIAVRAIVTLAAAAAVSLAVPTER

RAAFADPNDDLFYTTPDNINTYANGQVIQSRKADTDIGNSNKVEAFQLQY

RTTNTQKEAQANVATVWIPNKPASPPKIFSYQVYQDSTQLNCAPSYSFLK

GLDKPNKATTILEAPIIIGWALQQGFYVVSSDHEGPRSSFIAGYEEGMAI

LDGIRALKNYAKLPTDSAIGFYGYSGGAHATGWAANLAGSYAPEHNIIGA
```

-continued
```
AYGGLPASARDTFNFLNKGAFAGFAIAGVSGLALAYPDVETYIQSRLNAK

GEKVFKQVRSRGFCIGQVVLTYPFVDAYSLINDTNLLNEEPVASTLKSET

LVQAEASYTVPVPKFPRFIWHALLDEIVPFHSAATYVKEQCSKGADINWN

VYSFAEHISAELFGLLPGLDWLNKAYKGQAPKVPCGGGAQSVMGASGPPA

QDVLGADLASQLRSLQGKPSAFGNKPFGSISP,
```

Lipases and lipase variants are those enzymes that have the enzymatic activity of a lipase. Lipase variants are typically prepared by specific modification of parent lipases. In an embodiment, the parent lipase may be a lipase with an amino acid sequence having at least about 60% to about 99.9% homology to the sequence of the lipase shown in SEQ ID NO:1. In another embodiment, there is at least about a 70% to about 99.5% homology to the amino acid sequence of the lipase shown in SEQ ID NO:1. In an yet another embodiment, there is at least about a 80% to about an 99% homology to SEQ ID NO:1.

Sequence alignment and calculations of percent homology may be performed by techniques well known to those of ordinary skill in the art. Nucleic acid sequences, such as deoxyribonucleic acid (DNA) and ribonucleic acid (RNA), either synthetically or naturally occurring, that encodes the lipase, or variant thereof, of the present invention are also within the scope of the present invention.

Lipase polynucleotides can include nucleic acids including RNA, such as mRNA, DNA, including cDNA and genomic DNA, and can be either single or double stranded. The lipase polynucleotides include, but are not limited to, the sequence encoding the mature parent polypeptides alone, or variants thereof, including fragments, the sequence encoding the mature polypeptide, or variants thereof, including additional coding sequences, such as a leader or secretory sequence (e.g., a pre-pro or pro-protein sequence), the sequence encoding the mature parent polypeptide, or variants thereof, with or without additional coding sequences, with additional non-coding sequences (e.g., introns, transcribed but not translated sequences, mRNA processing sequences, ribosome binding sequences and stability sequences for mRNA). Additionally, the nucleotide sequence may be fused to a marker sequence. In one embodiment, the lipase nucleic acids include only the coding regions. The nucleotide sequence may encompass fragments of the entire sequence of the respective variant lipases and the sequence may differ than those described due to degeneracy of the genetic code.

For example, a parent lipase polynucleotide includes the following DNA sequence, which encodes for the amino acid sequence of SEQ ID NO:1:

```
                                          (SEQ ID NO: 2)
ATGTGGGGCGCATCCGCAACGTTATTCAGCCAACTTGGGCGCCGCCGTT

ATTTGGCACCCTGAATATCATTTTTAGCCTTTTTTTCCGTGCCGGGATTG

CAAGGTCGCACAAATGGACATGGTGCTGCTACAGACCGACTCGAATGGCC

AGAAGCCGCACATTCTCGAATTCGGCTCCAACCAGACGGCGGCCCGAACG

ATTACGGTTGCAGAAGGGTTCGTCTAATACTACCATTCGCCCGCGCCCTT

CGGCTATTTTGCCTGACGAGATGAACCATGGCTCGCTGCTTACGGTTGTC

CCGCACACTGTAGTCGCCTCCACCCCCTCCTTTCGTTCTTCCTTTCCAGA

TTCGTTGATCGCCTCGGTTCAGATGAGGTTCATTGCTGTTCGGGCTATCG
```

```
                                                    -continued
TGACGCTAGCGGCTGCAGCCGCCGTGTCGCTTGCAGTGCCCACAGAGCGA

AGGGCAGCGTTCGCCGATCCAAACGACGATCTCTTCTACACCACGCCGGA

CAACATCAACACATATGCCAATGGTCAGGTCATCCAGTCACGCAAGGCTG

ATACCGATATTGGGAACAGCAACAAGGTTGAAGCTTTCCAGCTTCAATAT

CGCACTACCAATACGCAAAAGGAGGCGCAGGCCAACGTTGCTACCGTATG

GATCCCCAACAAGCCCGCTTCACCTCCCAAGATCTTCTCTTATCAGGTCT

ATCAGGACTCGACACAGCTCAACTGTGCTCCGAGCTATAGCTTTTTGAAG

GGCCTTGACAAGCCTAACAAAGCTACCACGATCCTCGAAGCACCCATCAT

CATCGGCTGGGCGCTCCAACAAGGTTTCTACGTCGTCTCGTCTGATCACG

AAGGCCCGCGCTCATCGTTCATTGCGGGCTACGAGGAAGGTATGGCTATT

CTCGACGGCATACGTGCGCTCAAGAACTACGCCAAACTGCCCACGGACAG

CGCGATCGGCTTTTACGGATACAGCGGCGGTGCCCATGCAACCGGCTGGG

CAGCTAATCTGGCAGGGAGCTACGCTCCTGAGCACAACATCATCGGTGCT

GCCTACGGAGGACTGCCTGCTAGCGCCAGAGACACATTCAACTTCCTCAA

CAAAGGCGCGTTTGCCGGCTTCGCCATTGCGGGTGTCTCGGGTCTTGCGC

TGGCCTACCCGGACGTGGAGACCTACATCCAGTCGCGCCTCAACGCCAAG

GGAGAAAAGGTGTTTAAACAGGTCCGAAGTCGCGGCTTCTGCATTGGCCA

AGTGGTCCTAACCTACCCATTCGTCGACGCCTATTCACTCATCAACGACA

CAAACCTTCTCAACGAGGAACCGGTCGCCAGCACGTTGAAATCCGAGACG

TTGGTTCAGGCCGAGGCTAGCTACACGGTTCCTGTTCCCAAATTCCCGCG

TTTCATCTGGCATGCGCTCTTGGACGAGATTGTTCCCTTCCACTCGGCTG

CGACCTATGTCAAGGAGCAGTGTTCAAAGGGCGCCGACATCAACTGGAAT

GTCTACTCATTTGCCGAGCACATCTCTGCCGAGCTTTTCGGCTTGCTGCC

TGGTCTCGACTGGTTAAACAAGGCTTACAAGGGTCAAGCACCCAAAGTGC

CTTGTGGCGGAGGGGCTCAAAGCGTGATGGGTGCCTCAGGCCCGCCTGCG

CAGGACGTTCTGGGAGCTGACCTGGCAAGCCAACTCCGATCTCTCCAGGG

TAAGCCTTCTGCGTTTGGCAACAAACCTTTTGGCTCCATCTCCCCCTGA.
```

The wild-type lipase A derived from *Candida antarctica* (i.e. CAL-A) (Protein Data Bank (pdb) 3guu) has the following amino acid sequence:

(SEQ ID NO: 3)
MRVSLRSITSLLAAATAAVLAAPAAETLDRRAALPNPYDDPFYTTPSNIG

TFAKGQVIQSRKVPTDIGNANNAASFQLQYRTTNTQNEAVADVATVWIPA

KPASPPKIFSYQVYEDATALDCAPSYSYLTGLDQPNKVTAVLDTPIIIGW

ALQQGYYVVSSDHEGFKAAFIAGYEEGMAILDGIRALKNYQNLPSDSKVA

LEGYSGGAHATVWATSLAESYAPELNIVGASHGGTPVSAKDTFTFLNGGP

FAGFALAGVSGLSLAHPDMESFIEARLNAKGQRTLKQIRGRGFCLPQVVL

TYPFLNVFSLVNDTNLLNEAPIASILKQETVVQAEASYTVSVPKFPRFIW

HAIPDEIVPYQPAATYVKEQCAKGANINFSPYPIAEHLTAEIFGLVPSLW

FIKQAFDGTTPKVICGTPIPAIAGITTPSADQVLGSDLANQLRSLDGKQS

AFGKPFGPITPP, is used as a reference but is not defined as a parent lipase. The expression, sequence and cloning methods as per this sequence have previously been described (Hoegh et al., 1995).

A lipase variant can differ in amino acid sequence from its parent lipase by one or more substitutions, deletions, insertions, inversions, fusions, mutations, and truncations, or a combination of any of these. These lipase variants are therefore "modified" proteins or polypeptides. Additional modifications may include post-translational changes. Variant lipases can be fully functional, can lack function in one or more activities or can exhibit one or more additional activities.

In one embodiment, the lipase variants increase the trans-selectivity of the parent lipase. For example, the lipase variants act on or show a preference for trans-fatty acid esters or carboxylic acid moieties. In another embodiment, the lipase variants demonstrate a preference for long chain fatty acid esters or carboxylic acid moieties with a chain length greater than $C_{12}$, wherein C indicates carbon and the number indicates the number of carbons within the fatty acid esters or carboxylic acid moieties. As used herein, the term "long chain fatty acid" refers to a saturated or unsaturated fatty acid containing 12 or more carbon atoms, unless otherwise specified. Examples of long chain fatty acid include myristic acid, palmitic acid, stearic acid, palmitoleic acid, oleic acid, linoleic acid, α-linolenic acid, γ-linolenic acid, and the like. In yet another embodiment, the lipase variants have both, act on or show a preference for trans-fatty acid esters or carboxylic acid moieties and act on or show a preference for long chain fatty acid esters or carboxylic acid moieties.

In describing some lipase variants, the following standard protein mutational nomenclature is used for ease of reference: $N_1\#\#\#N_2$, where $N_1$=single-letter abbreviation of original amino acid, ###=amino acid position, and $N_2$=single-letter abbreviation of the substituted amino acid. For example, according to this nomenclature, the substitution of phenylalanine for aspartic acid in position 145 is shown as F145D.

In one embodiment, substitution of at least a portion of the amino acid sequence of the lipUMf may occur so as to increase the trans-selectivity of the lipase encoded by the lipUMf sequence and/or act on or show a preference for long chain fatty acid esters or carboxylic acid moieties. For example, the amino acid sequence of a lipUMf polypeptide may be altered or mutated to increase access of a substrate to the active site or binding tunnel of the lipase. Preferably, these alterations or mutations occur in either the predicted lid structure and/or C-terminal flap of the lipUMf polypeptide. More specifically, amino acid residues at about position 441 through about position 449 may be substituted with the amino acid residues at about position 300 through about position 308 in SEQ ID NO:3, i.e., substitution of the amino acid sequence PVASTLKSE (SEQ ID NO:32) in SEQ ID NO:1 for the amino acid sequence LTYPFLNVF (SEQ ID NO:33). Alternatively, or in addition to this substitution, the C-terminal flap portion of the lipUMf sequence may be cleaved, truncated, mutated or altered. More specifically, any amino acid residue at about position 541 to about position 582 in SEQ ID NO:1 can be substituted with a STOP codon (denoted by '*'). For example, possible mutations can include a truncation of the sequence at amino acid 541 with a STOP codon (S541*), V542*, M543*, G544*, A545*, S546*, G547*, P548*, P549*, A550*, Q551*, D552*, V553*, L554*, G555*, A556*, D557*, L558*, A559*, S560*, Q561*, L562*, R563*, S564*, L565*, Q566*, G567*, K568*, P569*, S570*, A571*, F572*, G573*, N574*, K575*, P576*, F577*, G578*, S579*, I580*, S581* and/or P582*.

In describing some lipase variants, the following nomenclature is used for ease of reference: symbol of first amino acid deleted; numerical position of first amino acid deleted _ symbol of last amino acid deleted; numerical position of last amino acid deleted;del. For example, according to this nomenclature and referring to the sequence of SEQ ID NO:1, the deletion of methionine at position 1 through glutamine at position 124 would result in the following notation: M1_Q124del. If only one amino acid is deleted, this would result in only one amino acid and its position identified in the notation. For example, a deletion of methionine at position 125 in SEQ ID NO:1 would result in the following notation: M125del. In all cases, the accepted IUPAC single letter or triple letter amino acid abbreviation is employed. All amino acid substitutions are numbered beginning with the N-terminus of the processed form of the sequence. For example, the amino acid sequence numbering starts at the N-terminus of the protein without the actual and/or proposed signal sequence in the case of secreted proteins.

In one embodiment, the lipase variant includes one or more deletions of the N-terminus of the *Ustilago maydis* lipase. In an embodiment, the N-terminus deletion of the lipase sequence maintains and/or increases the lipolytic activity of the lipase when compared to lipUMf. In another embodiment, the N-terminus deletion of the lipase sequence increases the ability of the resultant recombinant protein to be secreted from a host system. For example, in some embodiments, removal of the N-terminus increases the movement of the lipase variant into the periplasmic space of an organism such as bacteria or yeast. In other embodiments, removal of the N-terminus increases the movement of the lipase variant outside of the host organism itself. The N-terminus accounts for about 0.01% to about 30% of the full length amino acid sequence, about 5% to about 25% of the full length amino acid sequence, or about 10% to about 20% of the full length amino acid sequence. Alternatively, the N-terminus can account for up to about the first 175 amino acid residues of SEQ ID NO:1, up to about the first 146 amino acid residues of SEQ ID NO:1, or up to about the first 117 amino acid residues of SEQ ID NO:1. Deletions can be of any length and can take place at any point along the N-terminus of the amino acid sequence of SEQ ID NO:1, and new translation starting or initiation sites can be added to the resulting or remaining sequence as necessary. In one embodiment, the amino acids at about position M1 to about position A34 are removed from the parent lipase of SEQ ID NO:1 (i.e., a M1_A34del mutant). In an embodiment, the amino acids at about position M1 to about position Q124 are removed from the parent lipase of SEQ ID NO:1 (i.e., a M1_Q124del mutant). In another embodiment, the lipase variant's sequence is essentially as set forth in SEQ ID NO:4 (hereinafter referred to as the amino acid sequence or sequence of "LipUMs"):

(SEQ ID NO: 4)

MRFIAVRAIVTLAAAAAVSLAVPTERRAAFADPNDDLFYTTPDNINTYAN

GQVIQSRKADTDIGNSNKVEAFQLQYRTTNTQKEAQANVATVWIPNKPAS

PPKIFSYQVYQDSTQLNCAPSYSFLKGLDKPNKATTILEAPIIIGWALQQ

GFYVVSSDHEGPRSSFIAGYEEGMAILDGIRALKNYAKLPTDSAIGFYGY

SGGAHATGWAANLAGSYAPEHNIIGAAYGGLPASARDTFNFLNKGAFAGF

AIAGVSGLALAYPDVETYIQSRLNAKGEKVFKQVRSRGFCIGQVVLTYPF

VDAYSLINDTNLLNEEPVASTLKSETLVQAEASYTVPVPKFPRFIWHALL

-continued

DEIVPFHSAATYVKEQCSKGADINWNVYSFAEHISAELFGLLPGLDWLNK

AYKGQAPKVPCGGGAQSVMGASGPPAQDVLGADLASQLRSLQGKPSAFGN

KPFGSISP, or a lipase variant thereof defined herein, i.e., further modifications, for example, point mutations, may be made to LipUMs sequence and the resulting amino acid sequence or protein is also a lipase variant.

In one embodiment, a lipUMs DNA polynucleotide sequence encompasses the following sequence:

(SEQ ID NO: 5)

ATGAGGTTCATTGCTGTTCGGGCTATCGTGACGCTAGCGGCTGCAGCCGC

CGTGTCGCTTGCAGTGCCCACAGAGCGAAGGGCAGCGTTCGCCGATCCAA

ACGACGATCTCTTCTACACCACGCCGGACAACATCAACACATATGCCAAT

GGTCAGGTCATCCAGTCACGCAAGGCTGATACCGATATTGGGAACAGCAA

CAAGGTTGAAGCTTTCCAGCTTCAATATCGCACTACCAATACGCAAAAGG

AGGCGCAGGCCAACGTTGCTACCGTATGGATCCCCAACAAGCCCGCTTCA

CCTCCCAAGATCTTCTCTTATCAGGTCTATCAGGACTCGACACAGCTCAA

CTGTGCTCCGAGCTATAGCTTTTTGAAGGGCCTTGACAAGCCTAACAAAG

CTACCACGATCCTCGAAGCACCCATCATCATCGGCTGGGCGCTCCAACAA

GGTTTCTACGTCGTCTCGTCTGATCACGAAGGCCCGCGCTCATCGTTCAT

TGCGGGCTACGAGGAAGGTATGGCTATTCTCGACGGCATACGTGCGCTCA

AGAACTACGCCAAACTGCCCACGGACAGCGCGATCGGCTTTTACGGATAC

AGCGGCGGTGCCCATGCAACCGGCTGGGCAGCTAATCTGGCAGGGAGCTA

CGCTCCTGAGCACAACATCATCGGTGCTGCCTACGGAGGACTGCCTGCTA

GCGCCAGAGACACATTCAACTTCCTCAACAAAGGCGCGTTTGCCGGCTTC

GCCATTGCGGGTGTCTCGGGTCTTGCGCTGGCCTACCCGGACGTGGAGAC

CTACATCCAGTCGCGCCTCAACGCCAAGGGAGAAAAGGTGTTTAAACAGG

TCCGAAGTCGCGGCTTCTGCATTGGCCAAGTGGTCCTAACCTACCCATTC

GTCGACGCCTATTCACTCATCAACGACACAAACCTTCTCAACGAGGAACC

GGTCGCCAGCACGTTGAAATCCGAGACGTTGGTTCAGGCCGAGGCTAGCT

ACACGGTTCCTGTTCCCAAATTCCCGCGTTTCATCTGGCATGCGCTCTTG

GACGAGATTGTTCCCTTCCACTCGGCTGCGACCTATGTCAAGGAGCAGTG

TTCAAAGGGCGCCGACATCAACTGGAATGTCTACTCATTTGCCGAGCACA

TCTCTGCCGAGCTTTTCGGCTTGCTGCCTGGTCTCGACTGGTTAAACAAG

GCTTACAAGGGTCAAGCACCCAAAGTGCCTTGTGGCGGAGGGGCTCAAAG

CGTGATGGGTGCCTCAGGCCCGCCTGCGCAGGACGTTCTGGGAGCTGACC

TGGCAAGCCAACTCCGATCTCTCCAGGGTAAGCCTTCTGCGTTTGGCAAC

AAACCTTTTGGCTCCATCTCCCCCTGA.

In another embodiment, the deletion of the N-terminus can start anywhere from about position M1 to about A34 and end around Q124. In yet another embodiment, the deletion of the N-terminus of SEQ ID NO:1 can start at about position M1 and end around position A145 (i.e., a M1_A145del mutant). In an embodiment, the variant lipase's sequence is essentially as set forth in SEQ ID NO:6:

(SEQ ID NO: 6)
MVPTERRAAFADPNDDLFYTTPDNINTYANGQVIQSRKADTDIGNSNKVE

AFQLQYRTTNTQKEAQANVATVWIPNKPASPPKIFSYQVYQDSTQLNCAP

SYSFLKGLDKPNKATTILEAPIIGWALQQGFYVVSSDHEGPRSSFIAGY

EEGMAILDGIRALKNYAKLPTDSAIGFYGYSGGAHATGWAANLAGSYAPE

HNIIGAAYGGLPASARDTFNFLNKGAFAGFAIAGVSGLALAYPDVETYIQ

SRLNAKGEKVFKQVRSRGFCIGQVVLTYPFVDAYSLINDTNLLNEEPVAS

TLKSETLVQAEASYTVPVPKFPRFIWHALLDEIVPFHSAATYVKEQCSKG

ADINWNVYSFAEHISAELFGLLPGLDWLNKAYKGQAPKVPCGGGAQSVMG

ASGPPAQDVLGADLASQLRLQGKPSAFGNKPFGSISP, or lipase variant thereof defined herein i.e., further modifications, for example, point mutations, may be made to SEQ ID NO:6 and the resulting amino acid sequence or protein is also a lipase variant. In the creation of SEQ ID NO:6, a starting sequence, i.e., methionine, has been added to the lipase variant encompassed by or essentially as set forth in SEQ ID NO:6.

In describing some lipase variants, the following nomenclature is used for ease of reference: multiple mutations are separated by plus signs, i.e., F145D+T217H, representing a double mutation that includes a phenylalanine-to-aspartate substitution at amino acid residue 145, and a threonine-to-histidine substitution at amino acid residue 214.

In another embodiment, the lipase variants include at least one or more deletions of the N-terminus of the *Ustilago maydis* lipase (i.e., lipUMf) and at least one amino acid substitution along the sequence length of the remaining portion of the lipase. For example, the lipase variant containing the amino acid sequence in SEQ ID NO:4 is further modified by a substitution of at least one amino acid along the length of SEQ ID NO:4. The additional substitution occurs at, near or facing the three-dimensional binding, active site or tunnel of the lipase, as described herein. The substitution(s) may be within about 15A of amino acid position A146 in the primary amino acid sequence of the lipUMs polypeptide, i.e., SEQ ID NO:4, for example at any of amino acid positions 135 through 165, 211 through 260 and 290 through 340. The substitution(s) may widen the access of the substrate to the binding, active site or tunnel of the lipase. Thus, substitutions may be located at one or more particular amino acid positions such as 145, 146, 211, 214, 217, 218, 233, 297, 301, 332 and 333 and/or any of positions 213 through 304 in the lipUMs primary amino acid sequence.

Some particular substitutions within the lipUMs sequence are, for example, F145D, A214N, T217H, F218S, V297H, L301N, G233A, G233Y, G233L and V297I. Those of ordinary skill in the art will understand that substitutions using similar amino acid properties will yield similar results. For example, T217H and T217R both result in a substitution of a polar amino acid for a positively charged amino acid and so similar results are contemplated and within the scope of this invention.

The lipase variant may optionally include substitutions of one or more additional amino acids. Such substitutions may be according to principles known to those of ordinary skill in the art. Table 1 illustrates exemplary mutations that have a deletion at the N-terminus of lipUMf, i.e., M1_Q124del, which results in the lipUMs sequence, and also has one or more specific substitutions along the lipUMs sequence i.e., F145D, A214N, etc.

TABLE 1

EXEMPLARY LIPASE VARIANT POLYPEPTIDES OF THE INVENTION

| Sequence Variation No. 1 for LipUMf | Sequence Variation No. 2 in resulting LipUMs | Sequence Variation No. 3 in resulting LipUMs | Sequence Variation No. 4 in resulting LipUMs | Sequence Variation No. 5 in resulting LipUMs | Sequence Variation No. 6 in resulting LipUMs | Sequence Variation No. 7 in resulting LipUMs | Sequence Variation No. 8 in resulting LipUMs |
|---|---|---|---|---|---|---|---|
| M1_Q124del | F145D | | | | | | |
| M1_Q124del+ | F145D+ | A214N | | | | | |
| M1_Q124del+ | F145D+ | A214N+ | T217H | | | | |
| M1_Q124del+ | F145D+ | A214N+ | T217H+ | F218S | | | |
| M1_Q124del+ | F145D+ | A214N+ | T217H+ | F218S+ | V297H | | |
| M1_Q124del+ | F145D+ | A214N+ | T217H+ | F218S+ | V297H+ | L301N | |
| M1_Q124del+ | F145D+ | A214N+ | T217H+ | F218S+ | V297H+ | L301N+ | G233A |
| M1_Q124del+ | A214N | | | | | | |
| M1_Q124del+ | A214N+ | T217H | | | | | |
| M1_Q124del+ | A214N+ | T217H+ | F218S | | | | |
| M1_Q124del+ | A214N+ | T217H+ | F218S+ | V297H | | | |
| M1_Q124del+ | A214N+ | T217H+ | F218S+ | V297H+ | L301N | | |
| M1_Q124del+ | A214N+ | T217H+ | F218S+ | V297H+ | L301N+ | G233A | |
| M1_Q124del+ | T217H | | | | | | |
| M1_Q124del+ | T217H+ | F218S | | | | | |
| M1_Q124del+ | T217H+ | F218S+ | V297H | | | | |
| M1_Q124del+ | T217H+ | F218S+ | V297H+ | L301N | | | |
| M1_Q124del+ | T217H+ | F218S+ | V297H+ | L301N+ | G233A | | |
| M1_Q124del+ | F218S | | | | | | |
| M1_Q124del+ | F218S+ | V297H | | | | | |
| M1_Q124del+ | F218S+ | V297H+ | L301N | | | | |
| M1_Q124del+ | F218S+ | V297H+ | L301N+ | G233A | | | |
| M1_Q124del+ | V297H | | | | | | |
| M1_Q124del+ | V297H+ | L301N | | | | | |
| M1_Q124del+ | V297H+ | L301N+ | G233A | | | | |
| M1_Q124del+ | L301N | | | | | | |
| M1_Q124del+ | L301N+ | G233A | | | | | |
| M1_Q124del+ | G233A | | | | | | |
| M1_Q124del+ | V297I | | | | | | |
| M1_Q124del+ | V297I + | F145D | | | | | |

TABLE 1-continued

EXEMPLARY LIPASE VARIANT POLYPEPTIDES OF THE INVENTION

| Sequence Variation No. 1 for LipUMf | Sequence Variation No. 2 in resulting LipUMs | Sequence Variation No. 3 in resulting LipUMs | Sequence Variation No. 4 in resulting LipUMs | Sequence Variation No. 5 in resulting LipUMs | Sequence Variation No. 6 in resulting LipUMs | Sequence Variation No. 7 in resulting LipUMs | Sequence Variation No. 8 in resulting LipUMs |
|---|---|---|---|---|---|---|---|
| M1_Q124del+ | V297I+ | A214N | | | | | |
| M1_Q124del+ | V297I+ | T217H | | | | | |
| M1_Q124del+ | V297I+ | F218S | | | | | |
| M1_Q124del+ | V297I+ | G233A | | | | | |
| M1_Q124del+ | V297I+ | F145D+ | A214N | | | | |
| M1_Q124del+ | V297I+ | F145D+ | A214N+ | T217H | | | |
| M1_Q124del+ | V297I+ | F145D+ | A214N+ | T217H+ | F218S | | |
| M1_Q124del+ | V297I+ | F145D+ | A214N+ | T217H+ | F218S+ | G233A | |
| M1_Q124del+ | G233Y | | | | | | |
| M1_Q124del+ | G233Y+ | F145D | | | | | |
| M1_Q124del+ | G233Y+ | A214N | | | | | |
| M1_Q124del+ | G233Y+ | T217H | | | | | |
| M1_Q124del+ | G233Y+ | F218S | | | | | |
| M1_Q124del+ | G233Y+ | V297I | | | | | |
| M1_Q124del+ | G233Y+ | V297H | | | | | |
| M1_Q124del+ | G233Y+ | F145D+ | A214N | | | | |
| M1_Q124del+ | G233Y+ | F145D+ | A214N+ | T217H | | | |
| M1_Q124del+ | G233Y+ | F145D+ | A214N+ | T217H+ | F218S | | |
| M1_Q124del+ | G233Y+ | F145D+ | A214N+ | T217H+ | F218S+ | V297I | |
| M1_Q124del+ | G233Y+ | F145D+ | A214N+ | T217H+ | F218S+ | V297H | |
| M1_Q124del+ | G233L | | | | | | |
| M1_Q124del+ | G233L+ | F145D | | | | | |
| M1_Q124del+ | G233L+ | A214N | | | | | |
| M1_Q124del+ | G233L+ | T217H | | | | | |
| M1_Q124del+ | G233L+ | F218S | | | | | |
| M1_Q124del+ | G233L+ | V297I | | | | | |
| M1_Q124del+ | G233L+ | V297H | | | | | |
| M1_Q124del+ | G233L+ | F145D+ | A214N | | | | |
| M1_Q124del+ | G233L+ | F145D+ | A214N+ | T217H | | | |
| M1_Q124del+ | G233L+ | F145D+ | A214N+ | T217H+ | F218S | | |
| M1_Q124del+ | G233L+ | F145D+ | A214N+ | T217H+ | F218S+ | V297I | |
| M1_Q124del+ | G233L+ | F145D+ | A214N+ | T217H+ | F218S+ | V297H | |

Table 1 presents some exemplary embodiments of double, triple, quadruple, quintuple, etc. mutants. For example, line 3 of Table 1 lists a M1_Q124del+F145D+A214N+T217H mutant that contains the following mutations: (1) the truncation of the N-terminus of the lipUMf sequence (M1_Q124del), which results in the amino acid sequence of lipUMs, (2) the phenylalanine-to-aspartic acid substitution at amino acid residue 145 in the resulting lipUMs sequence (F145D), (3) the alanine-to-asparagine substitution at amino acid residue 214 in the resulting lipUMs sequence (A214N), and (4) the threonine-to-histidine substitution at amino acid residue 217 in the resulting lipUMs sequence (T21711). If all of these mutations were stated in reference to the lipUMf sequence, the following notation would result: M1_Q124del+F269D+A338N+T341.

Similar mutants can be made when the N-terminus as encompassed in a M1_A145del mutant is removed, a starting sequence is added (i.e. such as a sequence as set forth in SEQ ID NO:6) and point mutations are made in similar locations in the sequence. For example, substitutions to SEQ ID NO:6 can include positions 2, 67, 70, 73, 74, 79, 153, 157, 188 and 189 and/or any of amino acid positions 69 through 160. Some particular point mutations can include A70N, T73H, F74S, V153H, L157N, G79A, G79Y, G79L and V153I. These exemplary mutations occur in any variation possible and encompass up to about eight sequence variations.

In another embodiment, the lipase variants include at least one or more deletions of the N-terminus of the *Ustilago maydis* lipase and removal, mutation or cleavage of the C-terminus sequence, which substantially comprises the flap structure of the lipase. This includes substitutions or frame insertions of a stop codon anywhere between about position 395 to about position 408 in the lipUMs sequence and/or between about position 251 to about position 264 in SEQ ID NO:6. Yet another embodiment encompasses these two sequence removals, plus any other mutation mentioned, including, but not limited to, the point mutations mentioned above, such as those listed in Table 1.

In some embodiments, the truncated versions of the lipase variant are at least about 50% substantially the full length of the parent lipase sequence, i.e. SEQ ID NO: 1. In some embodiments, the truncated versions of the lipase variant are at least about 60%, at least about 70% at least about 80%, or at least about 90%, at least about 95%, at least about 98% substantially the full length of the parent lipase sequence, i.e. SEQ ID NO:1. Truncation may occur at either the N-terminus or C-terminus, or both. Substantial homology or similarity can also be to the entire nucleic acid or amino acid sequence of the parent lipase or to fragments of these sequences. Certain embodiments thus also encompass polypeptide fragments of the variant lipases. Certain embodiments also encompass polypeptides having a lower degree of homology but having sufficient similarity so as to perform one or more of the same functions performed by the lipase parent, or variant thereof.

Fragments can retain one or more of the biological activities of the lipase or lipase variant protein and can comprise a domain or motif such as a catalytic site, active site, transmembrane domain, etc. Fragments can also be fused to create chimeric or fusion proteins. These can include a lipase sequence operably linked to another sequence not substantially homologous to the lipase. Such fusion proteins, for example, can facilitate the purification of a recombinant lipase protein or can enable secretion from certain host cells. Additionally, chimeric lipase proteins can be produced where one or more functional sites is derived from a different lipase member. In another embodiment and without being bound by any theory, the entire proposed sequence of the lipUMs that correlates to a proposed A10 helix structure, corresponding to essentially amino acid position 296 to about position 304, is substituted for the helix of another lipase, for example the A10 helix of CAL-A. The same helix exchange can occur in the sequence encompassed by SEQ ID NO:6, in that amino acids at essentially positions 152 through 160 can be substituted for the A10 helix of CAL-A. The lipase variant may include additional substitutions as listed above, such as those in Table 1, that are not present in the A10 helix of the lipUMs or SEQ ID NO:6 sequence as listed.

The methods of creating these chimeric or fusion proteins are well known to those of ordinary skill in the art.

Certain embodiments provide for nucleic acid sequences encoding the variant lipases of other embodiments, expression vectors harboring the nucleic acid sequences and transformed host cells containing the nucleic acid sequences and/or the expression vectors. The sequences of the parent lipase or lipase variants can be aligned with heterologous sequences, such as promoters, enhancers, transcriptional control elements, etc. in order to amplify or diminish their expression, as well as the expression of any co-factors.

Nucleic acid sequences, such as DNA, RNA, or cDNA, encoding the parent or variant lipases as defined herein may be isolated from any cell or organism producing them, by methods well known to those of ordinary skill in the art. Suitable nucleic acid sequences can be obtained by back-translation of the polypeptide sequence according to the genetic code. The codons used are preferably those frequently used in accordance with the usage within the specific organism, for example, *E. coli* or *P. pastoris*. Nucleic acid constructs containing the nucleic acid(s) of the present invention are also within the scope of the invention. These nucleic acid constructs will also contain regulatory sequences for expression, replication and/or recombination, in addition to the nucleic acid sequences encoding the parent or variant lipases.

Lipase variants can be naturally-occurring, made by recombinant means, or chemically synthesized (either in whole or in part) to provide the lipase polypeptide with useful characteristics. Useful variations can include, but are not limited to, increased hydrolysis or alcoholysis (i.e., ethanolysis), when in contact with a substrate, increased binding to a substrate, altered affinity for other molecules such as co-factors, recognition of a fatty acid moiety that is normally not recognized by the enzyme, increased preference for trans-fatty acids, increased preference for fatty acid substrates having fatty acid chain lengths greater than $C_{14}$, greater than about $C_{16}$, greater than about $C_{18}$, greater than $C_{20}$, greater than $C_{22}$, greater than $C_{24}$, greater than $C_{26}$, etc.

Host organisms that can be transformed by using the nucleic acid(s) of the present invention are also within the scope of the invention. Host organisms include, but are not limited to, unicellular or multicellular organisms, and preferably microorganisms. Cloning of the DNA sequence encoding the parent or variant lipase can involve inserting genomic DNA into an expression vector, such as a plasmid, in order to transform lipase-negative host cells. Expression vectors can express a portion of, or all of, the lipase polypeptides described herein. In one embodiment, host cells are eukaryotic cells. In another embodiment, host cells are prokaryotic.

In an embodiment, host cells are bacteria or yeast cells. In another embodiment, the bacterial host cells are *E. coli* cells and the yeast host cells are *P. pastoris* cells. The expression vector may be introduced into any host cell so that the protein, or portion thereof, can be expressed by the host cell. The protein can then be isolated from the cells by an appropriate purification method that is well known to one of ordinary skill in the art.

Many amino acids can be modified by processing, other post-translational modifications or other chemical modification methods well known by those of ordinary skill in the art before collection of the polypeptide. Modifications can include, but are not limited to, acetylation, acylation, ADP-ribosylation, amidation, covalent attachment of flavin, covalent attachment of a heme group, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-mRNA mediated addition of amino acids to proteins such as arginylation, and ubiquitination. Modification can occur anywhere in the protein, including the backbone, C- and N-termini, or the side chains and the various modifications can occur in more than one location.

Saturation mutagenesis and/or site-specific mutagenesis may be used to create the lipase variants as known to one of ordinary skill in the art (Zheng et al., 2004).

Yet another embodiment provides for a method of producing lipase variants by culturing the transformed host cells and recovering the lipase from the resulting culture or broth. In some instances, the entire transformed organism may be used, in others the lipase may be removed from the culture and purified before use. Alternatively, the lipase may be synthesized using known protein synthesis methods.

Still other embodiments provide for a method to increase the trans-selectivity of a lipase. In this method, the nucleic acid sequence encoding for the parent lipase is altered so that the encoded amino acid located at, near or facing a three-dimensional binding, active site or tunnel of the polypeptide is changed. This may result in increased relative accessibility of the substrate to the active site or increased difference in the activation energy needed for enzymatic turnover. The altered nucleic acid sequence is then introduced into a host cell, as described above. The host cell is then cultured under conditions to express the polypeptide variant lipase and the variant lipase is recovered from the culture. The activated catalyst composition containing at least one of the lipase variants described above is then contacted with a trans-fatty acid moiety containing substrate, such as, but not limited to, glycerides including butterfat, cocoa butter, cocoa butter substitutes, illipe fat, kokum butter, milk fat, mowrah fat, phulwara butter, sal fat, shea fat, borneo tallow, lard, lanolin, beef tallow, mutton tallow, tallow or other animal fat, canola oil, castor oil, coconut oil, coriander oil, corn oil, cottonseed oil, hazlenut oil, hempseed oil, linseed oil, mango kernel oil, meadowfoam oil, neat's foot oil, olive oil, palm oil, palm kernel oil, peanut oil, rapeseed oil, rice bran oil, safflower oil, sasanqua oil, soybean oil, sunflower seed oil, tall oil, tsubaki oil, vegetable oils, marine oils which can be converted into plastic or solid fats such as menhaden, candlefish oil, cod-liver oil, orange roughy oil, pile herd, sardine oil, whale and herring oils, 1,3-dipalmitoyl-2-monooleine (POP), 1(3)- palmitoyl-3(1)-stearoyl-2-monooleine (POSt), 1,3-distearoyl-2-monooleine (StOSt), glycerol, triglyceride, diglyceride, monoglyceride, behenic acid triglyceride, trioleine, tripalmitine, tristearine, palm olein, palm stearin, palm kernel olein, palm kernel stearin and triglycerides of medium chain fatty acids; or, processed partial or fully hydrogenated or fractionated oils thereof; esters including wax esters, alkyl esters, methyl esters, ethyl esters, isopropyl esters, octadecyl esters, aryl esters, propylene glycol esters, ethylene glycol esters, 1,2-propanediol esters and 1,3-propanediol esters; and fatty acids including saturated, unsaturated or polyunsaturated fatty acids. Preferably, the one or more fatty acids comprise carbon chains from 4 to 22 carbons long. Also preferably, the fatty acids are selected from the group consisting of palmitic acid, stearic acid, oleic acid, linoleic acid, linolenic acid, arachidonic acid, erucic acid, caproic acid, caprylic acid, capric acid, lauric acid, myristic acid, eicosapentaenoic acid (EPA), docosahexaenoic acid (DHA), 5-eicosenoic acid, butyric acid, γ-linolenic acid and conjugated linoleic acid. In preferred embodiments, substrates include edible oil compositions including, but not limited to vegetable, cooking or frying oil, such as corn oil, grape seed oil, nut oil such as hazelnut oil, linseed oil, safflower oil, sesame oil, olive oil, palm oil, soybean oil, canola oil, pumpkin seed oil, flax seed oil, sunflower oil, argan oil, rice bran oil, and the like, so as to hydrolyze the trans-fatty acid and/or long chain fatty acid moieties.

The activity can be measured by conventional procedures well known to those of ordinary skill in the art, such as hydrolysis and alcoholysis (i.e., ethanolysis), assays, turbidimetric assays, alkalimetric methods, colorimetric methods, and the like. In a particular embodiment, the inventors employed the modified method of hydrolysis and ethanolysis as set for in Examples 4 and 5.

Certain embodiments relate to the selective elimination or reduction of trans-unsaturated fatty acid compounds from a substrate containing such compounds by interaction of the above-mentioned variant lipases with the substrate so as to catalyze the breakdown of the trans-fatty acid moieties. Particular embodiments relate to the elimination of trans-unsaturated fatty acid moieties in triglycerides from edible liquid oils and are therefore related to the food technology industry. For example, these embodiments can eliminate or reduce the amount of trans-unsaturated fatty acid moieties in triglycerides from frying oils and frying oil systems.

The enzyme may be bound to a stable chemical surface away from the active site so as to create an enzyme bound filter through which the stable substrate is placed and filtered. Additionally, the enzyme may be immobilized in cells.

Another embodiment provides a method using the above-mentioned variant lipases for hydrolysis. One method of hydrolysis includes, but is not limited to, preparing the glyceride substrate as an emulsion in water or buffer (phosphate, 50 mM, pH 7.5) using gum arabic and shear mixed at 24000 rpm for 2 min (Ultra-Turrax® T-25 basic, IKA Labortechnik, Staufen, Germany). The substrate emulsion is then exposed to, by mixing or otherwise coming into contact with, at least one of the above-mentioned variant lipases, during which time the glyceride component is hydrolyzed to the free fatty acid component, until the desired percentage of hydrolysis has been achieved. The trans-rich free fatty acid component is then separated from the remaining glyceride component using conventional methods of separation such as washing or aqueous extraction, soap precipitation, crystallization, distillation, vacuum distillation or chromatography. The invention further relates to a method of reducing, or eliminating, trans-fatty acids from liquid oil stable enough for frying systems.

Another embodiment provides a method of using the above-mentioned variant lipases for alcoholysis, and preferably, for ethanolysis. Methods of ethanolysis include, but are not limited to, preparing the glyceride substrate as an emulsion in a mixture of ethanol and water (e.g., in a 1:1 ratio) using any conventional magnetic stirring equipment for a period of about 10 minutes. The substrate emulsion is then exposed to at least one of the above-mentioned variant lipases, during which time the glyceride component is ethanolysed to the ethyl ester component, until the desired percentage ethanolysis has been achieved. The trans-rich ethyl ester component is then separated from the remaining glyceride component using one or more conventional separation methods, including, without limitation, crystallization, distillation, vacuum distillation, chromatography, or any combination thereof.

Deposit of Biological Material:

The *P. pastoris* X-33 pPICZ(B)_lipUMs culture (designated herein as "lipUMs") has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action. The subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the finishing of a sample of the deposit, and in any case, for a period of at least 30 (thirty) years after the date of deposit or for the enforceable life of any patent which may issue disclosing the deposited culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

A deposit of *P. pastoris* pPICZ(B)_lipUMs was entered into the permanent collection of the Patent Depository of the Deutsche Sammlung von Mikroorganismen und Zellkulturen GmbH, located at Inhoffenstralβe 7B, 38124 Braunschweig, Germany, on Apr. 7, 2011 under the terms of the Budapest Treaty, whereupon it was assigned the DSMZ accession number 24702 by the repository. Viability of the subject culture was confirmed by the Depository on Apr. 12, 2011.

Exemplary Definitions

As used herein, the term "lipase(s)", "lipolytic enzyme(s)" or "lipase enzyme(s)" means a hydrolytic enzyme that acts to break down lipid substrates such as bacterial or fungal hydrolases and/or triacylglycerol hydrolases.

As used herein, the term "carboxylic acid moiety" means a fatty acid having a carboxyl group with an aliphatic tail or chain length of 2 or more carbons, which may be abbreviated herein as "Cn" or "$C_n$", wherein the number of carbon atoms is represented by n. For example, oleic acid is a carboxylic acid moiety having a chain length of 18 carbon atoms, which may be abbreviated as a chain length of C18:1Δ9, in which the 1Δ9 represents the presence of one double bond at the ninth carbon (C9).

As used herein, the term "homology" is an indicator of the degree of identical elements between biological sequences, for example, the percent of identical amino acids between two aligned protein sequences. Gaps can be introduced into one or both of a first and a second amino acid or nucleic acid sequence for optimal alignment and non-homologous sequences may be disregarded for comparison purposes. As used herein, the term "similarity" is an indicator of the degree of similarity between biological sequences, for example, the percent of similar amino acids with similar functions and/or structures at similar positions between two aligned protein sequences.

As used herein, the term "variant" means a lipase derived from a *Ustilago maydis* lipase, or a naturally occurring variant. Typically, the variant differs from the native *Ustilago maydis* lipase by one or more amino acid residues, which may have been added, deleted or inserted at one or more sites within the amino acid sequence of the *Ustilago maydis* lipase, or substituted at one or more amino acid residues by another non-native amino acid residue.

As used herein, the terms "active," "biologically active," and "activity" mean biological activity associated with a particular protein or amino acid sequence and are used interchangeably herein. For example, the enzymatic activity associated with a lipase is hydrolysis and/or alcoholysis, i.e., ethanolysis, so as to hydrolyze or esterify at least a portion of a trans-fatty acid or carboxylic acid moiety. Lipase activity is measured as the ability to hydrolyze and/or esterify at least a portion of a trans-fatty acid or carboxylic acid moiety.

Certain embodiments also encompass DNA sequences that are complementary, or essentially complementary, with one or more of the specific sequences set forth herein. Nucleic acid sequences that are "complementary" are those that are capable of base pairing according to the standard Watson-Crick complementarity rules. As used herein, the term "complementary sequences" means nucleic acid sequences that are substantially complementary, as may be assessed by the same nucleotide comparison set forth above, or are defined as being capable of hybridizing to one or more of the specific nucleic acid segments disclosed herein under relatively stringent conditions such as those described immediately above.

The term "a sequence essentially as set forth in SEQ ID NO:X" means that the sequence substantially corresponds to at least a first portion of SEQ ID NO:X and has relatively few nucleotides that are not identical to, or a biologically functional equivalent of, the nucleotides of SEQ ID NO:X. Accordingly, sequences that have about 85% to about 90%; about 91% to about 95%; or about 96% to about 99% of nucleotides that are identical or functionally equivalent to one or more of the nucleotide sequences provided herein are particularly contemplated to be useful in the practice of the invention. In the context of peptides, polypeptides, and proteins, the term "a sequence essentially as set forth in SEQ ID NO:X" means that the sequence substantially corresponds to at least a first portion of SEQ ID NO:X and has relatively few amino acid residues that are not identical to, or a biologically functional equivalent of, the amino acid residues of SEQ ID NO:X. The term "biologically functional equivalent" is well understood by one of ordinary skill in the art, and is further defined in detail herein. Accordingly, peptide, polypeptide, or protein sequences that have about 85% to about 90%; about 91% to about 95%; or about 96% to about 99% of the amino acids that are identical or functionally equivalent to one or more of the amino acid sequences provided herein are particularly contemplated to be useful in the practice of the invention.

As used herein, the term "primer" refers to a single-stranded oligonucleotide that acts as a point of initiation of template-directed DNA synthesis using well-known methods (e.g. PCR) including, but not limited to those described herein. The appropriate length of a primer depends on its particular use, but typically ranges from about 15 to about 30 nucleotides.

As used herein, the term "expression" means the biological production of a product encoded by a coding sequence. In most cases, a polynucleotide (i.e., DNA) sequence, including the coding sequence, is transcribed to form a messenger-RNA (mRNA). The messenger-RNA is then translated to form a polypeptide product that has a relevant biological activity. The process of expression may involve further processing steps to the RNA product of transcription, such as splicing to remove introns, and/or post-translational processing of a polypeptide product.

As used herein, the term "heterologous" is used in relation to a predetermined referenced gene sequence. For example, with respect to a structural gene sequence, a heterologous promoter is defined as a promoter that does not naturally occur adjacent to the referenced structural gene, but which is positioned by laboratory manipulation. Likewise, a heterologous gene or nucleic acid segment or sequence is defined as a gene or segment that does not naturally occur adjacent to the referenced promoter and/or enhancer elements. Similarly, the term "heterologous" is also used in relation to a predetermined amino acid sequence. For example, with respect to an amino acid sequence, a heterologous protein tag, such as a polyhistidine tag, is defined as a peptide sequence that does not naturally occur adjacent to the referenced amino acid sequence. Likewise, a heterologous amino acid segment or sequence is defined as a segment or sequence that does not naturally occur adjacent to the referenced tag. Additionally, a heterologous protein refers to a protein that is not natively produced by or found within a particular organism. This can occur, for example, by the cloning and expression of a non-native lipase gene in a host organism such as *E. coli*.

As used herein, the term "operably linked" means a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and within a reading frame. Since enhancers generally function when separated from the promoter by several kilobases and intronic sequences may be of variable lengths; however, some polynucleotide elements may be operably linked but not contiguous.

The phrases "isolated" or "biologically pure" means material that is substantially, or essentially, free from components that normally accompany the material as it is found in its native state. Thus, an embodiment provides that the isolated peptides do not contain materials normally associated with the peptides in their in situ environment.

"Link" or "join" means any method well known by those of ordinary skill in the art for functionally connecting two or more molecules, including, without limitation, recombinant fusion, covalent bonding, disulfide bonding, ionic bonding, hydrogen bonding, electrostatic bonding, and such like.

As used herein, the term "polypeptide" means a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain,"

and "contiguous amino acid sequence" are all encompassed within the definition of a "polypeptide," and the term "polypeptide" can be used instead of or interchangeably with, any of these terms. The term further includes polypeptides that have undergone one or more post-translational modification(s), including, without limitation, glycosylation, acetylation, phosphorylation, amidation, derivatization, proteolytic cleavage, post-translation processing, or modification by inclusion of one or more non-naturally occurring amino acids. Throughout the disclosure, common one-letter and three-letter amino acid abbreviations have been employed following the conventional nomenclature in the art: Alanine (A; Ala), Arginine (R; Arg), Asparagine (N; Asn), Aspartic Acid (D; Asp), Cysteine (C; Cys), Glutamine (Q; Gln), Glutamic Acid (E; Gln), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained. All amino-acid residue sequences represented herein conform to the conventional left-to-right amino-terminus to carboxy-terminus orientation.

The term "protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is intended to refer to any amino acid chain length, including those of short peptides from about 2 to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules, including at least one amino acid polymer. Polypeptides and proteins of the present invention also include polypeptides and proteins that are or have been post-translationally modified, and include any sugar or other derivative(s) or conjugate(s) added to the backbone amino acid chain.

As used herein, the term "substantially free" or "essentially free" in connection with the amount of a component means a composition that contains less than about 10 weight percent, less than about 5 weight percent, and less than about 1 weight percent of a compound. In an embodiment, these terms refer to less than about 0.5 weight percent, less than about 0.1 weight percent, or less than about 0.01 weight percent.

As used herein, the term "substantially homologous" encompasses sequences that are similar to the identified sequences, such that antibodies raised against peptides having the identified sequences will specifically bind to (e.g., cross-react with) peptides having the substantially homologous sequences. In some variations, the amount of detectable antibodies induced by the homologous sequence is identical to the amount of detectable antibodies induced by the identified sequence. In other variations, the amounts of detectable antibodies induced are substantially similar, thereby providing immunogenic properties. For example, homologous can refer to at least about 75%, at least about 80% identical and "substantially homologous" can refer to at least about 85% or at least about 90% identity, at least about 95%, at least about 97% identical, at least about 98% identical, at least about 99% identical, and at least substantially or entirely 100% identical (i.e., "invariant"). When one or more amino acid residues in the lipase or lipase variant are mutated by substitution of a conservative amino acid, two or more peptides may have substantially similar activity and therefore be considered homologous or substantially homologous.

As used herein, the term "substrate" means a chemical compound that can be catalyzed by lipases. For example, alcohols, amines, amino esters, amides, carboxylic acid esters, thioesters, thiols, cyanohydrins, cyanohydrin esters, and meso-diols and their sterioisomers may be substrates.

The term "for example" or "e.g.," as used herein, means by way of example, without limitation intended, and should not be construed as referring only those items explicitly enumerated in the specification.

In accordance with long standing patent law convention, the words "a" and "an" when used in this application, including the claims, denote "one or more."

EXAMPLES

The following examples are included to demonstrate illustrative embodiments of the invention. It should be appreciated by those of ordinary skill in the art that the techniques disclosed in the examples that follow represent techniques discovered by the inventors to function well in the practice of the invention, and thus can be considered to constitute modes for its practice. However, those of ordinary skill in the art should, in light of the present disclosure, appreciate that many changes can be made in the specific embodiments that are disclosed and still obtain a like or similar result without departing from the spirit and scope of the invention.

Example 1

Sequence and Structure of LipUMf and LipUMs

In Silico Analysis of DNA and Amino Acid Sequences

The INTEGR8 database of the European Bioinformatics Institute (EBI) has access to complete genomes and proteomes and was searched for putative lipases within the *Ustilago maydis* genome. In order to identify possible open reading frames ("ORF") in the DNA sequence of lipUM, the ORF Finder software from the NCBI was employed (National Center for Biotechnology Information, National Library of Medicine, Bethesda, Md., USA). Structure based alignments were performed using the "PSI-Nature Structural Genomics Knowledgebase" (Berman et al., 2009). Protein data bank searches were performed with the Distance matrix ALIgnment Server (DALI) of the European Bioinformatics Institute (EBI) (Holm and Sander, 1993). Signal peptides were predicted using SignalP 3.0 server (Bendtsen, et al., 2004). Transmembrane domain prediction and protein localization were performed with the TMHMM 2.0 server algorithm (Krogh et al., 2001) and the TargetP 1.1 server (Emanuelsson et al., 2000), which can be accessed by the CBS prediction servers website.

Molecular Modeling

Molecular modeling was performed using YASARA version 7.11.28 (YASARA Bioscience, Graz, AU). Graphical representations were done with the PyMOL® visualization software, version 0.99rc6 (DeLano Scientific LLC, CA, USA). LipUMs was visualized with modeled cis- and trans-fatty acid isomers and was based on energy minimizations with YASARA applying the standard force field for energy-minimization calculations and Molecular Dynamics (MD) simulations (YASARA Biosciences GmbH, Vienna, Austria). Energy minimizations were performed by using the Powell method (Powell, 1977). All crystal structure coordinates were obtained from the Research Collaboratory for Structural Bioinformatics (RCSB) Protein Data Bank available on their website (Piscataway, N.J.; La Jolla, Calif.; Madison, Wis.; USA).

Table 2 shows a comparison of the size, length, and homology of the full sequence of lipUM (hereinafter "lipUMf") and the shortened sequence of lipUM (hereinafter "lipUMs") with the N-terminus of lipUMf removed.

3guu) and lipUMf is 69%. There are no gaps in the alignment apart from one amino acid at the very far C-terminus of lipUMf. Models based on a target-template sequence alignment higher than 50% sequence identity typically have the correct fold and the alignments tends to be mainly correct. Structural variation in templates and incorrect reconstruction of loops (insertions and deletions) are the main sources of model inaccuracies. (Fiser et al., 2000; Zhang, 2009).

TABLE 2

COMPARISON OF SIZE, LENGTH AND HOMOLOGY OF EXEMPLARY LIPUMF AND LIPUMS

| Lipase | Number of amino acids | Sequence homology to CAL-A [%] | Probability of presence of a N-terminal signal sequence (Target P 1.1) | Probability for certain signal sequence cleavage site (SignalP 3.0) | Prediction of possible transmembrane segments (TMS) within the sequence (TMHMM 2.0) |
|---|---|---|---|---|---|
| lipUMf | 582 | 69 | 0.6 | GIA-RS (88%) | 2 TMS possible |
| lipUMs | 458 | 69 | 0.9 | SLA-VP (100%) | 0 |

GIA-RS refers to amino acid positions 32 through 36 of the lipUMf sequence, where potential cleavage by the signal peptidase may occur during protein processing. SLA-VP refers to amino acid positions 19 through 23 of the lipUMs sequence, where potential cleavage by the signal peptidase may occur during protein processing. The hyphen in each case indicates the position where the cleavage would likely occur, according to the software.

Sequence analysis reveals that the N-terminus of the lipUM polypeptide (SEQ ID NO:1) is about 124 amino acids longer than that of the lipUMs polypeptide (SEQ ID NO:3). Analysis of the lipUM polypeptide sequence with the TMHMM version 2.0 program predicted the presence of two transmembrane segments (TMS), the first of which could be a signal sequence, as suggested by the TMHMM, TargetP version 1.1 and SignalP version 3.0 programs. Such structure has been found in other lipases, such as the lipase from the fungus Rhizopus oryzae.

In addition, an ArgArg dipeptide was found within the lipUM sequence. A possible alternative signal sequence can be placed about 40 amino acids upstream of this dipeptide. The alternative signal sequence of lipUM has all the characteristics of a sec-dependent signal sequence (von Heijne, 1985).

FIG. 1 is a schematic representation of the possible structures of the two lipUM variants: the full sequence, i.e., lipUMf, and the short form of lipUMf, i.e., lipUMs. Therefore, lipUMs contains a signal peptidase cleavage site, and a Kex2 cleavage site. Kexin-like proteinases are a subfamily of the subtilisin-like serine proteinases with multiple regulatory functions in eukaryotes and catalyze or cleave proteins at the Kex2 cleavage site. Site-specific proteolysis is a feature in protein maturation and plays a crucial role in activation of many enzymes (and in the generation of peptide hormones). In the late secretory pathway of eukaryotic cells this mechanism is mainly mediated by kexin-like proteinases.

Figure 12:
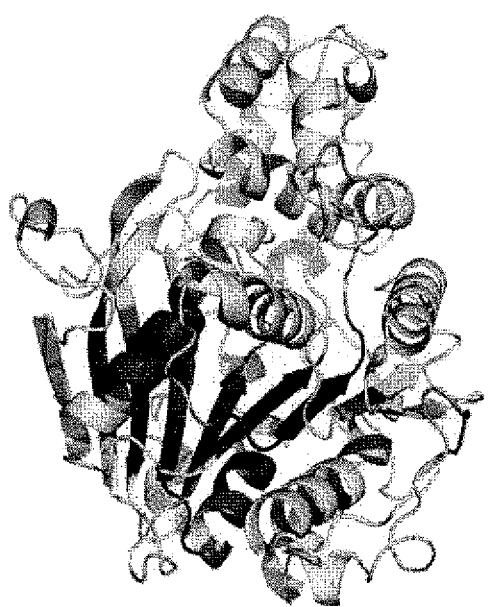
FIG. 12 shows a homology model of amino acids 152 to 582 of lipUMf as compared to CAL-A.

FIG. 12 is a homology model made with the Swissmodel online suite, accessible via the ExPASy web server (Swiss Institute of Bioinformatics, Lausanne, Switzerland). The model is based on the target-template alignment of CAL-A (pdb 3guu) and the full length sequence of lipUMf (UniProt Accession Q4P903; Kemper et al., 2006). 430 amino acids of the 582 amino acids of lipUMf can be aligned to the CAL-A amino acid sequence found in the pdb-file 3guu chain B (2.10 Å). The identity between these two sequences (CAL-A (pdb Example 2

The Functional Expression of CAL-A, LipUMf and LipUMs E. Coli and P. pastoris

CAL-A, lipUMf and lipUMs, and variants thereof were cloned and functionally expressed in E. coli cells. Synthetic DNA sequences of each of the enzymes were codon-optimized for expression and subcloned into pET-22b(+) expression vectors (Novagen®, EMD4Biosciences, Gibbstown, N.J., USA).

CAL-A and lipUMs, and variants thereof were also cloned and functionally expressed in P. pastoris cells.

Gene Synthesis and Subcloning of lipUMf, lipUMs and Variants Thereof

For gene synthesis and subcloning of CAL-A into E. coli, the nucleotide sequence of CAL-A was derived from the amino acid sequence published by Hoegh et al. (1995). For expression of CAL-A, its sequence was codon optimized by GENEART® with the software "GeneOptimizer®" (Geneart AG Corp., Regensburg, Germany). A composite plasmid named pGA15-pproCAL-Aop carried the codon optimized full length, i.e., containing the signal pre-pro amino acid sequence, CAL-A sequence. This plasmid was used as the template in a polymerase chain reaction (PCR) for subcloning the CAL-A gene into the pET-22b(+) expression vector (Novagen®, EMD4Biosciences, Gibbstown, N.J., USA) and the codon-optimized CAL-A contained a histidine (His) tag for detection and purification purposes, the sequence of which is reflected in SEQ ID NO:7:

```
                                          (SEQ ID NO: 7)
ATGCGTGTGAGCCTGCGTAGCATTACCAGCCTGCTGGCTGCGGCAACCGC

AGCAGTTCTGGCTGCGCCGGCAGCGGAAACCCTGGATCGTCGTGCGGCGC

TGCCGAATCCGTATGATGATCCGTTTTATACCACCCCGAGCAACATTGGC

ACCTTTGCGAAAGGCCAGGTGATTCAGAGCCGTAAAGTGCCGACCGATAT

TGGCAACGCGAACAACGCGGCGAGCTTTCAGCTGCAATATCGTACCACCA

ACACCCAGAACGAAGCGGTGGCGGATGTGGCGACCGTGTGGATTCCGGCG

AAACCGGCGAGCCCGCCGAAAATTTTTAGCTACCAGGTGTATGAAGATGC

GACCGCGCTGGATTGCGCGCCGAGCTATAGCTATCTGACCGGCCTGGATC
```

```
AGCCGAACAAAGTGACCGCGGTGCTGGATACCCCGATTATTATTGGCTGG

GCGCTGCAACAGGGCTATTATGTGGTGAGCAGCGATCATGAAGGCTTTAA

AGCGGCGTTTATTGCGGGCTATGAAGAAGGCATGGCGATTCTGGATGCA

TTCGTGCGCTGAAAAACTATCAGAACCTGCCGAGCGATAGCAAAGTGGCG

CTGGAAGGCTATAGCGGCGGTGCGCACGCGACCGTTTGGGCGACCAGCCT

GGCCGAAAGCTATGCGCCGGAACTGAACATTGTGGGCGCGAGTCATGGTG

GCACCCCGGTGAGCGCGAAAGATACCTTTACCTTTCTGAACGGCGGTCCG

TTTGCGGGTTTTGCGCTGGCCGGTGTGAGCGGTCTGAGCCTGGCCCATCC

GGATATGGAAAGCTTTATTGAAGCGCGTCTGAACGCGAAAGGTCAGCGTA

CCCTGAAACAAATTCGTGGCCGTGGCTTTTGCCTGCCGCAGGTGGTGCTG

ACCTATCCGTTTCTGAACGTGTTTAGCCTGGTGAACGATACCAACCTGCT

GAACGAAGCGCCGATTGCGAGCATTCTGAAACAGGAAACCGTTGTTCAGG

CGGAAGCGAGCTATACCGTGAGCGTGCCGAAATTTCCGCGTTTTATTTGG

CATGCGATTCCGGATGAAATTGTGCCGTATCAGCCGGCAGCGACCTATGT

GAAAGAACAGTGCGCGAAAGGCGCGAACATTAACTTTAGCCCGTATCCGA

TTGCGGAACATCTGACCGCGGAAATTTTTGGCCTGGTGCCGAGCCTGTGG

TTTATTAAACAGGCGTTTGATGGCACCACCCCGAAAGTGATTTGCGGCAC

CCCGATTCCGGCGATTGCGGGCATTACCACCCCGTCTGCGGATCAGGTGC

TGGGCAGCGATCTGGCCAACCAGCTGCGTAGCCTGGATGGCAAACAGAGC

GCGTTTGGCAAACCGTTTGGCCCGATTACCCCGCCGTAA.
```

In the PCR, the following oligonucleotides were used to amplify the whole CAL-A sequence:

```
Forward primer:
                                           (SEQ ID NO: 8)
5'-TAAGGTACCATATGCGTGTGAGCCT-3'
and Reverse primer:
                                           (SEQ ID NO: 9)
5'-TAAGAATGCGGCCGCCGGCGGGGTAATCGGGCC-3'.
```

The PCR product was cut with the restriction enzymes NdeI and NotI (Fermentas® St. Leon-Rot, Germany) and ligated into the correspondingly-digested pET22b(+) vector using standard procedures known to one of ordinary skill in the art.

Subcloning of lipUMs and lipUMf were performed using GENEART® software analysis. The genes of lipUMs and lipUMf were codon optimized for *E. coli*, newly synthesized, and subcloned into the pET22b(+) vector via NdeI and NodI restriction sites, respectively. A composite plasmid named pET22-lipUMsophis carried the codon optimized lipUMs sequence. A composite plasmid named pET22-lipUMfophis carried the codon optimized lipUMf sequence. These plasmids were used as the templates in a polymerase chain reaction (PCR) for subcloning both the lipUMs and lipUMf gene into the pET-22b(+) expression vector (Novagen®, EMD Chemicals, Gibbstown, N.J., USA) which contained a $P_{T7}$ promoter and histidine (His) tag for detection and purification purposes.

The codon-optimized DNA sequence encoding the lipUMf polypeptide used for cloning into *E. coli* included the following sequence:

```
                                          (SEQ ID NO: 10)
ATGTGGGGTCGTATTCGTAATGTTATTCAGCCGACCTGGGCACCTCCGCT

GTTTGGCACCCTGAATATTATTTTTAGCCTGTTTTTTCGTGCAGGTATTG

CACGTAGCCATAAATGGACCTGGTGTTGTTATCGTCCGACCCGTATGGCA

CGTAGCCGTACCTTTAGCAATAGCGCACCGACCCGTCGTCGTCCGGAACG

TCTGCGTCTGCAGAAAGGTAGCAGCAATACCACCATTCGTCCGCGTCCGA

GCGCAATTCTGCCGGATGAAATGAATCATGGTAGCCTGCTGACCGTTGTT

CCGCATACCGTTGTTGCAAGCACCCCGAGCTTTCGTAGCAGCTTTCCGGA

TAGCCTGATTGCAAGCGTTCAGATGCGTTTTATTGCAGTTCGTGCCATTG

TTACCCTGGCAGCAGCAGCAGCCGTTAGCCTGGCAGTTCCGACCGAACGT

CGTGCAGCATTTGCAGATCCGAATGATGACCTGTTCTATACCACACCGGA

TAACATCAACACCTATGCCAATGGCCAGGTTATTCAGAGCCGTAAAGCCG

ATACCGATATTGGCAATAGCAATAAAGTGGAAGCATTTCAGCTGCAGTAT

CGTACCACCAATACCCAGAAAGAAGCACAGGCCAACGTTGCAACCGTTTG

GATTCCGAATAAACCGGCATCTCCTCCGAAAATTTTTAGCTATCAGGTGT

ATCAGGATAGCACCCAGCTGAATTGTGCACCGAGCTATAGCTTTCTGAAA

GGTCTGGATAAACCGAATAAAGCAACCACCATTCTGGAAGCACCGATTAT

TATTGGTTGGGCACTGCAGCAGGGTTTTATGTTGTTAGCAGCGATCATG

AAGGTCCGCGTAGCTCTTTTATTGCCGGTTATGAAGAAGGTATGGCCATT

CTGGATGGTATTCGTGCCCTGAAAAATTATGCAAAACTGCCGACCGATAG

CGCAATTGGTTTTTATGGTTATAGCGGTGGTGCACATGCAACCGGTTGGG

CAGCAAATCTGGCAGGTAGCTATGCACCGGAACATAATATTATTGGTGCA

GCCTATGGTGGTCTGCCTGCAAGCGCACGTGATACCTTTAATTTTCTGAA

TAAAGGTGCCTTTGCAGGTTTTGCAATTGCCGGTGTTAGCGGTCTGGCAC

TGGCATATCCGGATGTGGAAACCTATATTCAGTCTCGCCTGAATGCAAAA

GGCGAAAAAGTGTTTAAACAGGTTCGTAGCCGTGGTTTTTGTATTGGTCA

GGTGGTTCTGACCTATCCGTTTGTTGATGCCTATAGCCTGATTAATGATA

CCAATCTGCTGAATGAAGAACCGGTTGCCAGCACCCTGAAAAGCGAAACC

CTGGTTCAGGCAGAAGCAAGCTATACCGTTCCGGTTCCGAAATTTCCGCG

TTTTATTTGGCATGCACTGCTGGATGAAATTGTTCCGTTTCATAGCGCAG

CAACCTATGTTAAAGAACAGTGTAGCAAAGGTGCCGATATTAATTGGAAT

GTGTATAGCTTTGCCGAACATATTAGCGCAGAACTGTTTGGTCTGCTGCC

TGGTCTGGATTGCTGAATAAAGCCTATAAAGGTCAGGCACCGAAAGTTC

CGTGTGGTGGTGGTGCACAGAGCGTTATGGGTGCAAGCGGTCCTCCGGCA

CAGGATGTTCTGGGTGCAGATCTGGCAAGCCAGCTGCGTAGCCTGCAGGG

TAAACCGAGCGCATTTGGCAATAAACCGTTTGGTAGCATTTCTCCTGCGG

CCGCACTCGAGCACCACCACCACCACCACTGA.
```

The codon-optimized DNA sequence encoding the lipUMs polypeptide used for cloning into *E. coli* included the following sequence:

(SEQ ID NO: 11)
ATGCGTTTTATTGCCGTTCGTGCAATTGTTACCCTGGCTGCAGCAGCAGC

AGTTAGCCTGGCCGTTCCGACCGAACGTCGTGCAGCATTTGCAGATCCGA

ATGACGACCTGTTTTATACCACACCGGATAACATCAATACCTATGCGAAT

GGTCAGGTTATTCAGAGCCGTAAAGCCGATACCGATATTGGCAATAGCAA

TAAAGTGGAAGCATTTCAGCTGCAGTATCGTACCACCAATACCCAGAAAG

AAGCACAGGCAAACGTCGCAACAGTTTGGATTCCGAATAAACCGGCAAGC

CCTCCGAAAATTTTTAGCTATCAGGTGTATCAGGATAGCACCCAGCTGAA

TTGTGCACCGAGCTATAGCTTTCTGAAAGGTCTGGATAAACCGAATAAAG

CAACCACCATTCTGGAAGCACCGATTATTATTGGTTGGGCACTGCAGCAG

GGTTTTTATGTTGTTAGCAGCGATCATGAAGGTCCGCGTAGCAGCTTTAT

TGCAGGTTATGAAGAAGGTATGGCCATTCTGGATGGTATTCGTGCCCTGA

AAAATTATGCAAAACTGCCGACCGATAGCGCAATTGGTTTTTATGGTTAT

AGCGGTGGTGCACATGCAACCGGTTGGGCAGCAAATCTGGCTGGTAGCTA

TGCACCGGAACATAATATTATTGGTGCAGCCTATGGTGGTCTGCCTGCCA

GCGCACGTGATACCTTTAATTTTCTGAATAAAGGTGCCTTTGCAGGTTTT

GCAATTGCAGGTGTTAGCGGTCTGGCCCTGGCCTATCCGGATGTTGAAAC

CTATATTCAGTCTCGCCTGAATGCAAAAGGCGAAAAGTGTTTAAACAGG

TTCGTAGCCGTGGTTTTTGTATTGGTCAGGTGGTTCTGACCTATCCTTTT

GTTGATGCCTATAGCCTGATTAATGATACCAATCTGCTGAATGAAGAACC

GGTTGCAAGCACCCTGAAAAGCGAAACCCTGGTTCAGGCAGAAGCAAGCT

ATACCGTTCCGGTTCCGAAATTTCCGCGTTTTATTTGGCATGCACTGCTG

GATGAAATTGTTCCGTTTCATAGCGCAGCAACCTATGTTAAAGAACAGTG

CTCTAAAGGTGCCGATATTAATTGGAATGTGTATAGCTTTGCCGAACATA

TTAGCGCAGAGCTGTTTGGTCTGCTGCCTGGTCTGGATTGGCTGAATAAA

GCCTATAAAGGTCAGGCACCGAAAGTTCCGTGTGGTGGTGGTGCACAGAG

CGTTATGGGTGCAAGCGGTCCTCCGGCACAGGATGTTCTGGGTGCAGATC

TGGCCAGCCAGCTGCGTAGCCTGCAGGGTAAACCGAGCGCATTTGGCAAT

AAACCGTTTGGTAGCATTTCTCCTGCGGCCGCACTCGAGCACCACCACCA

CCACCACTGA.

The open reading frames encoding lipUMs and lipUMf were also codon optimized by GENEART® for subcloning into *P. pastoris*. The *P. pastoris* codon-optimized lipUMs and lipUMf nucleotide sequences were inserted into the pPICZ B vector (Invitrogen®, Carlsbad, Calif., USA) and included a His tag for detection and purification purposes when performing PCR. The codon-optimized DNA sequence encoding the lipUMf polypeptide used for cloning into *P. pastoris* included the following sequence:

(SEQ ID NO: 12)
ATGTGGGGCCGTATCCGTAATGTCATCCAGCCTACCTGGGCACCGCCTTT

GTTTGGCACCCTGAATATCATCTTTAGCCTGTTCTTTCGTGCGGGTATTG

CTAGATCTCATAAGTGGACTTGGTGTTGCTATAGACCAACACGCATGGCG

CGCTCCCGTACGTTTAGCAACAGTGCTCCAACCCGTAGACGCCCGGAAAG

ACTGCGCTTGCAGAAAGGATCTTCCAACACCACTATCCGTCCGAGACCTT

CTGCCATTCTGCCTGATGAAATGAATCATGGTTCCCTGTTGACCGTTGTG

CCACACACTGTCGTTGCGTCAACACCTAGCTTTAGATCAAGCTTCCCAGA

TAGTTTGATTGCTTCTGTTCAAATGCGCTTTATCGCCGTTCGTGCAATTG

TTACCCTGGCTGCCGCAGCGGCTGTCTCCTTGGCGGTTCCAACCGAACGT

AGAGCCGCATTTGCTGATCCGAACGATGACCTGTTCTATACAACGCCTGA

CAACATCAATACGTACGCCAATGGCCAGGTCATTCAATCCCGTAAGGCAG

ATACCGACATCGGAAACTCAAACAAAGTGGAAGCTTTCCAGCTGCAATAC

AGAACCACTAATACTCAGAAGGAGGCCCAAGCAAACGTGGCCACAGTCTG

GATTCCTAATAAGCCAGCATCTCCACCGAAAATCTTTTCCTATCAGGTTT

ACCAAGATTCTACTCAGCTGAACTGTGCCCCGTCTTATTCCTTCCTGAAA

GGTTTGGACAAACCAAATAAGGCGACAACGATTCTGGAAGCTCCGATTAT

CATTGGTTGGGCATTGCAGCAAGGCTTTTACGTGGTCAGTTCTGATCATG

AGGGTCCGAGATCCTCATTCATTGCCGGCTATGAAGAGGGAATGGCAATC

TTGGATGGCATTCGCGCGCTGAAGAACTACGCTAAATTGCCTACTGACAG

TGCCATTGGCTTTTATGGATACTCTGGTGGCGCGCATGCTACAGGATGGG

CGGCTAACCTGGCCGGTTCATATGCACCGGAACACAATATCATTGGTGCT

GCATATGGAGGTCTGCCTGCAAGCGCACGCGATACTTTTAACTTCTTGAA

CAAAGGAGCGTTTGCTGGCTTCGCCATTGCTGGTGTGTCAGGCCTGGCGT

TGGCTTATCCTGACGTCGAAACCTACATCCAAAGCCGTCTGAATGCTAAA

GGAGAGAAGGTGTTTAAACAGGTCCGCAGTCGTGGATTCTGCATTGGTCA

AGTTGTGCTGACTTATCCTTTTGTTGATGCCTACTCTTTGATCAACGACA

CAAATCTGTTGAACGAAGAGCCAGTTGCATCCACGTTGAAGTCAGAAACC

CTGGTGCAGGCCGAGGCATCTTATACTGTCCCAGTTCCGAAATTTCCACG

TTTCATCTGGCATGCGCTGTTGGATGAAATTGTTCCGTTCCACAGCGCGG

CTACCTATGTGAAGGAGCAATGTAGTAAAGGTGCTGACATTAACTGGAAT

GTTTACTCATTTGCCGAACACATCAGCGCAGAGCTGTTCGGCCTGTTGCC

GGGACTGGATTGGTTGAATAAGGCGTACAAAGGCCAGGCTCCGAAAGTCC

CTTGCGGCGGAGGTGCTCAAAGCGTTATGGGAGCCAGTGGTCCTCCAGCA

CAGGATGTGCTGGGTGCGGACTTGGCTTCTCAACTGCGTAGCCTGCAAGG

TAAACCATCAGCATTCGGTAACAAACCATTCGGAAGTATCTCCCCGGCGG

CCGCCAGCTTTCTAGAACAAAAACTCATCTCAGAAGAGGATCTGAATAGC

GCCGTCGACCATCATCATCATCATCATTGA.

The codon-optimized DNA sequence encoding the lipUMs polypeptide used for cloning into *P. pastoris* included the following sequence:

(SEQ ID NO: 13)
ATGCGCTTCATCGCTGTGCGTGCTATTGTCACTTTGGCGGCGGCGGCGGC

GGTGTCATTGGCAGTCCCTACGGAACGTCGTGCGGCTTTTGCTGATCCGA

ACGATGACCTGTTCTATACCACTCCTGACAACATCAATACCTACGCAAAT

GGCCAGGTTATTCAATCCAGAAAGGCGGATACTGACATCGGAAACTCAAA

-continued

```
CAAAGTGGAAGCCTTTCAGTTGCAATATCGCACAACGAATACCCAGAAGG
AGGCACAAGCGAACGTTGCTACTGTGTGGATTCCAAATAAGCCGGCCTCT
CCACCGAAAATCTTTTCCTATCAGGTTTACCAAGATTCTACCCAGCTGAA
CTGTGCACCAAGTTATTCTTTCCTGAAAGGTTTGGACAAACCAAATAAGG
CTACCACTATTCTGGAAGCCCCGATTATCATTGGTTGGGCCTTGCAGCAA
GGCTTTTACGTTGTGTCTTCCGATCATGAAGGCCCTCGCTCAAGCTTCAT
TGCAGGCTATGAAGAGGGAATGGCGATCTTGGATGGTATTCGTGCTCTGA
AGAACTACGCCAAATTGCCAACAGACAGTGCTATTGGCTTTTATGGATAC
TCTGGTGGCGCTCATGCAACCGGATGGGCTGCAAACCTGGCAGGTAGCTA
TGCGCCTGAACACAATATCATTGGTGCAGCGTACGGAGGTCTGCCAGCAA
GTGCGCGTGATACCTTTAACTTCTTGAACAAAGGTGCTTTTGCCGGCTTC
GCAATTGCGGGTGTCTCTGGCCTGGCTTTGGCCTATCCGGATGTTGAAAC
TTACATCCAATCCAGACTGAATGCCAAAGGAGAGAAGGTCTTTAAACAGG
TTCGTTCAAGAGGATTCTGCATTGGTCAAGTCGTTCTGACATATCCATTT
GTTGATGCTTACTCCTTGATCAACGACACGAATCTGTTGAACGAAGAGCC
GGTGGCCTCCACATTGAAGTCAGAAACGCTGGTCCAGGCAGAGGCGTCAT
ATACTGTGCCGGTCCCTAAATTTCCGCGTTTCATCTGGCATGCACTGTTG
GATGAAATTGTGCCTTTCCACAGCGCTGCCACATATGTCAAGGAGCAATG
TAGTAAGGGTGCGGACATTAACTGGAATGTCTACTCATTTGCAGAACACA
TCAGCGCGGAGCTGTTCGGCCTGTTGCCTGGACTGGATTGGTTGAACAAG
GCTTACAAAGGCCAGGCCCCTAAAGTTCCATGCGGCGGAGGTGCTCAAAG
CGTGATGGGAGCAAGTGGTCCTCCAGCGCAGGATGTGCTGGGTGCTGACT
TGGCCTCTCAACTGCGTAGCCTGCAAGGTAAACCATCCGCATTCGGTAAC
AAGCCATTCGGTAGCATCTCACCAGCGGCCGCCAGCTTTCTAGAACAAA
ACTCATCTCAGAAGAGGATCTGAATAGCGCCGTCGACCATCATCATCATC
ATCATTGA.
```

Oligonucleotides were obtained from Biomers.net (Ulm, Germany). As described above, the probes and primers of the present embodiments may be of any length, and are about 60% to about 99% similar to the primers in SEQ ID NO:8 and SEQ ID NO:9, about 75% to about 95% similar to the primers in SEQ ID NO:8 and SEQ ID NO:9, or about 80% to about 90% similar to the primers in SEQ ID NO:8 and SEQ ID NO:9. By assigning numeric values to a sequence, for example, the first residue is 1, the second residue is 2, etc., an algorithm defining all primers can be proposed:

$$n \text{ to } n+y \quad (1)$$

where n is an integer from 1 to the last number of the sequence and y is the length of the primer minus one, where n+y does not exceed the last number of the sequence. Thus, for a 25-mer, the probes correspond to bases 1 to 25, 2 to 26, 3 to 27 . . . and so on. For a 45-mer, the probes correspond to bases 1 to 45, 2 to 46, 3 to 47 . . . and so on. For a 60-mer, the probes correspond to bases 1 to 60, 2 to 61, 3 to 62 . . . and so on.

In certain embodiments, it will be advantageous to employ nucleic acid sequences of the present embodiments in combination with an appropriate detectable marker (i.e., a "label,") for determining hybridization. A wide variety of appropriate indicator compounds and compositions are known in the art, including, without limitation, fluorescent, radioactive, enzymatic or other ligands, such as avidin/biotin, etc., which are capable of being detected. In particular embodiments, it may be desirable to use a fluorescent label or an enzyme tag such as urease, alkaline phosphatase or peroxidase, instead of radioactive or other environmentally less-desirable reagents. In the case of enzyme tags, colorimetric, chromogenic, or fluorogenic indicator substrates are known that can be employed to provide a method for detecting the sample that is visible to the human eye, or by analytical methods such as scintigraphy, fluorometry, spectrophotometry, and the like, to identify specific hybridization with samples containing one or more complementary or substantially complementary nucleic acid sequences. Constructs and lipase variants were then sequenced.

Expression of lipUMf, lipUMs and Variants Thereof

Figure 2:
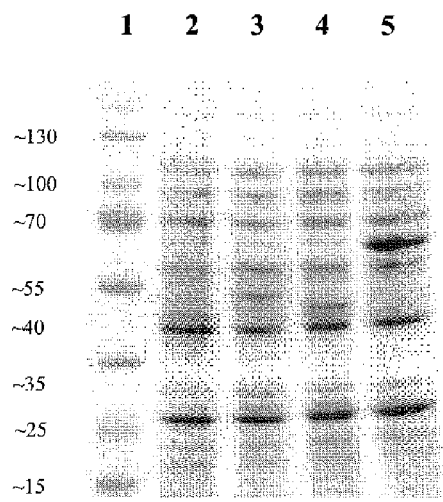
FIG. 2 shows the expression of lipUMs (lane 3), lipase A from *Pseudozyma* (formerly *Candida*) *antarctica* (CAL-A) (lane 4) and lipUMf (lane 5) in crude extracts of transformed *E. coli* C 43 (DE3) strain cells. The gel as shown compares these lanes to *E. coli* cells transformed with an empty pET-22b(+) expression vector as a negative control (lane 2) and a standard marker (lane 1)

E. coli BL21(DE3) (Studier and Moffatt, 1986), C41(DE3) or C43(DE3) (Miroux and Walker, 1996) cells were transformed with pET-22b(+) or derivatives thereof, i.e., pET-22b vectors containing the codon-optimized lipUMf, lipUMs or CAL-A sequences, or variants thereof, using standard procedures known to one of ordinary skill in the art (see e.g., Hanahan, 1983). Complex media used during cultivation of the cells included LB-medium (1% NaCl, 0.5% yeast extract and 1% tryptone), YEPD-medium (1% yeast extract, 2% peptone, 2% glucose), or YEPG-medium (1% yeast extract, 2% peptone, 1% glycerol). Depending on the experimental set-up, E. coli cells were grown in 20, 200, or 400 mL complex media (LB, YEPD or YEPG medium) containing ampicillin (final concentration 100 µg/mL) up to an optical density, $OD_{600}$, of 1.0 at 180 rpm and 37° C. (measurements performed on Fuostar Optima, BMG Labteach GmbH, Offenburg, Germany). For protein expression, isopropylthiogalactoside (IPTG) was added at a final concentration of 0.5 mM. E. coli cells were grown for an additional 22 hours at 180 rpm and 20° C. or 30° C. depending on the experiment. FIG. 2 illustrates that when lipUMf was expressed in E. coli (DE3) strains, strong inclusion body formation was observed in the insoluble fraction of the crude cell extract. This indicates that lipUMf was in fact expressed in E. coli.

Figure 3:
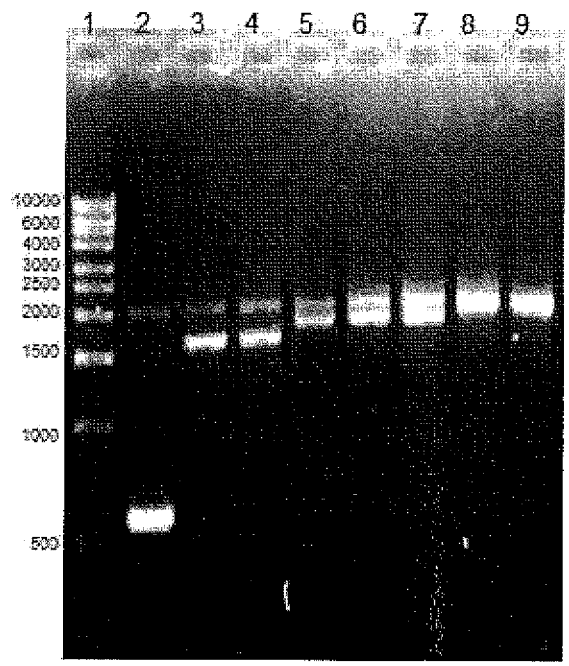
FIG. 3 shows the integration of lipUMs (lanes 3 and 4), lipUMf (lanes 8 and 9) and CAL-A (lanes 5-7) into the genome of *Pichia pastoris*. These lanes can be compared to a standard 1-Kb marker (lane 1) and the PCR product from the empty pPICZα(C) vector. The upper PCR product is the AOX1 gene, while the band below shows the specific PCR-product of the integrated product.

Cultivation temperature was set to about 20° C. during induction to avoid misfolding of the recombinant proteins and to reduce formation of insoluble protein aggregates. FIG. 3 illustrates the hydrolytic activity of crude extracts from two E. coli strains, C41(DE3) and C43(DE3) expressing lipUMs or CAL-A. The activity was measured photometrically with p-NP laurate ($C_{12}$) as a substrate. There is about a one-fold increase when lipUMs is expressed in C41 cells, vs. C43 cells.

P. pastoris X-33 cells (Invitrogen®, Carlsbad, Calif., USA) were transformed with the following vectors: empty pPICZ (B), pPICZ(B) that contained the CAL-A sequence, pPICZ (B) that contained the lipUMf sequence and pPICZ(B) that contained the lipUMs sequence, using standard procedures known to one of ordinary skill in the art (see, e.g., EasySelect™ Pichia Expression Kit, Invitrogen®, Carlsbad, Calif., USA). Successful integration of the lines were confirmed by PCR as described in the EasySelect™ manual, and batch cultivations were performed as described for the secreted Mut⁺ type of P. pastoris integrants. The lines of transformed cells were then grown in both buffered glycerol complex medium (BMGY) and buffered methanol complex medium (BMMY) supplemented with Zeocin™ (copper-chelated *Streptomyces* CL990 glycopeptide antibiotic; InvivoGen, Corp., San Diego, Calif., USA). BMGY was used for pre-culturing of cells and BMMY was used in the main culture. 0.5% MeOH was added every 24 hours. After 4-5 days of growth, the *P. pastoris* cells were harvested. FIG. 3 shows the PCR analysis of the integration of CAL-A, lipUMs and lipUMf sequences into the genome of *P. pastoris* X-33. Both CAL-A and lipUMs integrated into the genome of *P. pastoris* while lipUMf did not, suggesting that the N-terminal domain of lipUMf that was removed from lipUMf to produce the lipUMs, interacts with a target sequence and may therefore be part of a regulatory subunit.

Cell Harvesting and Disruption

For harvesting, transformed *E. coli* cells were centrifuged at 4,500×g for 20 min at 4° C. Cells were washed once with 50 mM sodium phosphate buffer that was kept on ice at pH 7.5. For disruption of cells cultured in a volume 200 mL, a French pressure cell (Thermo Scientific®, Waltham, Mass., USA) was used. Cell pellets were resuspended in 30 mL of 50 mM sodium phosphate buffer that was kept on ice at a pH 7.5 containing 60 μL DNAseI (10 mg/mL). The cell slurry was passed through the French pressure cell twice at 10.324 MPa. Insoluble cell debris was removed by centrifugation at 11,000×g for 30 min at 4° C. The supernatant contained the soluble protein fraction. For cell disruption of smaller culture volumes WOO mL) a sonicator (BransonUltrasonics Corp, Danbury, Conn., USA) was used. For this, the cell pellet was resuspended in 50 mM sodium phosphate buffer that was kept on ice in a volume 1/10 of the original cell culture. The suspension was sonicated at 0° C. and interval pulsed at alternating cycles (Bransonsonicator: 30% power and 50% pulse). Sonication was continued up to 20 min depending on the culture volume. Insoluble cell debris was removed by centrifugation at 11,000×g for 30 min at 4° C. The supernatant contained the soluble protein fraction.

Harvesting of transformed *P. pastoris* cells was performed using standard protocols as provided in the EasySelect™ *Pichia* Expression Kit. Cells were harvested by centrifugation at 1,5000-3,000×g for 30 min at 4° C. The supernatant was then either stored at 4° C. or concentrated further by centrifuge concentrators for small volumes (Amicon® Ultra 30, Millipore Corp., Billerica, Mass., USA) and then stored at 4° C. For SDS-PAGE analysis, the supernatant was concentrated by trichloroacetic acid (TCA) precipitation. The proteins of the supernatant were precipitated by adding 10% TCA for 12 hours at 4° C. The precipitated proteins were washed successively in 100% and 80% acetone and dried at room temperature.

Table 3 shows the results of a fractionation experiment wherein LipUMs and LipUMf were expressed in *P. pastoris* X-33 in the presence of different substrates, i.e., p-NP-$C_{16}$, p-NP-$C_{14}$, p-NP-C18:1Δ9cis, p-NP-C18-1Δ9trans and p-NP-C18:1Δ11cis. pPICZB and pPICZalphaB indicates *P. pastoris* cells transformed with empty vectors, and served as controls. As can be seen from the data in Table 3, lipUMf was not expressed in and/or secreted from *P. pastoris*, or, if present, did not act on the substrates present, however lipUMs polypeptide was present, and active, to varying degrees in the supernatant and whole-cell extract.

TABLE 3

FRACTIONATION RESULTS FOR EXEMPLARY LIPUMS AND LIPUMF

| | pPICZB | | | lipUMs | | | lipUMf | | | pPICZ-alphaB | | |
|---|---|---|---|---|---|---|---|---|---|---|---|---|
| | S | CE | UF | S | CE | UF | S | CE | UF | S | CE | UF |
| pNP-C16 | − | − | − | ++ | + | − | − | − | − | − | − | − |
| pNP-C14 | − | − | − | ++ | + | − | − | − | − | − | − | − |
| pNP-C18:1 Δ9 cis | − | − | − | ++ | + | − | − | − | − | − | − | − |
| pNP-C18:1 Δ9 trans | − | − | − | ++ | + | − | − | − | − | − | − | − |
| pNP-C18:1 Δ11 cis | − | − | − | ++ | + | − | − | − | − | − | − | − |

− = no activity,
+ = activity,
++ = high activity,
S: supernatant,
CE: whole cell-extract,
UF: unsoluble fraction.

Protein Determination by BCA-Assay

To quantitate the protein content of the crude cell extracts, soluble and insoluble fractions, or the purified enzyme itself, the BCA-assay system was used. The BCA-Assay kit from Uptima (Montlucon, France), was used according to the manufacturer's instructions.

SDS-PAGE

For the separation of proteins, discontinuous polyacrylamide gel electrophoresis (PAGE) was used (Laemmli, 1970) under denaturating conditions in the presence of SDS. For this 4% stacking gels combined with 10% or 12% stacking gels were used. For electrophoresis, the "Mini Protean® 3" gel apparatus system from Bio-Rad (München, Germany) was applied at 160V. Before electrophoresis, the protein samples were mixed with SDS, and sample buffer and then denatured for 5 min at 98° C. After electrophoresis, the separated proteins were either blotted on a polyvinylidene fluoride (PVDF) membrane (Carl Roth GmbH+Co. KG, Karlsruhe, Germany) or stained with Coomassie™ reagent. The gel was stained for at least 1 hour in staining solution and then destained with destaining solution until clear blue protein bands became visible. For visualization of separated protein bands, the SDS gel was stained for at least 3 hours in a solution containing Coomassie™ Brilliant Blue G-250, and then destained until clear, and blue protein bands became visible in the gel. To determine hydrolysis activity of the SDS-gel-separated lipases, the gel was blotted on a PVDF membrane and immersed in 100 mL renaturation solution for 1 hour. Then the gel was incubated for 2 to 20 min in a mixture of equal amounts of solution A [0.04% (wt./vol.) 1-naphthyl acetate, 10% (vol./vol.) acetone in sodium phosphate buffer (50 mM, pH 7.0)] and solution B [0.1% (wt./vol.) Sigma-Fast® (Fast Red; 4-chloro-2-methylbenzenediazonium/3-hydroxy-2-naphthoic acid 2,4-dimethylanilide phosphate; Sigma, Steinheim, Germany) in sodium phosphate buffer (50 mM, pH 7.0)]. Development of an insoluble red color indicated hydrolase activity of the enzyme (Higerd and Spizizen, 1973).

Western Blot

For specific determination of protein bands in an SDS gel by antibodies or antibody conjugates, the Western Blot method is used. For blotting the proteins onto a PVDF membrane, the "semi-dry" method was applied using the HEP-3 Panther™ system (Owl SemiDry Electroblotting System; Thermo Scientific, Portsmouth, N.H., USA) according to the manufacturer's instructions. The blotting was done at 15 volts with 0.8 mA/cm² PVDF membrane for 1.5 hours. For blocking of unspecific binding sites in proteins, the membrane was incubated in skim milk solution or 5% bovine serum albumin (BSA) solution for 1 hour at room temperature. After washing the membrane 3 times for 10 minutes each with TBS-Tween buffer, the membrane was incubated for 1 hour in 1/1000 diluted Ni-NTA-conjugate solution. To remove unbound conjugate, the membrane was washed again three times in TBS-Tween® (polysorbate 20) buffer. For detection of specific protein bands, the PVDF membrane was incubated with 33 μL of 5-bromo-4-chloro-3-indolyl phosphate (BCIP) solution and 66 μL of nitro-blue tetrazolium chloride (NBT) solution in 10 mL detection buffer for 2 to 5 minutes. The color reaction was stopped by addition of 3% TCA.

Purification of LipUMf, LipUMs and CAL-A Using Immobilized Metal Affinity Chromatography The presence of the C-terminal His-tag enabled an one-step purification procedure of lipUMf, lipUMs, variants thereof or CAL-A by immobilized metal affinity chromatography (IMAC) with the ÄKTApurifier® (GE Healthcare, Piscataway, N.J., USA). The soluble protein fraction was applied to a chelating Sepharose column (Ni-Sepharose™ 6 Fast Flow; GE Healthcare) preloaded with $Ni^{2+}$ (HisTrap™ FF crude, 5 mL, GE Healthcare, Uppsala, Sweden), equilibrated with 50 mM sodium phosphate buffer containing 300 mM NaCl and 30 mM imidazole, (pH 7.0). The column was washed with equilibrating buffer at a flow rate of 3 to 5 mL/min in order to remove the unbound material. The bound protein was eluted with equilibrating buffer supplemented with 300 mM imidazole. Fractions were collected, concentrated and buffer was exchanged for 50 mM sodium phosphate buffer (pH 7.0) with a polydextran desalting column (Sephadex™ G25, exclusion size 10-kDa; Pharmacia, Uppsala, Sweden) to remove the imidazole. The homogeneity of the purified protein was determined by SDS-PAGE as described above. For identification of certain proteins in specific bands, Matrix-Assisted Laser Desorption/Ionization/Time-of-Flight (MALDI-TOF) mass spectrometry with an Ultraflex® MALDI TOF/TOF instrument (Bruker Daltonics GmbH, Bremen, Germany), and electrospray ionization mass spectrometry was performed with a quadrupole-TOF (Q-ToF) instrument (Micromass, Ltd., Manchester, UK).

Protein Analysis and Enzyme Activity Determination

The functional expression of lipUMf and lipUMs polypeptides was followed by measuring hydrolytic activity according to a slightly modified protocol from Winkler and Stuckmann (1979), by measuring the initial hydrolysis rate of p-NP esters in a 96-well microtiter plate (MTP) format using a Varioskan® FLASH instrument (spectral scanning multi-plate reader, Thermo Scientific, Portsmouth, N.H., USA) at $\lambda=410$ nm ($\epsilon=11.9\times10^3$ $M^{-1}$ $cm^{-}$). The assay solution contained the p-NP ester concentration (1 mM) in sodium phosphate buffer (50 mM, pH 7.0). The reaction was initiated by addition of 30 μL enzyme solution to a 270-μL assay solution; absorbance was then followed for 5 min. One unit of lipase activity was defined as the amount of enzyme releasing 1 μmol. p-NP per minute. All measurements were performed in triplicate. Protein concentration was determined by the bicinchoninic acid (BCA) assay (Uptima, Montlucon, France) with bovine serum albumin as the standard. Expression of the recombinant lipases was also verified by Western blot analysis using a Ni-NTA® conjugate (Qiagen, Corp., Hilden, Germany). Samples were separated by SDS-PAGE according to the method of Laemmli (1970). Protein samples were loaded on a 10.0% SDS-gel together with a prestained molecular weight marker (Thermo-Scientific/Fermentas AB, Vilnius, Lithuania). A mini-SDS-PAGE system (Mini-Protean®II, Bio-Rad, Corp., Munich, Germany) was used for electrophoresis. After SDS-PAGE, the proteins were blotted onto PVDF membranes (Carl Roth GmbH) by the semi-dry method (HEP-3 Panther™ System, Thermo Scientific). After blocking and washing the membrane, the Ni-NTA™ conjugate was used to detect the C-terminal 6×His-tag. The complex was visualized by enzymatic color formation upon the addition of the BCIP/NBT substrate (Sigma-Aldrich).

Figure 4:
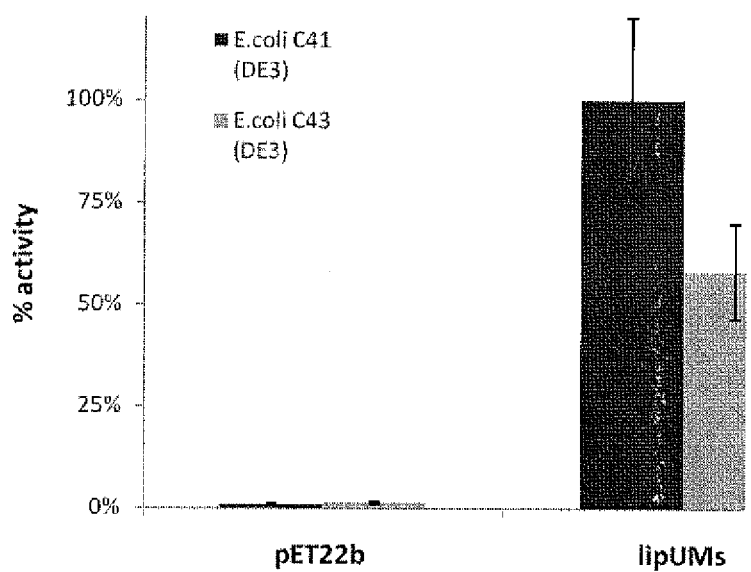
FIG. 4 shows a comparison of the hydrolytic activity of crude extracts from two *E. coli* strains, C41 (DE3) and C43 (DE3), each expressing lipUMs. The activity was measured photometrically with para-nitrophenyl (p-NP) laureate ($C_{12}$ fatty acid esterified with p-nitrophenol) as the substrate. The percent activity is shown as compared to *E. coli* cells transformed with an empty pET-22b(+) expression vector as a negative control.

FIG. 4 is a graph that compares the relative hydrolytic activity of E. coli C41 and C43 cells. LipUMs has higher hydrolytic activities when expressed in C41 cells than in C43 cells.

Figure 5:
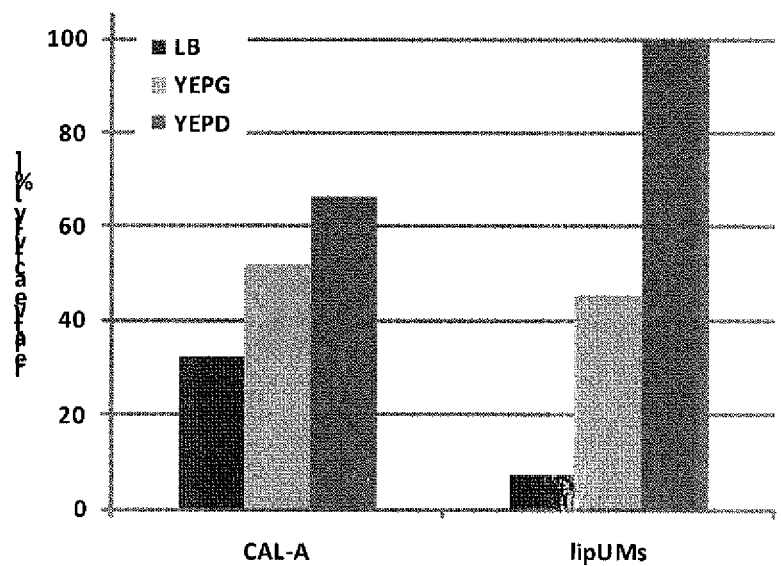
FIG. 5 shows a comparison of the hydrolytic activity of C41 *E. coli* crude extracts cultured on three different cultivation media, namely standard complex medium (LB), glycerol enriched complex medium (YEPG) and glucose enriched complex medium (YEPD), at 20° C. and 180 rpm. The photometric assay was performed with p-NP myristate ($C_{14}$) as the substrate.

FIG. 5 is a graph that compares the hydrolytic activities of E. coli C41 cells on three different cultivation media, standard Luria broth medium (LB), glycerol enriched cultivation medium (YEPG), and glucose enriched complex medium (YEPD), at 20° C. and 180 rpm. The photometric assay was performed with p-NP laureate ($C_{12}$) as a substrate. The hydrolytic activity of crude extracts of CAL-A was increased by about two-fold by cultivation on glucose-enriched medium, the activity of lipUMs increased up to fourteen times when used in glucose enriched medium. LipUMs demonstrates increased activity as compared to CAL-A when the transformed C41 cells were placed on YEPD medium.

Figure 6:
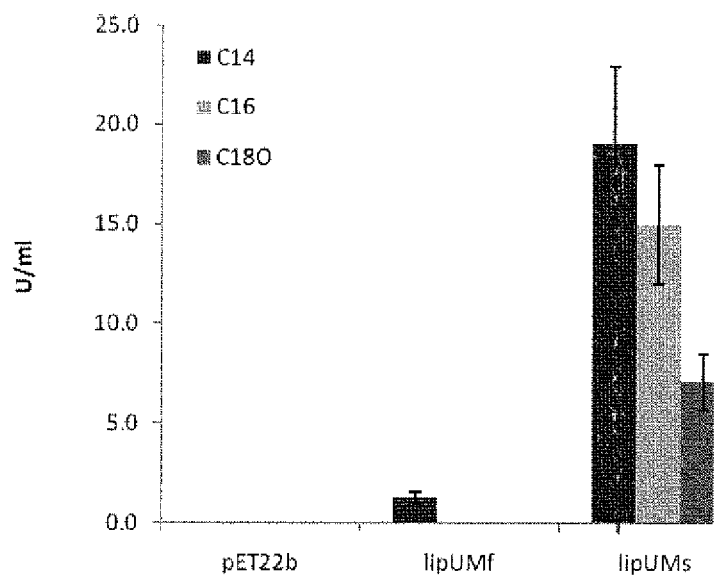
FIG. 6 shows the volumetric lipase activity of *E. coli* C41 (DE3) crude extracts of lipUMs (ums96), and lipUMf (UMf) at 30° C. for three different p-NP-esters, p-NP-C14 ($C_{14}$), p-NP-C16 ($C_{16}$) and p-NP-C18:1Δ9cis ($C_{18O}$)

FIG. 6 shows that when the soluble fraction was analyzed, significant activity was detected with the p-NP-$C_{14}$ substrate for lipUMs, as well as the p-NP-$C_{16}$ and p-NP-$C_{iso}$ substrates. This graph also indicates that a lipUMf polypeptide was functionally expressed in E. coli (DE3) strains however; its activity was only 5% for the p-NP-$C_{14}$ substrate as compared to that of lipUMs expressed under the same conditions. Comparatively, in P. pastoris, only lipUMs polypeptide could be detected as a secreted protein, but not lipUMf polypeptide.

Figure 7:
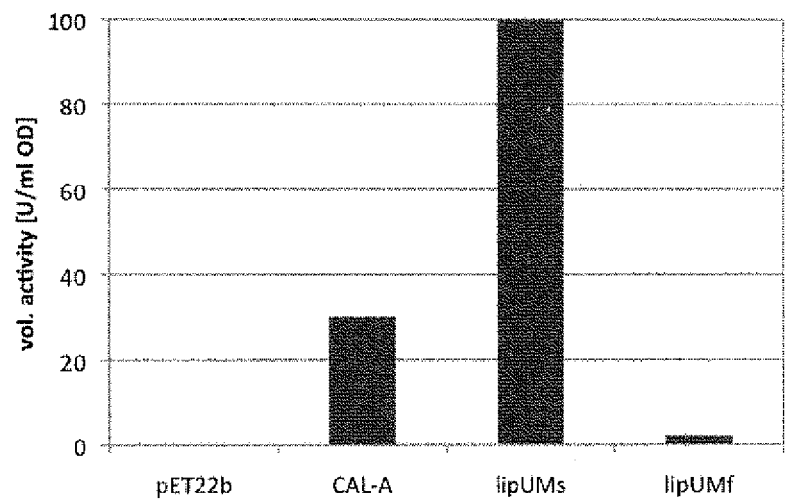
FIG. 7 shows the volumetric lipase activity of *E. coli* crude extracts expressing lipUMs and lipUMf with p-NP myristate ($C_{14}$ fatty acid esterified with p-nitrophenol) ester as a substrate at 45° C. The volumetric lipase activity of lipUMs was about three times higher than for CAL-A. The volumetric activity is shown as compared to *E. coli* cells transformed with an empty pET-22b(+) expression vector as a negative control.

FIG. 7 shows the results of optimized photometric assay conditions for the expression of lipUMs. p-NP myristate ($C_{14}$) was used as a substrate at a temperature of 45° C. This temperature is near-optimal for expression of lipUM and lipUMs. E. coli C41 (DE3) cells were transformed with nucleic acid segments encoding either lipUMf or lipUMs, and then cultured in a 20-mL volume at 20° C. and 200 rpm. Again, lipUMf polypeptide was expressed at only 5% of that of lipUMs polypeptide under these conditions. LipUms polypeptide demonstrated marked increased activity compared to both CAL-A- and lipUMf-transformed cells.

Table 4 shows a summary of the purification results of the lipase lipUMs and CAL-A. The lipases were expressed in the E. coli C41 (DE3) strain at 20° C. and 180 rpm. Purification was performed by His-tag chromatography followed by gel filtration. p-NP myristate ($C_{14}$) was used as a substrate.

TABLE 4

PURIFICATION RESULTS OF THE LIPASES CAL-A AND LIPUMS

| Lipase | Purification step | Total protein [$mg_{protein}$/ml] | Spec. activity [$U/mg_{protein}$] | Yield [%] | Purification factor |
|---|---|---|---|---|---|
| CAL-A | Crude extract | 145 | 0.27 | 100 | 1 |
|  | His$_6$-tag | 4.9 | 29 | 52 | 109 |
|  | His$_6$-tag | 9 | 0.29 | 1.6 | 10 |
| lipUMs | Crude extract | 28 | 1.1 | 100 | 1 |
|  | His$_6$-tag | 0.26 | 40 | 4.5 | 36 |

High specific activities of 40 U/mg were found for lipUMs, which exceeded the value of 29 U/mg for CAL-A, demonstrating the preference of lipUMs for long chain ($C_{12}$ or greater) length fatty acids using this purification procedure.

Figure 8:
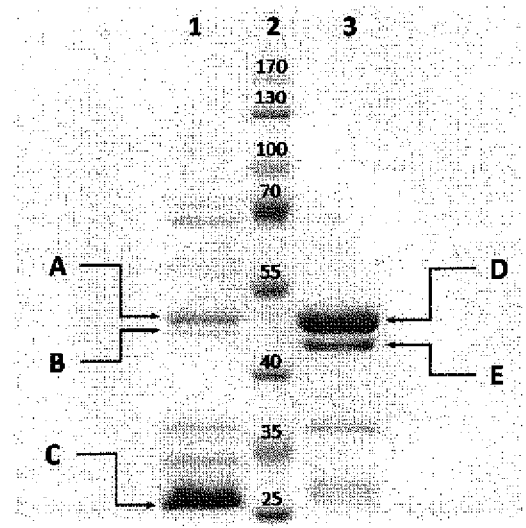
FIG. 8 shows the detection of processed and degraded lipUMs form variants (lane 3), as well as CAL-A (lane 1) by a Coomassie™ Brilliant Blue G-250-stained (AkzoNobel, London, England, UK) 10% sodium dodecyl sulphate-polyacrylamide gel electrophoresis (SDS-PAGE) gel. The CAL-A and lipUMs fractions were purified by His-tag purification. A pre-stained protein ruler marker is shown for comparison (lane 2). The identity of the protein bands was analyzed by MALDI-ToF. Band A represent the unprocessed form of lipUMs (~49 kDa), band B represents the processed form of lipUMs without the pre-pro leader sequence (~47 kDa), band C represents the degraded and/or cleavage product of the lipUMs (~28 kDa), band D represents the unprocessed form of CAL-A (~49 kDa) and band E represents the processed form of CAL-A without the pre-pro leader sequence (~46 kDa).

FIG. 8 shows a Coomassie™ reagent-stained 10% SDS-PAGE gel, which identifies different forms of CAL-A and lipUMs. These fractions were purified by His-tag purification. MALDI-TOF analysis further confirmed that the purified protein product in this experiment was that of lipUMs.

Example 3

Mutagenesis

Sequencing

DNA and protein sequencing can be performed by any method known to one of ordinary skill in the art. DNA sequencing was performed by GATC Biotech AG (Konstanz, Germany). For example, DNA sequencing of the LipUMs point mutants within their respective plasmids, resulting from site-directed mutagenesis, was performed according to the single read sequencing method (GATC Biotech AG).

Site-Directed Mutagenesis

Site-directed mutagenesis was used to generate substitutions at targeted codons of the gene of interest. Therefore, a modified site-directed mutagenesis protocol was applied, which was based on a commercial site-directed mutagenesis kit (QuikChange®, Stratagene, Corp., La Jolla, Calif., USA). To introduce specific amino acid substitutions in the amino acid sequence of the gene of interest, mutagenic primers (between 22 and 30 bases in length) were designed to contain the desired DNA codon that would result in the targeted amino acid substitution. For optimal primer design, the PrimerX™ program (Lapid and Gao, BioInformatics.org, 2003) was used as available online The most-suitable primer pair suggestion was identified, and modified manually according to published methods (Zheng et al., 2004). In particular aspects, the pair of amplification primers includes a first and second oligonucleotide primer of less than about 50, less than about 40, and less than about 30 nucleotides each in length that includes the nucleic acid sequence as identified by the above-noted process. Table 5 shows illustrative primers used to create particularly desirable point mutations in the lipUMs mutant polypeptides:

The 50-µL reaction mixture contained each 2.5 ng/µL of upstream and downstream primers, 1 ng/µL of template plasmid, 200 µM of dNTP-Mix (Carl Roth GmbH), and 0.05 U PfuTurbo® DNA polymerase (Roboklon, Berlin, Germany). The recommended PCR buffer for the polymerase was used, and PCR was performed using the Touchgene™ Gradient TPersonal PCR-machine (Techne®, Cambridge, UK). The following PCR program was used: 1× (1 min 95° C.), 18× (1 min 95° C., 1 min at melting temperature ($T_m$) of primer with the lowest melting temperature, 12 min at 72° C.). The DNA was digested with the restriction enzyme DpnI (Fermentas AB) to degrade non-mutagenized parental DNA. The PCR products were transformed into chemo-competent *E. coli* cells (NEB 5-α F' I$^q$®, New England Biolabs, Frankfurt, Germany). The DpnI digestion was performed according to manufacturer's protocols. The transformation was done by the heat shock method (T=42° C. at 45 sec) as described by Hanahan (1983). Mutants were confirmed by nucleotide sequencing. This procedure was used for the expression of both lipUMs, variants thereof, and CAL-A in both *E. coli* and *P. pastoris* cells.

Example 4

The Characterization of Lipase LipUMs

Fatty acid or carboxylic acid moiety chain length profiles of lipUMs and CAL-A were determined. p-NP esters of different chain lengths ($C_2$ to $C_{18}$) were used. The temperature and pH optimums for lipUMs were determined as well as quantification of trans-preference.

Synthesis of p-NP oleate and p-NP elaidate

To a 250-mL round-bottom flask, with magnetic stirring, under an inert atmosphere ($N_2$), the following was added: anhydrous zinc chloride ($ZnCl_2$) (1.5 g, 11.0 mmol), anhydrous dichloromethane (75 mL) and p-NP (2.8 g, 20.1 mmol). Oleic acid chloride (2.8 g, 8.83 mmol) was added dropwise by a syringe, and the reaction mixture was refluxed until complete conversion was observed by thin-layer chromatography (TLC) (~1 hour). The reaction mixture was then cooled to

TABLE 5

| Primers | Point Mutation |
|---|---|
| 5'-GCTCAAGCGACATTGCAGGCTAT-3' (SEQ ID NO: 14)<br>5'-GGGAGCGAGTTCGCTGTAACGTC-3' (SEQ ID NO: 15) | F145D |
| 5'-CAGCAAGTAACCGTGATACCTTTAA-3' (SEQ ID NO: 16)<br>5'-AGACGGTCGTTCATTGGCACTATG-3 ' (SEQ ID NO: 17) | A214N |
| 5'-GCGTGATCATTTTAACTTCTTGAA-3' (SEQ ID NO: 18)<br>5'-GTTCACGCGCACTAGTAAAATTGAAG-3' (SEQ ID NO: 19) | T217H |
| 5'-GATACCTCGAACTTCTTGAACAA-3' (SEQ ID NO: 20)<br>5'-CGCGCACTATGGAGCTTGAAG-3' (SEQ ID NO: 21) | F218S |
| 5'-GAGCCGCACGCCTCCACATTGA-3' (SEQ ID NO: 22)<br>5'-CTTGCTTCTCGGCGTGCGGAGGTG-3' (SEQ ID NO: 23) | V297H |
| 5'-CTCCACAAACAAGTCAGAAACGCT-3' (SEQ ID NO: 24)<br>5'-GCCACCGGAGGTGTTTGTTCAGTC-3' (SEQ ID NO: 25) | L301N |
| 5'-ATTGCGGCTGTCTCTGGCCTGG-3' (SEQ ID NO: 26)<br>5'-GAAGCGTTAACGCCGACAGAGA-3' (SEQ ID NO: 27) | G233A |
| 5'-CAATTGCGTATGTCTCTGGCCTGGCTT-3' (SEQ ID NO: 28)<br>5'-GGCCGAAGCGTTAACGCATACAGAGAC-3' (SEQ ID NO: 29) | G233Y |
| 5'-ATTGCGCTTGTCTCTGGCCTGG-3' (SEQ ID NO: 30)<br>5'-CGAAGCGTTAACGCGAACAGAGA-3' (SEQ ID NO: 31) | G233L | room temperature, 75 mL water was added, and the organic layer separated. The aqueous phase was extracted with diethyl ether ($Et_2O$) (2×75 mL). The combined organic layers were further washed with sodium bicarbonate ($NaHCO_3$) (2×75 mL). The organic layer was then dried with anhydrous sodium sulfate ($Na_2SO_4$), filtered and reduced in vacuo to give a dark-brown oil. Purification was performed by flash chromatography (10:1 hexane:$Et_2O$) to afford the pure p-NP oleate (2.228 g, 5.51 mmol, 62%) as a clear, colorless oil. $^1$H-NMR (300 MHz; dilute solution in $CDCl_3$) δ=8.27 (2H, d, J=9.25 Hz, 2×Ar—H), 7.27 (2H, d, J=9.25 Hz, 2×Ar—H), 5.43-5.30 (2H, m, —HC=CH—), 2.60 (2H, t, J=7.55 Hz, α-$CH_2$), 2.11-1.91 (4H, m, $H_2$CHC=CHC$H_2$), 1.83-1.69 (2H, m, β-$CH_2$), 1.49-1.19 (20H, m), 0.88 (t, J=6.61 Hz, $CH_3$). The analogous procedure for elaidic acid chloride led to the p-NP elaidate ester (64%) as a pale-brown solid. $^1$H-NMR (300 MHz; dilute solution in $CDCl_3$) δ=8.27 (2H, d, J=9.30 Hz, 2×Ar—H), 7.27 (2H, d, J=9.30 Hz, 2×Ar—H), 5.40-5.37 (2H, m, —HC=CH—), 2.60 (2H, t, J=7.50 Hz, α-$CH_2$), 2.01-1.91 (4H, m, $H_2$CHC=CHC$H_2$), 1.81-1.70 (2H, m, β-$CH_2$), 1.45-1.21 (20H, m), 0.90 (t, J=6.60 Hz, $CH_3$). All other p-NP esters were obtained commercially from NU-Check Prep, Inc. (Elysian, Minn., USA).

Spectrophotometric Determination of Lipase Activity by p-NP Esters

Hydrolytic activity of culture supernatants or crude extracts were measured according to the method described by Winkler and Stuckmann (1979). The p-NP esters of different fatty acids were dissolved in 10 mL isopropanol and mixed with 90 mL of sodium phosphate buffer (50 mM, pH 7.5), supplemented with gum arabic (100 mg). The final concentration of the substrates was 1 mM. The reaction was initiated by addition of 20 μL enzyme solution to 180 μL of assay solution (solution C), and absorbance was followed for 5 min. In the assay, the initial hydrolysis rate of p-NP esters was determined in a 96-well MTP format at 2 L=410 nm (ε=11.9×$10^3 M^{-1} cm^{-1}$). One unit of lipase activity was defined as the amount of enzyme releasing 1 μmol p-NP per minute. All measurements were performed in triplicate.

pH-Stat Assay

Lipase activities were determined with the triacylglyceride substrate, tributyrin, by automated titration with 10 mM sodium hydroxide (NaOH) of fatty acids released using the pH-stat TitroLine® alpha (Schott A G, Mainz, Germany). Tributyrin (5% vol./vol.) was emulsified in 20 mL distilled water containing 5% (wt./vol.) gum arabic as a stabilizer using a homogenizer for 7 min at maximum speed (Ultraturax, IKA Labortechnik, Staufen, Germany). Twenty milliliters of the substrate emulsion were heated to 45° C., and the pH was adjusted according to the desired value. Liberated fatty acids were titrated automatically with 0.01 M NaOH to maintain a constant pH. After addition of the enzyme solution, the NaOH consumption was recorded at a reaction temperature of 45° C. For determination of the temperature profile, the pH was set to 7.5. One unit of lipase activity was defined as the amount of lipase liberating 1 μmol fatty acids per minute.

Determination of the Cis- or Trans-Fatty Acid Selectivity of Lipases in pH Soy Oil All reaction and work-up procedures were performed using glassware to prevent contamination by fatty acid like plasticizers such as bis(2-ethylhexyl)phthalate (DEHP). All reactions were performed in glass vial with magnetic stirring. Mole calculations were performed assuming average molecular weight of the mixture was equal to triolein (885 g/mol).

The reactions were performed in triplicate, using three separate reaction vessels. The reaction mixture was prepared by weighing partially-hydrogenated soybean (soy) oil (PHSO) [1000 mg; 1.13 mmol of triacylglycerol (TAG) or 3.39 mmol of cleavable esters] into a tube and flushing with nitrogen. The PHSO was then fully melted by immersion in hot water (40° C.). The PHSO was cooled and gum arabic (400 mg) and phosphate buffer (50 mM; pH 7.5; 20 mL) added. The mixture was emulsified by shear-mixing (24,000 rpm) for 2 min. Aliquots of this mixture [4 mL; 200 mg/0.678 mmol of fatty acid (FA) equivalents] were added to each of the three reaction vessels equipped with magnetic stirring. The reaction mixture was heated to 40° C. Enzyme was either added to, or prepared in, phosphate buffer (50 mM, pH 7.5), and added to the reaction mixture. The reaction mixtures were sampled at appropriate times (either as a time-course of samples, or at 20% conversion). Sampling was performed by removing an aliquot (0.5 mL; 25 mg/85 μmol of FA equivalents), and extracting between hydrochloric acid (HCl) (0.5 M; 1.5 mL) and hexane:chloroform ($CHCl_3$):methanol (MeOH) (49:49:2; 2×2 mL) in a glass vial. The combined organics were dried by filtering through $Na_2SO_4$ in a glass pipette and the solvent removed under nitrogen. When the solvent was fully removed, the remaining oil was quickly resuspended in hexane (1 mL), and a few drops removed for analysis by TLC-FID (Iatroscan®). Derivatization for gas chromatography (GC) analysis was performed by adding sodium methoxide (NaOMe) (2 N in MeOH; 50 μL; 100 μmol) and vortex mixing the sample for 1 min. The resulting mixture was filtered through $Na_2SO_4$ in a glass pipette to remove MeOH, residual NaOMe and solid precipitate, and the resulting filtrate analyzed by GC. For samples taken at high conversion, concentration of the resulting solution (low TAG and therefore low FAME concentrations) under nitrogen was required.

TLC-FID

1 μL of extract was applied to each of three chromarods, and developed in 67:3:0.5 toluene:hexane:AcOH to the top of the chromarod. The chromarods were dried under a stream of nitrogen. Scanning was performed (160 mL/min hydrogen, 2 Lmin air, 40-sec scan rate) and recorded on a chart printer. Integration of the peaks was performed by scanning the image into a computer, and manually integrating using ImageJ (NIH software). Appropriate correction factors were applied, and the results of the three scans averaged and standard deviation error calculated.

GC

The official Ce1h-05 method was used, with the exception that the column temperature was reduced from 180° C. to 170° C., as the mobile phase. The FAME CP-select column (Varian, Calif., USA) was used as the stationary phase. Peaks were integrated manually, and the appropriate correction factors (Ce-1h 05) were applied. The triplicate data (including the further triplicate TLC-FID data) of conversion percentage and trans-content of the bound fraction was averaged and standard deviation error calculated. The trans-content of the FAEE fraction was converted to trans-content of the bound fraction as described.

Figure 9:
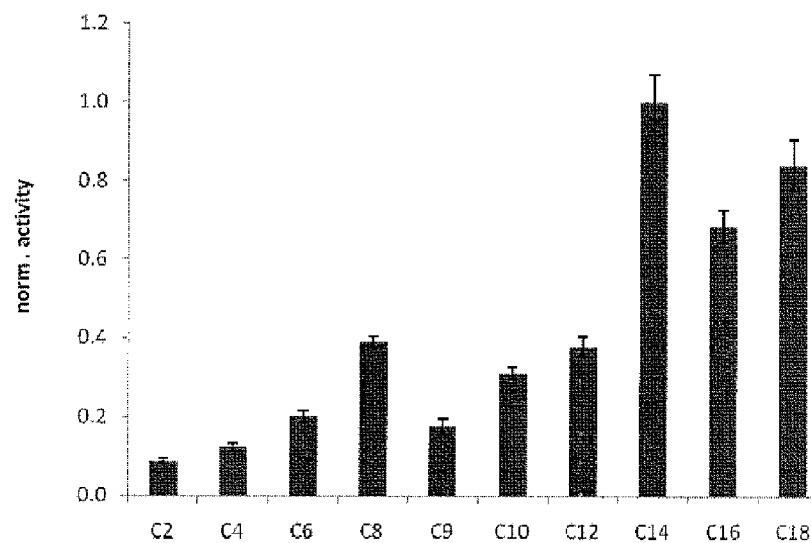
FIG. 9 shows the fatty acid chain length preference of lipUMs. The hydrolytic activity towards p-NP esters with different chain lengths (carbon chain length is indicated by the letter "C" followed by the number of carbons) ($C_2$ through and including $C_{18}$) was normalized to the best hydrolyzed substrate, which was the myristic acid ester ($C_{14}$).

FIG. 9 shows a comparison of chain length preference of lipUMs. LipUMs shows a distinct preference for long chain fatty esters as p-NP myristate ($C_{14}$) was the best substrate.

Figure 10A:
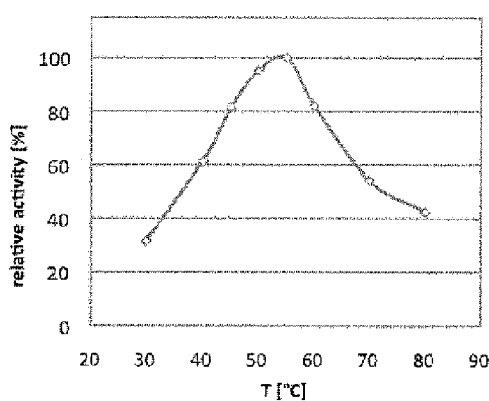
FIG. 10A and FIG. 10B show the temperature and pH optima, respectively, for exemplary lipUMs polypeptides as determined for the substrate tributyrin.
Figure 10B:
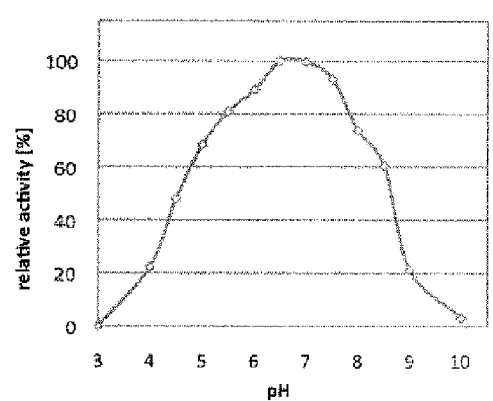

FIG. 10A shows the temperature optimum for lipUMs to be about 55° C. FIG. 10B shows the pH optimum to be between a pH of about 6.5 to about 7.

The fatty acid profiles were determined as described above with p-NP esters of acetate ($C_2$), butyrate ($C_4$), caproate ($C_6$), caprylate ($C_8$), caprate ($C_{10}$), laurate ($C_{12}$), myristate ($C_{14}$), palmitate (C$_{16}$), stearate (C$_{18}$), and linolenate (C18: 3Δ9Δ12Δ15, all cis) obtained from Sigma-Aldrich. The trans-selectivity of the lipases was determined using p-NP elaidate (C18:1Δ9 trans) or p-NP oleate (C18:1Δ9 cis), both chemically synthesized as described above.

Table 6 shows the normalized activity of lipUMs for various p-NP esters of different carbon chain lengths. The hydrolytic activities of lipUMs were normalized to p-NP-C14 (myristic acid ester) and compared to p-NP esters with various carbon chain lengths (C$_2$ through C$_{18}$). Measurements were performed six times, averaged and normalized. The lipUMs lipase variant demonstrates a preference for long chain fatty acids, namely those including more than 12 carbon atoms. It also shows a preference for trans-fatty acids, namely elaidic acid and vaccenic acid, compared to cis-fatty acids, such as oleic acid and linolenic acid.

TABLE 6

COMPARISON OF AVERAGE NORMALIZED ACTIVITY
OF LIPUMS FOR DIFFERENT P-NP ESTERS

| Carbon chain length of p-NP ester | LipUMs |
|---|---|
| C$_2$ | 0.09 |
| C$_4$ | 0.12 |
| C$_6$ | 0.20 |
| C$_8$ | 0.39 |
| C$_9$ | 0.18 |
| C$_{10}$ | 0.31 |
| C$_{12}$ | 0.38 |
| C$_{14}$ | 1.00 |
| C$_{16}$ | 0.69 |
| C$_{18}$ | 0.84 |
| C$_{18O}$ (oleic acid) | 0.54 |
| C$_{18E}$ (elaidic acid) | 0.92 |
| C$_{18V}$ (vaccenic acid) | 1.03 |
| C$_{18L}$ (linolenic acid) | 0.41 |

Figure 11:
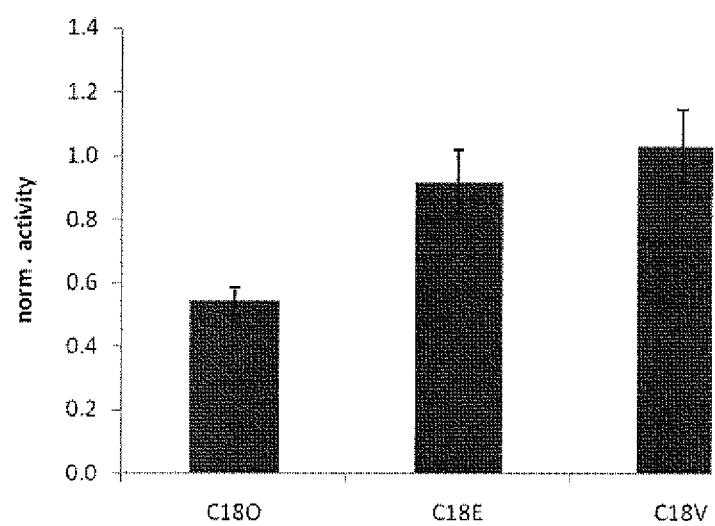
FIG. 11 shows the average initial hydrolysis rates, and therefore, the preference of the exemplary lipUMs polypeptides for three p-NP-esters: p-NP-C18:1Δ9cis (C18O=oleic acid), p-NP-C18:1Δ9trans (C18E=elaidic acid), and p-NP-C18:1 Δ11 trans (C18V=vaccenic acid), respectively. These measurements were done in triplicate.

FIG. 11 demonstrates the preference of lipUMs for p-NP-esters with trans-fatty acids. Three different C$_{18}$ fatty acid chains, i.e., vaccenic acid, elaidic acid and oleic acid, were used as substrates. LipUMs preferentially acted on the trans substrates, i.e., vaccenic acid and elaidic acid, rather than the cis substrate, oleic acid.

Example 5

The Characterization of Lipase UMs Variants

Variants of lipUMs were cloned and functionally expressed in *P. pastoris* cells to evaluate the variants for improved trans-selectivity over lipUMs, as described above.

Hydrolysis and Ethanolysis Assay Using Partially-Hydrogenated Soy Oil (PHSO)

These procedures are as described above.

Determination of α-Factors for Trans Fatty Acid-Selectivity in (PHSO)

Competitive factors (α values) are used to describe the selectivity of an enzyme for different substrates, e.g., selectivity for substrate A vs. substrate B. Fatty acid selectivity was determined as relative competitive factors (α-values), which are proportional to the specificity constants, $V_{max}/K_M$, for each fatty acid as described previously in Chen et al. (1982); Deleuze et al. (1987); Rangheard et al. (1989); and Borgdorf and Warwel (1999). Thus, a greater α-value indicates a greater reaction rate and selectivity for a particular fatty acid substrate. C$_{14}$ was used as the reference fatty acid substrate, because it was usually the fastest-reacting fatty acid, and was assigned an α-value of 1.00.

The enzyme selectivity/specificity is a function of both substrates' binding and catalytic rate and, hence, is determined by the ratio of the specificity constants ($k_{cat}/K_M$). Therefore the competitive factor, α, is defined as the ratio of different specificity constants. For example Rangheard et al. (1989) defined the α-factor for the fatty acid selectivity of an enzyme as fellows:

$$\alpha = \frac{\frac{v_{AC1_X}}{K_{AC1_X}}}{\frac{v_{AC2_X}}{K_{AC2_X}}} = \frac{\log\left(\frac{AC1_X}{AC1_{X_o}}\right)}{\log\left(\frac{AC1_X}{\Box}AC2_{X_o}\right)} \quad \text{(Equation 1)}$$

From Equation 1, it is clear that the competitive factor is equal to the ratio of the reaction rates of two substrates when identical substrate concentrations (AC1$_x$ and AC2$_x$) are used. The definition of the E-value in kinetic resolution is very similar to equation 1

$$E = \frac{\frac{v_A}{K_A}}{\frac{v_b}{K_B}} = \frac{\ln\left[\left(\frac{A}{A_0}\right)\right]}{\ln\left[\left(\frac{B}{B_0}\right)\right]} \quad \text{(Equation 2)}$$

where V$_A$, and V$_B$, denote maximal velocities ($v_{max}$) of the fast- and slow-reacting enantiomers, respectively, and K$_A$ and K$_B$ denote Michaelis constants (K$_M$) of the fast- and slow-reacting enantiomers, respectively. Simpler methods to calculate selectivities may be thought of, such as using the initial slope of the graph or other initial velocity comparisons. However, these methods will not take competition of different substrates in the active site into account and therefore only describe apparent selectivity factors.

For the present embodiments, a modified α-factor method was used that assumed that for the chemical equation, the bound trans-fatty acids (trans$_{bound}$) is in equilibrium with, or in some instances about equal to, the free trans-fatty acids (trans$_{free}$), for the time domain equation, the concentration of the initial trans$_{bound}$ ([trans$_{bound}$]$_0$) over time is in equilibrium with, or in some instances about equal to, the trans$_{bound}$ plus the trans$_{free}$, similarly the initial concentration of the bound non-trans-fatty acids ([non-trans$_{bound}$]$_0$ over time is in equilibrium with, or in some instances about equal to, the non-trans$_{bound}$ plus the non-trans$_{free}$, thus, the initial concentration of the trans-fatty acids is equal to the concentration of bound trans-fatty acids plus the concentration of free trans-fatty acids:

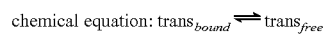
chemical equation: trans$_{bound}$ ⇌ trans$_{free}$

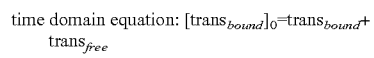
time domain equation: [trans$_{bound}$]$_0$=trans$_{bound}$+ trans$_{free}$

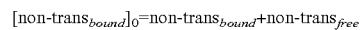
[non-trans$_{bound}$]$_0$=non-trans$_{bound}$+non-trans$_{free}$

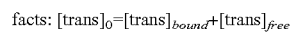
facts: [trans]$_0$=[trans]$_{bound}$+[trans]$_{free}$

Using these premises, Equation 1 can be re-written into Equation 3:

$$\alpha = \frac{\frac{v_{AC1_X}}{K_{AC1_X}}}{\frac{v_{AC2_X}}{K_{AC2_X}}} = \frac{\log\left(\frac{[trans]}{[trans]_0}\right)}{\log\left(\frac{[non\text{-}trans]}{[non\text{-}trans]_0}\right)}. \quad \text{(Equation 3)}$$

The gas chromatography (GC) data provides relative percentages (% trans) rather than concentrations. Thus, the following presumptions were used:
if:

$$[trans]_0 \text{ is relative to } \% \text{ trans}_0 \text{ or } [trans]_0 = X^* \% \text{ trans}_0$$

then:
The % trans from the GC (particularly from GC traces for the bound fraction) correlates into numbers that directly scale with actual concentration. For example, at 30% conversion, there will be a total of 30% free fraction. The percentages for trans and non-trans for the free fraction sums to 100%. For this testing, they must sum to 30%, which is accomplished by multiplying by c (conversion rate):

$$[trans]_{free} \text{ is relative to } \% \text{ trans}_{free}*c \text{ or}$$
$$[trans]_{free} = X^* \% \text{ trans}_{free}*c$$

At 30% conversion, there will be a total of 70% bound fraction. The percentages for trans and non-trans for the bound fraction will sum to 100%. Therefore, it is needed to make them sum to 70%. So multiply by 1-c:

$$[trans]_{bound} \text{ is relative to } \% \text{ trans}_{bound}*1\text{-}c \text{ or}$$
$$[trans]_{bound} = X^* \% \text{ trans}_{bound}*1\text{-}c$$

so:

$$\alpha = \frac{\log([trans]/[trans]_0)}{\log([non\text{-}trans]/[non\text{-}trans]_0)}$$

$$\alpha = \frac{\log(X*(\% \ trans_{bound}*1-c)/X*(\% \ trans_0))}{\log(X*(\% \ non\text{-}trans*1-c)/X*(\% \ non\text{-}trans_0))}$$

The X factors cancel, therefore:

$$\alpha = \frac{(\% \ trans_{bound}*1-c)/\% \ trans_0}{\log(\% \ non\text{-}trans*1-c)/\% \ non\text{-}trans_0} \quad \text{(Equation 4)}$$

The X factors cancel because when a sample is submitted to the GC, a chromatogram that defines X for each fatty acid is provided (whether bound or free, they are now all FAME [fatty acid methyl esters]) in that sample, and only that sample. X will vary depending on the exact concentration of lipid in any given extract. For any given extraction, the percentage distribution of the peaks is identical whether 1 mg or 100 mg are submitted to the GC. Therefore, X can be cancelled.

When the calculated a factor becomes negative, it is indicating very high selectivities for the chosen comparison of substrates, e.g., a (trans+sat)/cis<0. To show this, the selectivity factor α by the method of Chen et al. (1982) is recalculated. While the Chen publication only takes into account values for the two different enantiomers, R and S, the behavior in pH soy is more complex. There multicompetitive reactions for the hydrolysis of different fatty acids take place. In order to simplify this further and make it applicable to the equation of Chen et al. (1982), we distinguish between three fractions: cis fatty acids, trans fatty acids and saturated fatty acids. Instead of using the content of the bound-fraction like in the modified Rangheard equation, the calculated released fatty fraction for calculating a modified eeP value was used (equation 5):

$$eeP=[(\% \ trans+\% \ sat)-\% \ cis]/[(\% \ trans+\% \ sat)+\% \ sat] \quad \text{(Equation 5)}$$

This value (eeP) can now be used to determine a pseudo E-value for the complex fat mixture.

$$E=(v_1A/K_1A)/(v_1B/K_1B)=(\ln[(1-c(1+eeP)])/(\ln[(1-c(1-eeP)]) \quad \text{(Equation 6)}$$

This E-value equation will give positive values, where the rational log function employed by Rangheard et al. (1989) and Borgdorf and Warwel (1999) will give negative values. Therefore, the negative numbers calculated by the modified Rangheard equation could be converted to high positive numbers using the modified equation from Chen et al. (1982) for calculating E-values. In kinetic resolution, E-values >100 indicate excellent selectivites but cannot be calculated precisely. Table 7 summarizes the α-value data for UMs and variants thereof, when expressed in *P. pastoris*.

TABLE 7

α-FACTORS FOR VARIANTS OF LIPUMS AND UMS

| Enzyme | Experiment | Multi-plate | α Trans/(Cis + Sat) | α (Trans + Sat)(Cis) |
|---|---|---|---|---|
| None | Hydrolysis | 1 | No detection | — |
| None | Ethanolysis | 1 | 4 days <1% conv | — |
| Geobacillus | Hydrolysis | 3 | 0.72 ± 0.09 | — |
| LipUMs | Hydrolysis | 3 | 2.04 ± 0.56 | 5.84 ± 0.88 |
| LipUMs | Ethanolysis | 3 | 2.28 ± 0.08 | — |
| L301N variant of LipUMs | Hydrolysis | 3 | 2.11 ± 0.12 | 4.17 ± 0.62 |
| T217H variant of LipUMs | Hydrolysis | 3 | 1.42 ± 0.66 | 2.70 ± 0.88 |
| V297H variant of LipUMs | Hydrolysis | 3 | 1 day <1% conv | — |
| V297H variant of LipUMs | Ethanolysis | 3 | 1 day <1% conv | — |

(—) indicates that the study was not performed

As shown in Table 7, the L301N lipUMs variant had the most-improved trans-selectivity as compared to lipUMs. A lipase from *Geobacillus* was included to show the α-factor for a non-selective lipase, i.e., a lipase that does not preferentially bind either a cis- or a trans-substrate. As compared to the lipase from *Geobacillus*, lipUMs, and all of the lipUMs variants shown indicate an increased trans-selectivity, as per their α-factors. For example, LipUMs, demonstrates about a 183% increase in hydrolytic activity when compared to that of *Geobacillus*. The L301N variant demonstrates about a 193% increase in hydrolytic activity when compared to that of *Geobacillus*. "Multiplate" indicates the number of times the reaction was performed and quantitated.

REFERENCES

The following references, to the extent that they provide exemplary procedural or other details supplementary to those set forth herein, are specifically incorporated herein in their entirety by express reference thereto:

Altschul, S. F., Gish, W., Miller, W., Myers, E. W., and Lipman, D. J. 1990. Basic local alignment search tool. *J Mol Biol* 215: 403-410.

Anthonsen, H. W., Baptista, A., Drablos, F., Martel, P., Petersen, S. B., Sebastiao, M., and Vaz, L. 1995. Lipases and esterases: a review of their sequences, structure and evolution. *Biotechnol. Annu. Rev.* 1: 315-371.

Aparna, G., Chatterjee, A., Sonti, R. V., and Sankaranarayanan, R. 2009. A cell wall-degrading esterase of *Xanthomonas oryzae* requires a unique substrate recognition module for pathogenesis on rice. *Plant Cell* 21: 1860-1873.

Arnold K., Bordoli L., Kopp J., and Schwede T. (2006). The SWISS-MODEL Workspace: A web-based environment for protein structure homology modelling. Bioinformatics, 22, 195-201.

Beer, H. D., McCarthy, J. E., Bornscheuer, U. T., and Schmid, R. D. 1998. Cloning, expression, characterization and role of the leader sequence of a lipase from *Rhizopus oryzae*. *Biochim Biophys Acta* 1399: 173-180.

Beer, H. D., Wohlfahrt, G., Schmid, R. D., and McCarthy, J. E. 1996. The folding and activity of the extracellular lipase of *Rhizopus oryzae* are modulated by a prosequence. *Biochem J* 319 (Pt 2): 351-359.

Bendtsen, J. D., Nielsen, H., von Heijne, G., and Brunak, S. 2004. Improved prediction of signal peptides: SignalP 3.0. *J Mol Biol* 340: 783-795.

Berman, H. M., Westbrook, J. D., Gabanyi, M. J., Tao, W., Shah, R., Kouranov, A., Schwede, T., Arnold, K., Kiefer, F., Bordoli, L., et al. 2009. The protein structure initiative structural genomics knowledgebase. *Nucleic Acids Res* 37: D365-368.

Borgdorf, R., and Warwel, S. 1999. Substrate selectivity of various lipases in the esterification of cis- and trans-9-octadecenoic acid. *Appl Microbiol Biotechnol*, 51: 480-485.

Bornscheuer, U. T., and Kazlauskas, R. J. 2005. Hydrolases in Organic Synthesis—Regio- and Stereoselective Biotransformations, 2nd ed. Wiley-VCH, Weinheim Brunke, S., and Hube, B. 2006. MfLIP1, a gene encoding an extracellular lipase of the lipid-dependent fungus Malassezia furfur. *Microbiology* 152: 547-554.

Chen, C. S., Y. Fujimoto, et al. (1982). Quantitative analyses of biochemical kinetic resolutions of enantiomers. *Journal of the American Chemical Society*, 104(25): 7294-7299.

Deleuze, H., G. Langrand, et al. (1987). Lipase-catalyzed reactions in organic media: competition and applications. *Biochim Biophys Acta*, 911(1): 117-120.

de Maria, P. D., Carboni-Oerlemans, C., Tuin, B., Bargernan, G., van der Meer, A., and van Gernert, R. 2005. Biotechnological applications of *Candida antarctica* lipase A: State-of-the-art. *Journal of Molecular Catalysis B-Enzymatic* 37: 36-46.

Dumon-Seignovert, L., Cariot, G., and Vuillard, L. 2004. The toxicity of recombinant proteins in *Escherichia coli*: a comparison of overexpression in BL21(DE3), C41(DE3), and C43(DE3). *Protein Expr Purif* 37: 203-206.

Emanuelsson, O., Nielsen, H., Brunak, S., and von Heijne, G. 2000. Predicting subcellular localization of proteins based on their N-terminal amino acid sequence. *J Mol Biol* 300: 1005-1016.

Ericsson, D. J., Kasrayan, A., Johanssonl, P., Bergfors, T., Sandstrom, A. G., Backvall, J. E., and Mowbray, S. L. 2008. X-ray structure of *Candida antarctica* lipase a shows A novel lid structure and a likely mode of interfacial activation. *Journal of Molecular Biology* 376: 109-119.

Fiser, A., R. K. Do, et al. (2000). Modeling of loops in protein structures. *Protein Sci* 9(9): 1753-1773.

Hanahan, D. 1983. Studies on transformation of *Escherichia coli* with plasmids. *J Mol Biol* 166: 557-580.

Hegde, R. S., and Bernstein, H. D. 2006. The surprising complexity of signal sequences. *Trends Biochem Sci* 31: 563-571.

Higerd, T. B. and Spizizen, J. 1973. Isolation of two acetyl esterases from extracts of *Bacillus subtilis*. *J Bacteriol* 114: 1184-1192.

Hoegh, I. S. P., T. Halkier, M. T. Hansen. 1995. Two lipases from *Candida antarctica*: Cloning and expression in *Aspergillus oryzae*. *Can J Bot* 73: S869-S875.

Holm, L., and Sander, C. 1993. Protein structure comparison by alignment of distance matrices. *J Mol Biol* 233: 123-138.

Holmquist, M. 2000. Alpha/Beta-hydrolase fold enzymes: structures, functions and mechanisms. *Curr Protein Pept Sci* 1: 209-235.

Indrasena, W. M., Henneberry, K., Barrow, C. J., and Kralovec, J. A. 2005. Qualitative and quantitative analysis of lipid classes in fish oils by thin-layer chromatography with an iatroscan flame ionization detector (TLC-FID) and liquid chromatography with an evaporative light scattering detector (LC-EL SD). *J. Liq. Chromatog.* 28: 2581-2595.

Invitrogen. 1997-2001. EasySelect™ *Pichia* Expression Kit: A Manual of Methods for Expression of Recombinant Proteins Using pPICZ and pPICZα in *Pichia pastoris*. Version G. Catalog No. K1740-01.

Kaitaranta, J. K. and Nicolaides, N. 1981. Response and linearity of different lipid compounds when analyzed by thin-layer chromatography with flame ionization detection. *J. Chromatog.* 205: 339-347.

Kakugawa, K., Shobayashi, M., Suzuki, O., and Miyakawa, T. 2002. Cloning, characterization, and expression of cDNA encoding a lipase from *Kurtzmanomyces* sp. I-11. *Biosci Biotechnol Biochem* 66: 1328-1336. (Kakugawa, et al., 2002[2]).

Kakugawa, K., Shobayashi, M., Suzuki, O., and Miyakawa, T. 2002b. Purification and characterization of a lipase from the glycolipid-producing yeast *Kurtzmanomyces* sp. I-11. *Biosci Biotechnol Biochem* 66: 978-985. (Kakugawa, et al., 2002[1]).

Kasrayan, A., Bocola, M., Sandstrom, A. G., Laven, G., and Backvall, J. E. 2007. Prediction of the *Candida antarctica* lipase A protein structure by comparative modeling and site-directed mutagenesis. *Chembiochem* 8: 1409-1415.

Kemper et al. Insights from the genome of the biotropic fungal plant pathogen *Ustilago maydis*. Nature. 444:97-101.

Kirk, O., and Christensen, M. W. 2002. Lipases from *Candida antarctica*: Unique biocatalysts from a unique origin *Organic Process Research & Development* 6: 446-451.

Kourist, R., Brundiek, H., and Bournscheuer, U. T. 2010. Protein engineering and Discovery of lipases. *Eur. J. Lipid Sci. Technol.* 112: 64-74.

Krishna, S. H., Persson, M., and Bomscheuer, U. T. 2002. Enantioselective transesteri cation of a tertiary alcohol by lipase A from. *Tetrahedron* 13: 2693-2696.

Krogh, A., Larsson, B., von Heijne, G., and Sonnhammer, E. L. 2001. Predicting transmembrane protein topology with a hidden Markov model: application to complete genomes. *J Mol Biol* 305: 567-580.

Laemmli, U. K. 1970. Cleavage of structural proteins during the assembly of the head of bacteriophage T4. *Nature* 227: 680-685.

Li, X. G., and Kanerva, L. T. 2006. Lipases in beta-dipeptide synthesis in organic solvents. *Org Lett* 8: 5593-5596.

Miroux, B., and Walker, J. E. 1996. Over-production of proteins in *Escherichia coli*: mutant hosts that allow synthesis of some membrane proteins and globular proteins at high levels. *J Mol Biol* 260: 289-298.

Napolitano, G. and Giuffrida, F. 2009. Ch. 6-Replacement of Partially Hydrogenated Oils in Food Products: A Technical Challenge, *Trans Fatty Acids in Human Nutrition*, Oily Press Ltd., 2$^{nd}$ ed.

Ollis, D. L., Cheah, E., Cygler, M., Dijkstra, B., Frolow, F., Franken, S. M., Harel, M., Remington, S. J., Silman, I., and Schrag, J. 1992. The α/β hydrolase fold. *Protein Eng.* 5: 197-211.

Powell, M. 1992. Restart procedures for the conjugate gradient method mj. d. *Mathematical Programming* 12: 241-254.

Pfeffer, J., Richter, S., Nieveler, J., Rachid, C.-e. H., Rhlid, B., Schmid, R. D., and Rusnak, M. 2006. High yield expression of Lipase A from *Candida antarctica* in the methylotrophic yeast *Pichia pastoris* and its purification and characterisation. *Applied Microbiology*: 931-938.

Pfeffer, J., Rusnak, M., Hansen, C. E., Rhlid, R. B., Schmid, R. D., and Maurer, S. C. 2007. Functional expression of lipase A from *Candida antarctica* in *Escherichia coli*—A prerequisite for high-throughput screening and directed evolution. *Journal of Molecular Catalysis B-Enzymatic* 45: 62-67.

Rangheard, M. S., G. Langrand, et al. (1989). Multi-competitive enzymatic reactions in organic media: a simple test for the determination of lipase fatty acid specificity. *Biochimica et biophysica acta*, 1004(1): 20-28.

Ratnayake, W. M. N. and Cruz-Hernandez, C., 2009. Ch. 5—Analysis of Trans Fatty Acids of Partially Hydrogenated Vegetable Oils and Dairy Products, *Trans Fatty Acids in Human Nutrition*, Oily Press Ltd., 2$^{nd}$ ed.

Schmidt, M., Barbayianni, E., Fotakopoulou, I., Ho, M., Constantinou-kokotou, V., Bornscheuer, U. T., and Kokotos, G. 2005. Enzymatic Removal of Carboxyl Protecting Groups. 1. Cleavage of the. 3737-3740.

Schwede T, Kopp J, Guex N, and Peitsch M C (2003) SWISS-MODEL: an automated protein homology-modeling server.

Sezonov, G., Joseleau-Petit, D., and D'Ari, R. 2007. *Escherichia coli* physiology in Luria-Bertani broth. *J Bacteriol* 189: 8746-8749.

Studier, F. W. and Moffatt, B. 1986. Use of bacteriophage T7 RNA polymerase to direct selective high-level expression of cloned genes. *J. Mol. Biol.* 189: 113-130.

Takahashi, S., M. Ueda, et al. (2001). Function of the prosequence for in vivo folding and secretion of active *Rhizopus oryzae* lipase in *Saccharomyces cerevisiae*. *Appl Microbiol Biotechnol* 55(4): 454-462.

von Heijne, G. 1985. Signal sequences. The limits of variation. *J Mol Biol* 184: 99-105.

Wagner, S., Klepsch, M. M., Schlegel, S., Appel, A., Draheim, R., Tarry, M., Hogbom, M., van Wijk, K. J., Slotboom, D. J., Persson, J. O., et al. 2008. Tuning *Escherichia coli* for membrane protein overexpression. *Proc Natl Acad Sci USA* 105: 14371-14376.

Warwel, S., and Borgdorf, R. 2000. Substrate selectivity of lipases in the esterification of cis/trans-isomers and positional isomers of conjugated linoleic acid (CLA). *Biotechnology Letters* 22: 1151-1155.

Warwel, S., Borgdorf, R., and Bruhl, L. 1999. Substrate selectivity of lipases in the esterification of oleic acid, linoleic acid, linolenic acid and their all-trans-isomers and in the transesterification of cis/trans-isomers of linoleic acid methyl ester. *Biotechnology Letters* 21: 431-436.

Winkler, U. K., and Stuckmann, M. 1979. Glycogen, hyaluronate, and some other polysaccharides greatly enhance the formation of exolipase by *Serratia marcescens*. *J Bacterial* 138: 663-670.

Zhang, Y. (2009). Protein structure prediction: when is it useful? Current Opinion in Structural Biology 19(2): 145-155.

Zheng, L., Baumann, U. and Reymond, J. L. 2004. An efficient one-step site-directed and site-saturation mutagenesis protocol. *Nucleic Acids Res* 32: e115.

All of the compositions and methods disclosed and claimed herein can be made and executed without undue experimentation in light of the present disclosure. While the compositions and methods of this invention have been described in terms of exemplary embodiments, it will be apparent to those of ordinary skill in the art that variations may be applied to the composition, methods and in the steps or in the sequence of steps of the method described herein without departing from the concept, spirit and scope of the invention. More specifically, it will be apparent that certain agents that are both chemically- and physiologically-related may be substituted for the agents described herein while the same or similar results would be achieved. All such similar substitutes and modifications apparent to those of ordinary skill in the art are deemed to be within the spirit, scope and concept of the invention as defined by the appended claims. Accordingly, the exclusive rights sought to be patented are as described in the claims below.

This invention may be combined in many different forms and should not be construed as limited to the embodiments set forth herein; rather these embodiments are provided so that this disclosure will fully convey the invention to those of ordinary skill in the art. Many modifications and other embodiments will come to mind to one of ordinary skill in the art to which this invention pertains having the benefit of the teachings presented in the foregoing description. Although specific terms are employed, they are used as in the art unless otherwise indicated.

What is claimed is:

1. A fat-containing product having reduced trans-fatty acid moieties, or essentially no trans-fatty acid moieties, produced by a method comprising: contacting a substrate that comprises one or more trans-unsaturated fatty acid compounds or one or more long-chain ($\geq C_{12}$) fatty acid moieties with an effective amount of a composition comprising an isolated lipase, or a variant thereof, having lipase activity that comprises:

(a) an amino acid sequence that is at least 95% identical to the amino acid sequence of any one of SEQ ID NO:1, SEQ ID NO:4, or SEQ ID NO:6; or (b) one or more amino acid substitutions corresponding to residues 269, 338, 341, 342, 357, 421, or 425, wherein each amino acid position is numbered by correspondence to a position in the amino acid sequence of the lipase as set forth in SEQ ID NO:1; or (c) a first amino acid substitution in one or more amino acid residues of an amino acid sequence that is at least 95% identical to the amino acid sequence of any one of SEQ ID NO:1, SEQ ID NO:4, or SEQ ID NO:6, wherein the at least a first amino acid substitution confers to the polypeptide a preference for catalysis of long-chain fatty acids, or a trans-selective lipolytic activity, or a combination thereof, for a time sufficient to hydrolyze or esterify at least a portion of the substrate, thereby producing a fat-containing product having reduced, or essentially no trans-fatty acid moieties.

2. The fat-containing product of claim 1, suitable for human consumption.

3. The fat-containing product of claim 1, characterized as a cooking ingredient, or a frying oil.

4. The fat-containing product of claim 1, characterized as an edible lipid, an edible fat, an edible fatty acid, an edible sterol, an edible wax, an edible oil, or an edible triglyceride, or any combination thereof.

5. The fat-containing product of claim 1, characterized as argan oil, canola oil, castor oil, corn oil, coconut oil, cottonseed oil, flax seed oil, grape seed oil, hazelnut oil, hempseed oil, linseed oil, olive oil, palm oil, palm kernel oil, peanut oil, pumpkin seed oil, rapeseed oil, rice bran oil, safflower oil, sesame oil, soybean oil, sunflower oil, or any combination thereof.

6. The fat-containing product of claim 1, characterized as vegetable fat, butterfat, cocoa butter, shea butter, shea oil, kokum butter, milk fat, tallow, lard, lanolin, or any combination thereof.

7. The fat-containing product of claim 1, wherein (c) the at least a first amino acid substitution confers to the polypeptide a preference for catalysis of long-chain fatty acids, when compared to a non-selective or un-substituted lipase.

8. The fat-containing product of claim 1, wherein (c) the at least a first amino acid substitution confers to the polypeptide an increase in hydrolytic or ethanolytic activity in the presence of at least a first trans-fatty acid moiety, when compared to a non-selective or un-substituted lipase.

9. The fat-containing product of claim 1, wherein (c) the at least a first amino acid substitution confers to the polypeptide an increased preference for catalyzing fatty acid moieties having a carbon chain length greater than or equal to fourteen ($\geq C_{14}$), when compared to the wild-type or parent lipase.

10. The fat-containing product of claim 1, wherein (c) the at least a first amino acid substitution confers to the polypeptide an increased preference for catalyzing fatty acid moieties having a carbon chain length greater than or equal to sixteen ($\geq C_{16}$), when compared to the wild-type or parent lipase.

* * * * *